(12) United States Patent
Takesako et al.

(10) Patent No.: US 7,491,405 B2
(45) Date of Patent: *Feb. 17, 2009

(54) ANTIGENIC PROTEIN ORIGINATING IN MALASSEZIA

(75) Inventors: Kazutoh Takesako, Otsu (JP); Takashi Okada, Kyoto (JP); Tomoko Yagihara, Hikone (JP); Masanobu Kuroda, Otsu (JP); Yoshimi Onishi, Kyoto (JP); Ikunoshin Kato, Uji (JP); Kazuo Akiyama, Kawasaki (JP); Hiroshi Yasueda, Sagamihara (JP); Hideyo Yamaguchi, Kawasaki (JP)

(73) Assignee: Takara Bio Inc., Otsu-shi (JP)

( * ) Notice: Subject to any disclaimer, the term of this patent is extended or adjusted under 35 U.S.C. 154(b) by 556 days.

This patent is subject to a terminal disclaimer.

(21) Appl. No.: 11/116,371

(22) Filed: Apr. 28, 2005

(65) Prior Publication Data

US 2008/0069829 A1    Mar. 20, 2008

Related U.S. Application Data

(62) Division of application No. 10/109,670, filed on Apr. 1, 2002, now Pat. No. 6,911,208, which is a division of application No. 09/091,097, filed as application No. PCT/JP96/03602 on Dec. 10, 1996, now Pat. No. 6,432,407.

(30) Foreign Application Priority Data

| Dec. 12, 1995 | (JP) | ................................. 7-346627 |
| Sep. 5, 1996 | (JP) | ................................. 8-257612 |
| Sep. 5, 1996 | (JP) | ................................. 8-257613 |

(51) Int. Cl.
*A61K 39/35* (2006.01)
*A61K 38/00* (2006.01)
*C12P 21/04* (2006.01)

(52) U.S. Cl. .............. 424/275.1; 424/276.1; 424/184.1; 530/300; 530/350; 435/69.1; 435/69.7

(58) Field of Classification Search .............. 424/275.1, 424/184.1; 530/300, 350
See application file for complete search history.

(56) References Cited

U.S. PATENT DOCUMENTS 6,432,407 B1 * 8/2002 Takesako et al. ......... 424/184.1

OTHER PUBLICATIONS

Sentandreu et al., "Cloning of cDNA coding for *Candida albicans* cell . . . " *Journal of Medical & Veterinary Mycology*, vol. 33, No. 2, 1995, pp. 105-111, XP001022554.

Lindblom et al., "Cloning and sequencing of the cDNA encoding the *Pityrosporum* . . . " *Journal of Allergy and Clinical Immunology*, vol. 97, No. 1 part 3, 1996, p. 374 XP001034009.

Yasueda et al., "Identification and cloning of two novel allergens from the lipophilic yeast . . . " *Biochemical and Biophysical Research Communications*, vol. 248, No. 2, Jul. 20, 1998, pp. 240-244, XP002184076.

Moser et al., "Cloning and Expression of Recombinant *Asperigilus*" *Journal of Immunology*, vol. 149, No. 2, (1992) p. 454-460.

Johansson et al., "IgE-binding Components in *Pityrosporum orbiculare* . . . " *Acta Derm Venereol* (Stockh) vol. 71, 1991, pp. 11-16.

Zargari et al., "Identification of Allergen Components . . . ", *Allergy*, 1994, vol. 49, pp. 50-56.

Jensen-Jarollim et al., "Atopic dermatitis of the face . . . ", *J. Allergy Clin. Immunolo.*, vol. 89, No. 1, 1992, pp. 44-51.

Arrunda et al., "*Aspergillus fumigatus* AllergenI . . . ", *J. Exp. Med.*, vol. 172, No. 5, 1990, pp. 1529-1532.

Garrard et al., "Two Genes Encode the Major Membrane . . . ", *J. Biol. Chem.* vol. 264, No. 23, 1989, pp. 13929-13937.

Matsumoto et al., "Iron- and Manganese-Containing Superoxide . . . ", *Biochemistry*, vol. 30, No. 13, 1991, pp. 3210-3216.

Ludwig et al., "Manganese Superoxide Dismutase . . . ", *J. Mol. Biol.*, vol. 219, No. 2, 1991, pp. 335-358.

Savolainen et al., "Crossreacting IgE Antibodies to *Pityrosporum* . . . ", *Clinical and Experimental Allergy*, vol. 22, 1992, pp. 469-474.

Rudinger et a., "Characteristics of the Amino Acids as Components . . . ", *Peptide Hormones*, Edited by Parsons, University Park Press; Baltimore, 1976.

M. Carmen Menendez et al., "Cloning and expression of *Mycobacterium fortuitum* superoxide dismutase gene", FEMS Microbiology Letters, vol. 134, No. 2-3, (1995), pp. 273-278. (XP-001063033.

R.A. Hallewell et al., "Sequence of a CDNA Coding For Mouse Manganese Superoxide Dismutase", Nucleic Acids Research, vol. 14, No. 23, (Dec. 9, 1986), p. 9539. XP-001057377.

* cited by examiner

*Primary Examiner*—Robert B Mondesi
*Assistant Examiner*—Padma V Baskar
(74) *Attorney, Agent, or Firm*—Birch, Stewart, Kolasch & Birch, LLP

(57) ABSTRACT

A substantially pure, isolated, antigenic protein from fungi of the genus *Malassezia*, characterized in that said antigenic protein has a binding ability to IgE antibodies from patients with allergoses; an antigenic fragment derived from the antigenic protein; and an antibody against the antigenic protein or fragments thereof. According to the present invention, there can be provided an isolated and purified antigenic protein having high purity from *Malassezia*, antigenic fragments thereof, and a specific antibody against those antigenic protein or fragments thereof. In addition, there can be provided a diagnostic agent, a therapeutic agent, or a prophylactic drug for *Malassezia* allergoses, wherein the agent includes, as an active ingredient, the antigenic protein or fragments thereof.

4 Claims, 37 Drawing Sheets

```
  1  GTTGAGCTCTGTGCTCTGAAGCGCTCGCCGCAGCTCTACTAAGGCTCTGA   50
     ||||||||||||||||||||||||||||||||||||||||||||||||||
  1  GTTGAGCTCTGTGCTCTGAAGCGCTCGCCGCAGCTCTACTAAGGCTCTGA   50

51  AGCAGCCGCTTACGCTCCCGGTCTGCTCGCCGTCCCATTGCGCTACGGCTG  100
     ||||||||||||||||||||||||||||||||||||||||||||||||||
 51  AGCAGCCGCTTACGCTCCCGGTCTGCTCGCCGTCCCATTGCGCTACGGCTG  100

101  GCTCGTGGCTACGCCTCGAGCTCGGAGCCGTACGATGTCATTGTGATCGG  150
     ||||||||||||||||||||||||||||||||||||||||||||||||||
101  GCTCGTGGCTATGCCTCGAGCTCGGAGCCATACGATGCATTGTGATTGG  150

151  CGGTGGCCCCGGTGCTACGTGCCATCAAGGCCCACAGGGTGTC  200
     ||||||||||||||||||||||||||||||||||||||||||||||||||
151  TGGTGGCCCCGGTGGCTACGTGCCGATCAAGGCCGAGGGTGGTC  200

201  TGAAGACTGCCGTGTTGAGAAGCCGTGCCCTTGGCGTACGTGCTTG  250
     ||||||||||||||||||||||||||||||||||||||||||||||||||
201  TGAAGACTGCCATGTGTTGAGAAGTCGTTGGCGTGGTACCTGCTTG  250

251  AACGTGGGCTGTATCCCGTTCCAAGTGTTGCTCAACAACTCGCACATCTA  300
     ||||||||||||||||||||||||||||||||||||||||||||||||||
251  AACGTGGGCTGTATCCCGTTCCAAGTGTTGCTGAACAACTCGCACATCTT  300
```

FIG.17A

```
301  CCACCAGAGCGCAGCATGACCTCAAGAACCGCGTATTGAGTCGGCGACA  350
     ||||||||||||||||||||||||||||||||||||||||||||||||
301  CCACCAGAGCGCAGCACGACCTCAAGAACCGCGTATTGAGTCGCGAGG  350

351  TTAAGCTGAACCTCCCGCAGATGCTCAAGGCTCGAAGAGAGCTCGGTTACT  400
     || |||||||||||||||||||||||||||||||||||||||||||| ||
351  TCAAGTTGAACCTGCCGCAGATGCTCAAGGCTCGAAGAGAGCTCGGTCACT  400

401  GCACTCACCAAGGGTGTCGAGGGCTGTTCAAGAGAACAAGGTCGACTA  450
     | ||||||||||||||||||||||| ||||||||||||||||||||||
401  GCGCTCACCAAGGGTGTCGAGGGCCTGTTCAAGAGAACAAGGTCGACTA  450

451  CATCAAGGCACTGCCAGCTTGCCAGCCCCACGAGCGGTGACGTGAAGC  500
     |   ||||||||||||||||||||||||||||||||||||||||||||
451  CCTCAAGGCACTGCCAGCTTGCGAGCCCTACGAGCGTGACGTGAAGC  500

501  TGAACGATGGGTGTGAGATCAGGGCAAGAACATCATCATTGCA  550
     |||||||||| ||||||||||||||||||||||| |||||| ||
501  TGAACGATGGCGTGAACAGATTGAGGGCAAGAACATTATCATTGCG  550

551  ACCGGCTCGAGTGACGCCCTTCCCGGGTGTTGAAATCGACGAGGAGCA  600
     ||||||||||||||||||| ||||||||| ||||||||| ||||||||
551  ACTGGCTCGAGTGACGCCCTTCCCGGTGTGAGATCGAGGAGCA  600
```

FIG.17B

```
601 GATCATCAGTCTCGACGGGTGCGCTCGCTCAAGGAGGTCCCGAGAAGA 650
    |||  ||||||||||||||||||||||||||||||||||||||||||||
601 GATTATCAGTCTCGACGGGTGCGCTCGCTCAAGGAGGTCCTGAGAAGA 650

651 TGGTCGTGATCGGTGTGTGTCTTGAGCTTGGCAGGCGTGTGG 700
    ||||||||||||||||||||| || |||| |||| ||||||||
651 TGGTCGTGATCGGTGTGTGTCGTGGAGCTCGGTAGCGTGTGG 700

701 ACCCGTCTGGTGCCAAGGTGACCGTGAGTTCCAGGAGGCGATCGG 750
    | |||||||||||||||||||||||||||||||||||| ||||||
701 AGCCGTCTGGGGCCAAGGTGACCGTGAGTTGAGTTCCAGGACGCGATTGG 750

751 TGGTCCCGGTCTGGACAGCGAGGTGAGCCAACAGTTCAAGAAGCTGCG 800
    ||| |||||||||||||||||||||||||||||||||||||||||||
751 TGGCCCCGGTCTGGACAGCGAGGTGAGCCAGCAGTTCAAGAAGCTGCG 800
```

FIG.17C

```
801  AGAAGCAGGGCAGCATCCACTTCAAGTCGGCACCAAGTCAACGGCATTGAG  850
     ||||||||||||||||||||||||||||||| ||||||||||||||||||
801  AGAAGCAGGGCAGCATCCACTTCAAGTTGGCACTAAGTTGAACGGGATTGAG  850

851  AAGGAGAACGGGCAAGGTGACTG-TCCGCACTGAGGGTAAGGATGGCAAGG  900
     |||||||| ||| ||||  |||  |||||| |||||  |||| |||||||
851  AAGCAGGATGGGCAAAGTGA-TGGTCCGCCAACGCCAAAGACGGCAAGG  900

901  AGCAGGACTACGGATGCCAATGTTGTCTCGCCATTGGCTCGTGCCCG  950
     |||||||||||  || ||||| ||||| |||||| || || |||||
901  AGCAGGACTACGACGCCAACGTTGTCTCGTGTCCATCGGTGTTGCCGCCCG  950

951  GTGACCAAGGCCTCAACCTGAGGCGATCGAGCTGACAAGAA  1000
     |||||||| | || ||||||||| |||||||| ||| ||||
951  GTGACGAAGGCTTGAACCTGAGGCGTTGAGCTTGATAAGAA  1000

1001 GGGCCGTGGTGTGGAGGACGAGTTCAACGTGCAAGGGTGTCA  1050
     ||||||||||||||||||||||||||||||||||||||||||
1001 GGGCCGTGGTGTGGACGATGAGTTCAACACGACGTGCAAGGGTGTCA  1050
```

FIG.17D

```
1051  AGTGCATTGGTGACGCGACGTTCGGCCCCATGCTTGCCACAAGGCCGAG  1100
      ||||||||| |||||||||||||||||||| ||||||||||||||||||
1051  AGTGCATTGTTGACGCGACGTTCGGCCCCTATGCTTGCCACAAGGCCGAG  1100

1101  GACGAGGGTATTGCCGCGTCGCCGAGATGCTTGCCACCGGTTATGGCCACGT  1150
      |||||||||||||||||| |||||||||||||||||||||| |||||||||
1101  GACGAGGGTATGGCCGCGTTGCCGAGATGCTTGCCACCGGTACGGCCACGT  1150

1151  CAACTACGAGCTGATCCCTGGGGTGATCTACACGCCACCCTGAGATCGCGT  1200
      ||||||||||||||||||||||||||||||||||||||||||| || |||
1151  CAACTACGAGCTGATCCCTGGGGTGATCTACACGCCACCCTGAGATTGCGT  1200

1201  GGGTCGGCAAGTCGGAGCAGAGCTCAAGAACGAGGGCGTCCAGTACAAG  1250
      | |||||||||||||||||||||||||||||||||||||||||||||||
1201  GGGTCGGCAAGTCGGAGGAGAGCTCAAGAACGAGGGCGTCCAGTACAAG  1250

1251  GTGGGCAAGTTCCCCTTCCGGCCAACTGCGGTGCCAAGACCAACGTCGA  1300
      |||||||||||||| |||||||||||||||||||||| ||||||||||
1251  GTGGGCAAGTTCCCCATTCCGGCCAACTGCGGTGCTAAGACCAACGTCGA  1300

1301  CACCGACGGCTTCGTCAAGTTCCCTGTGGAGAAGGAGACCGACAAGATTC  1350
      ||||||||| ||||||||||||||||||||||||||||||||||||||||
1301  CACCGACGGTTTGTCAAGTTCCCTGTGGAGAAGGAGACCGACAAGATTC  1350
```

FIG.17E

```
1351  TCGGGCGTGTTCATTATGGGCCCGAACGCTGGCGAGATGATCGCGAGGCT  1400
      ||||| ||||||||| ||||||||||||||| ||||||| ||||||||||
1351  TCGGGGGTGTTCATCATGGGCCCGAACGTCGGCGAGATGATTGCGAGGCT  1400

1401  GGCCTGGCTATGGAGTACGCGCGAGTGCTGAGGATGTTGCGCCACCTG    1450
      |||||||||||||||||||| |||||||||||||||||| |||||||||
1401  GGCCTGGCTATGGAGTACGGTGCGAGTGCAGAGGATGTCGCGCCACCTG    1450

1451  CCACGCGCACCCGACGCTCTCCGAGCGTTCAAGGAGCGTTCGATGGGCG   1500
      |||||||||||||||||||||||||||| | ||||||||| ||||| ||
1451  CCACGCGCACCCGACGCTCGAGCGCCTTCAAGGAGGTGCGATGGCCG   1500

1501  CCTACTCGAAGCCCATTCACTTTGATTCGTAGCCTACCCCGATAGGC     1550
      |||||||||||||||||||||||||| ||||||| |||||||||||||
1501  CCTACTCGAAGCCGATTCACTTTGATTCGTAGTTTCGATAGGC     1550

1551  GCCCGATAGCGTTTTCTCCAAAAAAAAAAAAAAAAAAAAAAAAAA       1600
      ||||||||| ||||| || |||||||||||||||||||||
1551  GCCCGATAGCGTCTTC-CTC-AAAAAAAAAAAAAAAAAAAAAAAAAA    1600

1601  AAAAAAAA........................................  1650
      |||
1601  AAA.............................................  1650
```

FIG.17F

```
  1 TTCTC----TCTGTTGATGAAGCTCAACCCCAAGGTCACCGAGCTGCCCT    50
       ||   |||||||||| ||||||||||||| ||||||||||||||||
 -1 ..CTAAGAT-TCTTGATGAAGCTGAACCCCAAGGTTACCGAGCTCCGCCT    48

51 GTACGACATCCGTTGCTCCGGTGTTGCTTGCGACCTTCGCACATCA       100
    |||||||||||| |||||||||||||||| ||||| |||||||||
 49 GTACGACATCCGCTGCTCCGGTGTTGCGCTCCGGATCTCGCACATCA       98

101 ACACGCCCTGCGGTGACCTCGGGCTACGCCCAGGAC?ATCTTGAGGGTGCC  150
    |||  |||||||||| ||||| ||||||||||||||  ||| |||||||
 99 ACACCCCCGGCGGTGACTTCGGGAGTACGCCCAGGACGACGAGGAGGTGCC  148

151 GTTGACGGCGCAAAGATTGTCCTGAGCGATCGTCAACTGACCCTCGATGTCCGTG  200
    || |||||||| ||||||||||||  |||||||||| ||||| ||||||||
149 GTCGACGGTGCGGAGATTGTCTGAATCCCCGATCGTCAACTCGTTATGCCGGAAGCC  198

201 CGGCATGACCCGTGACGATCGTTCAACTGACCCTCGATTGTCCGTG       250
    |||||||||||||||||||||||||||||||||||||||||||||
199 CGGCATGACCCGTGACGATCGTTCAACTGACCCTCGATTGTCCGTG       248

251 ACCTCGCCCAAGACCGTGGCCAAGTTGCCCCCAAGGCCTACATTGGTATC   300
    |||||||||||| |||||||| |||||||||||||||||||  |||
249 ACCTCGCCCAAGAGTGTGCCAAGGTCTAAGTGCCCCAAAGGCTTACATCGGCGTC    298
```

FIG.18A

```
301  ATCTGAACCCGTCAACTCGACGTGCCGATGTCGCCGAGTGTTCAA  350
     |||||||||||||||||||| ||||||||||| ||||||||| ||
299  ATCTGAACCCGTCAACTCGACGTGCCGATCGTCGCCGAGTGTTAAA  348

351  GAAGGGCGGTGTACGAGACCCCAAGCGCCTTCGGTGTGACCACGCTCG  400
     |||||||||||||||||||||||||||||||||||||||||||||||
349  GAAGGCCGGTGTACGAGACCCCAAGCGCCTTCGGTGTGACCACGCTCG  398

401  ACACCACGCGTGCGGCCACCTTCGTGGGCATACTGCTCGGAACCG  450
     |||||||||||||||||||||||||||||||||||||||||||||
399  ACACCACGCGGGCGGCCACCTTCGTGGGCATTGCTCGGAACCG  448

451  CAGACCACCAATGTCCGTCATTGGTCGTCACTCGGTGTGACCATCGT  500
     |||||||||||||||||||||||||||||||||||||||||||| ||
449  CAGACCACCAAGTCCGTCATTGTGGCGTCGGGTGTGACCATTGT  498

501  GCCCTCTGGTCTCGAGGTGACAAGGTGCAGGCCGGAGC  550
     |||||||||||||||||||||||||||||||||||||
499  GCCCCTGATCTCGAGGGTGACAAGGTGCAGGCCGGAGC  548

551  AGTACGACAAGCTTGTCACCGCATTCAGTTCGGTGTGACGAGGTCGTT  600
     ||||||||||||||||||||||||||||||||||||||||||||| |
549  AGTACGACAAGCTTGTGCACCCAGTTCGGTGGTGTGACGAGGTCGTC  598
```

FIG. 18B

```
601  AAGGCCAAGGACGGTTCGGGTTCGGGACGCTGTCGATGGCCTACGGC  650
     |||||||||||||||||||||||||||||||||||||||||||||||
599  AAGGCCAAGGACGGTTCGGGTTCGCCGGTGCCTCGACGCTCGATGGCCTACGGC  648

651  CGCTGTCTTCACTGAGGGCCCTCAAGGCCTTGAGCGTGAGGCGGTGA  700
     |||||||||||||||||||||||||||||||||||||||||||||||
649  CGCTGTTTTCACCGAGGGCCCTGCCAAGGCTCGACGGTCGAGGCGGTGA  698

701  CGCAGTGCACCTTGCGTTGAGAGCCCCCCCGTTCAAGGACCAGGTTGACTTC  750
     |||||||||||||||||||||||||||||||||||||||||||||||
699  CGCAGTGCACCCTTGCGTCGAGAGCCCCCCGTTCAAGGACCAGGTCGA?TTC  748

751  TTCGCTTCCGCCCCGTCGAGTTCGGCAGGGCGTGAAGAACATCCCTGC  800
     |||||||||||||||||||||||||||||||||||||||||||||||
749  TTCGCTTCCGCCCCGTCGAGTTCGGCCGAGGGGTGAAGAACATCCCTGA?  798

801  CCTGCCCAAGCTCACCGAGGAGCAGAAGCTG?T?GACGCCCTGCCTGC  850
     |||||||||||||||||||||||||||||||||||||||||||||||
799  TCTGCCCGAAGCTCACCGAGGAGCAGAAGCTG?T?GACGCCCTGCCTGC  848
```

FIG.18C

```
851  CCGACCTTGCCAAGAACATCAAGAAGGGTGTTGCCGAGAAC  900
     ||||||||||||||||||||||||||| ||||||||||||
849  CCGACCTTGCCAAGAACATCAAGAAGGGCGTTGCCGAGAAC  898

901  CCCTAAATGCGCAGAACCAGC-TTCCACGGAGCTTGCCAAGGAAAGGA  950
     |||  ||||||| ||       ||| ||||| |||||| |||||||
899  CCGTAAATGCGCCA-AAGCAATTTTTACGGAGCTTGCGGAAGGAAAGGA  948

951  AACGCACATTT?TATAGAGCGTAGCTTGTCCCTTTCCATTTAAAAAAA  1000
     ||  ||| ||| |||||| ||||| |||||| |||||  ||||||||
949  AATGTACGTTT?TATAGAACGTAGATCGTCCCTTCCACCTAAAAAAAA  998

1001 AAAAAAAAAAAA.........  1050
     ||||||||||||
999  AAAAAAAAAAAA.........  1048
```

FIG.18D

```
MF-1    1  GCCTGGTGATCCTACTGCTAAGGGTAACGAGATCCCGACACCC     50
           |||   |  |  |     |||         |||     |
MF-2   -1  ...C-GGAAAT--TG--GCT-C-G-A------CGA---TCCC-A-ACGC   48

MF-1   51  T-CATGGGC-TACACATCCCCTGA-CCCGGAGCTGA----CTCGGGTGAG  100
           | ||| ||  ||| ||  |||      ||    ||        |||   
MF-2   49  TACGTTTGCATACGTGCCGTACAGCCCCG-AGCTCGAGGAC-CACAA-AG   98

MF-1  101  GTGTGTGTATCCCACCACCTTCAAGACCCGCGACGAG-TGGAAGGGCA    150
            |||||| || |   | | ||||||  |   |||||  ||||||||
MF-2   99  -TGTGTGGCATGCCAGAGCTTCCAGAGCCACGA-GCGCTGGAAGGGCA    148

MF-1  151  AGAAGGTTGTGATTGTCTCGAT-CCCGGGTGCCTACACCCCATC-TGCC    200
           ||||||| ||||| ||   |    ||||||   |  ||||   | ||||
MF-2  149  AGAAGGTGGTGATTGTGTGCCGG-TGCGTTCACGCCGA-CGTGC-     198

MF-1  201  ACCAGCAGCAC-ATCCCCCGCTTGTGAAGCGTGTG-----GAT---G-AG  250
           ||| || ||   |||   || |    | ||||||     ||    | ||
MF-2  199  ACC-GC-GAACCATGTGCC-GT-A--CGTG-GAAAAGATCCAGGAG       248
```

FIG.19A

```
251 CTCAAG-GCCAAGGGGTGTCGACGCCCGT-GTACGTCAT-TGCGTCGAACGA   300
        |||||| |||||||| ||||||||||| |||| ||||| ||| |||||||||
249 CTCAAGAGC-AAGGGCGTCGACGAGGTCGTG-GTGATCT-CGGCGAACGA    298

301 CCCCTTCGT-CATG-GCTGCCTGGGCA--ACTTTCAA-CAACGCCAAGGA    350
        |||| |||| |||| ||| ||||||||   || ||| ||| ||||||||
299 CCCGTTCGTGC-TGAGC-GCATGGGGCATCAC--CGAGCA-CGCCAAGGA   348

351 CAAGGTCGTC-TTTGC-CACCGACACATTGACCTG-GCCTTCTCCAAGGCTC 400
        ||||||||||   |||| ||||| |||||| ||||||  ||||||| |||
349 CAACCT-GACGTTGCGCAG-GACGTCAAC-TGCGAGTTCCAAG-CAC     398

401 TCGG-CGCGACGATGACCTGAGCGCC-AAG--CACTTTGG--TGAGCGC    450
        ||||   |||||| ||||| |||||  |||  ||||| ||  || ||||
399 TTTAACGCGCAGCTCACCTGT-CGTCGAAGGGCA-TG-GGCCCTG--CGC  448

451 ACGGCCCGCTACGCTCTGATCATTGA-CGACAACAAGATTGTCGA---CT 500
        |||||| ||||||| ||||| || ||  ||||| ||| ||| ||   ||
449 ACCGCGCTACGCGCTGATCGC-GAACGACCTCAAG---GTCGAGTACT  498
```

FIG.19B

```
501  TTG-CTTCGGACGAGGGGA-CACTGGCAAGCTCCAGAACGCGTCGATCG   550
        ||| |||||||| ||||| |||  |||  || |||  ||  ||| ||
499  TTGGCATCG-ACGAGGGCGAGC--C-G--AAGC----AGT-CG---TCGGCCG  548

551  AC-ACGATCCTCACCAAGGTCTAAAATGGGCATGTGCGT--TGT-GTGA     600
        || ||   ||  ||||||| ||  || |||| |||||    ||| ||
549  -CGACGGGTCTGAGCAAGCTGTAG--TGCCG--T-T-C--TACT-TAGTCA   598

601  CCACTACCTAAAGGTCGTAGAGT-TCCAAGTCAAGTCGTATATTTTTT      650
       || ||  ||  || ||  ||    ||  || | |||  |   ||
599  --A--AC--AA----TC-G---A-GTC---G-CGTA--A-----          648

651  TTTTAAAAAAAAA............................             700
       |||||||||
649  ----AAAAAAAA.............................             698
```

FIG.19C

```
MF-3    1 GG-GA--ACG-T--C-A------TGACTGA-G-----TA-C-A-C        50
            ||  || ||| |  | |      ||||||| |     || | | |
MF-4    1 GATGTTCACGCTTGACGGCGCTG-CTGCCGCCCCTCGGAAC              50

51 TCT-CCC---T-----C-C----T-C---TGCC-CTAC-GCC-TA         100
          ||| |||   |     | |    | |   |||| |||| ||| ||
       51 GCCGCCCAGATGGGCGCACCAAGTACACGCTGCCGCCGCCGCTGTA        100

101 CGA-T--G-CGC--TGAGCCGTTTATCTCTAAG-GAGATCATG-ACGT       150
          ||| |  | |||  |||||||||||||||||| ||||||||| ||||
      101 CGACTACGGGCGCTCGAGCCGGATCGG-GCGAGATCATGGA-GA-        150

151 C-CACCACGACAAGCACCACCAG-ACCTACGTGAACAACCTCAACGCCGC    200
          | |||||||||||||||||||| ||||||||||||||||||||||||||
      151 CGCACTACGAGAAGCACCACC-GCACCTACGTCAACAACCTGAACGCCGC    200

201 CGAGAAGG-CGTACGCTGAGGCGACG-GC-CGGCGAA-C-GA-CGTGCTTA   250
          |||||||| |||||||||||||||| || ||||||| | || ||||| |
      201 -G-GA-GGACA-A-GCTGAT-CGAGCGCCTCCCGCTCCCCAGAGCGCTCG    250

251 AGC-AGAT--C-CAGCTGCAGAGTGCGATCAAGTTCAACGGGGTGCCA      300
          ||| ||||  | ||||||||||||||||||||||||||||||||||||
      251 -GCGAGATTGCGCAGCTG-A-AC-GCGATCAAGTTCAACGGGGTGCCA      300
```

FIG.20A

```
301  CATCAACCACTCGCTGTTCTGAAGAACCTGGCCCC--C----CAGAGCGA    350
     ||||||||||||||||||||||||||||||||||||      ||| ||
301  CATCAACCACTCGCTCTTCTGAAGAACCTGCGCGACGAACA-AG-G---    350

351  G-GTGGTG-GC-CAACT-GAACGA---TGGCCCTCTCAAGCAGGCCATCG    400
      | |  || ||  | || ||| ||   |||  |  | | ||||||||||
351  GCGGCGGCGAGCTCGACTCGAGCTG-CGCTC-C--GC-G---ATCG    400

401  AGCAG-GAGTT----C---GG-CGACTTTG---A-GAAGTTCAAGACGACCTT    450
     |  || | |||   |   || || |||||   | | | ||||| ||
401  ACC-GCGACTTTGGCTCGGTCGAC---GCCATGAAGG--A-GAAG---TT    450

451  CAACACGAAAG-GCG-GCCGGGCATCCAGGGTTC-G-GGCTGGCTG-TGGCT    500
     |||| ||| || ||| ||||||||||||||  || | ||||||||| |||||
451  CAACGCG--G---GCGCTGGGGCATCCAGGG--CAGGGGCTGGG-GCTGGCT    500

501  CGG---TGTTGCCC--CGACGG-GCAACCTGGACCCTGGTCGTTG-CCAAG-G    550
     |||    |||||||  ||| || ||   |||| |||||||| |||  ||||  |
501  CGGCCTGAACCCTGAACCCACCAGAAGCTGACATCATCAC-GACC--GCG    550

551  A--CCAGGACCCGCTCAC-GACGCACCCCCG-TCATTGGC-TGGGATGG    600
     |  |||||||||| |||   ||| | |||||  ||||||| |||||| |
551  AACCAGGACCCGGCTC-CTGTGCCACAAGCC-GCTGATTGGCATCG--ATG-    600
```

FIG.20B

```
601  C-TGGGAGCACGGCCTGGTACCTGCAGTACAAGAACGACAAGGCTTC---CT  650
        | |||||||||||| ||||||||||||||||| |||||||||||||   ||
601  CGTGGGAGCACGCGTTCTACCTGCAGTACAAGAACGTCAAGGC---CGACT  650

651  ACCTT-AAGGCC-TGGTGGAAGCTGTGAACTG-G-GCCGAGGCCGAGAA   700
       |||| ||||   |||| |||  |||||||   |  |||| ||||||||
651  AC-TTCAAGGCCGATC-TGGACCGTGATCAACTTTGAG--GAGGCCGAGAA  700

701  GCGCTTCCTCGAGGGTAAGAAGAAGGC-C-CAGCT---GTAA-TGG-CACG  750
      ||| | | || | ||   |  || ||   |||||    |||| ||| ||||
701  GCG-T-C-TC-A---GA-G-GGCGCTC-GCCAAG-AACTAGACACG       750

751  TTTGTAGATGATGAACGACACACGATTTTAGGT-CGCACGG-CC-G---A   800
       |||  |       ||   |  | | |     |  | |    || |   |
751  TTCG--GTTTTTTTTT-CTC-CG-T---AGCTTCGCAATGACCTGCCCA    800

801  GGCTACTAAAAAAAAAAAAAAAAAAAAAAAAAAAAAAAAAAAAAAAAAAAA  850
       | ||   |||||||||||||||||||||||||||||||||||||||||||
801  CGCTAAAAAAAAAAAAAAAAAAAAAAAAAAAAAAAAAAAAAAAAAAAAAA  850

851  AAAAAA.............................................  900
       ||||||
851  AAAAAAAAAAAAAAAAAAAAAAAAA..........................  900
```

FIG.20C

| No. | Amino Acid Sequence | Number of Residual Group | HPLC Retention Time (min) |
|---|---|---|---|
| 1 | PGDPTATAKGNEIPDT | 16 | 23.5 |
| 2 | ATAKGNEIPDTLMGY | 15 | 32.4 |
| 3 | NEIPDTLMGYIPWTPEL | 17 | 44.0 |
| 4 | TLMGYIPWTPELDSG | 15 | 40.8 |
| 5 | IPWTPELDSGEVCGI | 15 | 39.4 |
| 6 | ELDSGEVCGIPTTFK | 15 | 33.0 |
| 7 | EVCGIPTTFKTRDEW | 15 | 42.1 |
| 8 | PTTFKTRDEWKGKKV | 15 | 22.9 |
| 9 | TRDEWKGKKVVIVSI | 15 | 29.9 |
| 10 | KGKKVVIVSIPGAYT | 15 | 29.9 |
| 11 | VIVSIPGAYTPICHQ | 15 | 34.0 |
| 12 | PGAYTPICHQQHIPPLV | 17 | 44.6 |
| 13 | PICHQQHIPPLVKRV | 15 | 27.7 |
| 14 | QHIPPLVKRVDELKA | 15 | 29.9 |
| 15 | LVKRVDELKAKGVDA | 15 | 23.3 |
| 16 | DELKAKGVDAVYVIA | 15 | 31.3 |
| 17 | KGVDAVYVIASNDPFVM | 17 | 39.8 |
| 18 | VYVIASNDPFVMAAW | 15 | 43.2 |
| 19 | SNDPFVMAAWGNFNNA | 16 | 39.1 |
| 20 | VMAAWGNFNNAKDKV | 15 | 30.4 |
| 21 | GNFNNAKDKVVFATD | 15 | 26.8 |
| 22 | AKDKVVFATDIDLAF | 15 | 37.4 |
| 23 | VFATDIDLAFSKALG | 15 | 39.6 |
| 24 | IDLAFSKALGATIDL | 15 | 40.3 |
| 25 | SKALGATIDLSAKHF | 15 | 29.8 |
| 26 | ATIDLSAKHFGERTA | 15 | 26.3 |
| 27 | SAKHFGERTARYALI | 15 | 28.4 |
| 28 | GERTARYALIIDDNK | 15 | 27.5 |
| 29 | RYALIIDDNKIVDFA | 15 | 35.7 |
| 30 | IDDNKIVDFASDEGD | 15 | 29.3 |
| 31 | IVDFASDEGDTGKLQ | 15 | 28.1 |
| 32 | SDEGDTGKLQNASID | 15 | 22.6 |
| 33 | TGKLQNASIDTILYKV | 16 | 34.8 |

HPLC Analysis Conditions:
    TSK-gel ODS 4.6 φ × 250 mm: UV 210 nm: 0-60% of
    60-minute linear gradient elution with acetonitrile
    containing 0.05% TFA: 1.0 ml/min: 40°C

FIG.21

```
Genomic
DNA      1   AGACAGGAGGACATGGTTTAGAAGCACAATTCGGGTAGCTGGCGTGAAGGATACTC       60
cDNA     1                                                                  1

61   GCTGAGAAATTCACTTTCCCCGCTGACGGCCCAGACCCCGAACTGTCCCGAATTACCA      120
         1                                                                  1

121   AGCAAATGCACGTGACGTTTGTGGAGGCTCGGGGATTATCAGGCCACGTATCAGTGAGCC    180
         1                                                                  1

181   GAGCACCGCGTGGCTTCGGCTGCTGCATATAAAGCCGGTGGGGCCGTGCTCACAGCTTC     240
         1                                                                  1

241   ATCTTCCAGGACAATCATTATGCCTGGTGTAGGTACCGCGAAGTGACACGCATGCTGACC    300
         1                                         M  P  G                   1

301   ATCAGGATCCTACTGCTACTGCCAAGGTAACGAGATCCCGACACCCTTATGGGCTACA      360
         1    D  P  T  A  T  A  K  G  N  E  I  P  D  T  L  M  G  Y         18

361   TCCCCTGGACCCCGGAGCTGGACTCGGGTGAGGTGTGTGGTATCCCCACCACCTTCAAGA    420
        19    I  P  W  T  P  E  L  D  S  G  E  V  C  G  I  P  T  T  F  K   38

421   CCCGCGACGAGTGGAAGGGCAAGAAGGTTGTGATTGTCTCGATCCCGGGTGCCTACACCC    480
        39    T  R  D  E  W  K  G  K  K  V  V  I  V  S  I  P  G  A  Y  T   58
```

FIG.23A

```
481 CCATCTGCCACCAGCACATCCCCGCTTGTGAAGCGTGTGGATGAGCTCAAGGCCA  540
 59  P  I  C  H  Q  Q  H  I  P  P  L  V  K  R  V  D  E  L  K  A    78

541 AGGGTGTGACGCCCGTGTAGTGTCATTGCCCTTGTCGTCATGGGTATGTACT  600
 79  K  G  V  D  A  V  Y  V  I  A  S  N  D  P  F  V  M    95

601 GCTCTGTCATTCTTTATGCTAACCGACACAGCTGGGGCAACTTCAACAACGCCAAGG  660
 95              A  A  W  G  N  F  N  N  A  K           110

661 ACAAGGTCGTCTTTGCCACCGACATTGACCTGGCCTTCTCCAAGGCTCTCGGCGACGA  720
111  D  K  V  V  F  A  T  D  I  D  L  A  F  S  K  A  L  G  A  T   130

721 TCGACCTGAGCGCCAAGCACTTTGGTGAGCGCACCGCTAGGTACGCTCTGATCATTGACG  780
131  I  D  L  S  A  K  H  F  G  E  R  T  A  R  Y  A  L  I  I  D   150

781 ACAACAAGATTGTCGACTTTGCTTCCGGAGACGAGGGCGACACTGGCAAGCTCCAGAACGCGGT  840
151  D  N  K  I  V  D  F  A  S  D  E  G  D  T  G  K  L  Q  N  A   170

841 CGATCGACACGATCCTCACCAAGGTCTAAAATGGCCATGCGTTGTGTGACCACTACC  900
171  S  I  D  T  I  L  T  K  V  *                              180

901 TAAAGGGTCCGTAGAGTTCCAAGTCGTATATTTTTTTACAGGATGGTGTGTA  960
180

961 CTGCCACCTGCCCTTTGAGCAAGGGGTGCCAG  991
180
```

FIG.23B

SEQUENCE LISTING

<160> NUMBER OF SEQ ID NOS: 58

<210> SEQ ID NO 1
<211> LENGTH: 618
<212> TYPE: DNA
<213> ORGANISM: Malassezia furfur
<220> FEATURE:
<221> NAME/KEY: misc_feature
<222> LOCATION: (1)..(618)
<223> OTHER INFORMATION: Strandedness:double-Topology:linear-Molecule
      Type:cDNA to mRNA

<400> SEQUENCE: 1
gcctggtgat cctactgcta ctgccaaggg taacgagatc cccgacaccc tcatgggcta      60
catcccctgg accccggagc tcgactcggg tgaggtgtgt ggtatcccca ccaccttcaa     120
gacccgcgac gagtggaagg gcaagaaggt tgtgattgtc tcgatcccgg gtgcctacac     180
ccccatctgc caccagcagc catcccccc gcttgtgaag cgtgtggatg agctcaaggc     240
caagggtgtc gacgccgtgt acgtcattgc gtcgaacgac cccttcgtca tggctgcctg     300
gggcaacttc aacaacgcca aggacaaggt cgtctttgcc accgacattg acctggcctt     360
ctccaaggct ctcggcgcga cgatcgacct gagcgccaag cactttggtg agcgcacggc     420
ccgctacgct ctgatcattg acgacaacaa gattgtcgac tttgcttcgg acgagggcga     480
cactggcaag ctccagaacg cgtcgatcga cacgatcctc accaaggtct aaaatggcgc     540
atgtgcgttg tgtgaccact acctaaaggg tccgtagagt tccaagtcaa gtcgtatatt     600 tttttttaa aaaaaaaa                                                    618

<210> SEQ ID NO 2
<211> LENGTH: 551
<212> TYPE: DNA
<213> ORGANISM: Malassezia furfur
<220> FEATURE:
<221> NAME/KEY: misc_feature
<222> LOCATION: (1)..(551)
<223> OTHER INFORMATION: Strandedness:double-Topology:linear-Molecule
      Type:cDNA to mRNA

<400> SEQUENCE: 2
cggaaattgg ctcgacgatc cccaacgcta cgtttgcata cgtgccgtac agccccgagc      60
tcgaggacca caaagtgtgt ggcatgccga cgagcttcca gagccacgag cgctggaagg     120
gcaagaaggt ggtgattgtc gcggtgcccg gtgcgttcac gccgacgtgc accgcgaacc     180
atgtgccgcc gtacgtggaa aagatccagg agctcaagag caagggcgtc gacgaggtcg     240
tggtgatctc ggcgaacgac ccgttcgtgc tgagcgcatg gggcatcacc gagcacgcca     300
aggacaacct gacgtttgcg caggacgtca actgcgagtt ctccaagcac tttaacgcga     360
cgctggacct gtcgtcgaag ggcatgggcc tgcgcaccgc gcgctacgcg ctgatcgcga     420
acgacctcaa ggtcgagtac tttggcatcg acagggcga gccgaagcag tcgtcggccg     480
cgacggtgct gagcaagctg tagtgccgtt ctacttagtc aaacaatcgg gtatagtcgc     540
gtaaaaaaaa a                                                          551

<210> SEQ ID NO 3
<211> LENGTH: 728
<212> TYPE: DNA
<213> ORGANISM: Malassezia furfur
<220> FEATURE:
<221> NAME/KEY: misc_feature
<222> LOCATION: (1)..(728)
<223> OTHER INFORMATION: Strandedness:double-Topology:linear-Molecule
      Type:cDNA to mRNA

<400> SEQUENCE: 3

| | | | | | |
|---|---|---|---|---|---|
| gggaacgtca | tgactgagta | cactctccct | cctctgccct | acgcctacga | tgcgctggag | 60 |
| ccgtttatct | ctaaggagat | catgacggtc | caccacgaca | agcaccacca | gacctacgtg | 120 |
| aacaacctca | acgccgccga | gaaggcgtac | gctgaggcga | cggccgcgaa | cgacgtgctt | 180 |
| aagcagatcc | agctgcagag | tgcgatcaag | ttcaacggcg | gtggccacat | caaccactcg | 240 |
| ctgttctgga | agaacctggc | cccccagagc | gagggtggtg | gccaactgaa | cgatggccct | 300 |
| ctcaagcagg | ccatcgagca | ggagttcggc | gactttgaga | agttcaagac | gaccttcaac | 360 |
| acgaaggcgg | ccggcatcca | gggttcgggc | tggctgtggc | tcggtgttgc | cccgacgggc | 420 |
| aacctcgacc | tggtcgttgc | caaggaccag | gacccgctca | cgacgcacca | ccccgtcatt | 480 |
| ggctgggatg | gctgggagca | cgcctggtac | ctgcagtaca | agaacgacaa | ggcttcctac | 540 |
| cttaaggcct | ggtggaacgt | ggtgaactgg | gccgaggccg | agaagcgctt | cctcgagggt | 600 |
| aagaagaagg | cccagctgta | atggcacgtt | tgtagatgat | gaacgacaca | cgattttagg | 660 |
| tcgcacggcc | gaggctacta | aaaaaaaaaa | aaaaaaaaaa | aaaaaaaaaa | aaaaaaaaa | 720 |
| aaaaaaaa | | | | | | 728 |

<210> SEQ ID NO 4
<211> LENGTH: 812
<212> TYPE: DNA
<213> ORGANISM: Malassezia furfur
<220> FEATURE:
<221> NAME/KEY: misc_feature
<222> LOCATION: (1)..(812)
<223> OTHER INFORMATION: Strandedness:double-Topology:linear-Molecule
      Type:cDNA to mRNA

<400> SEQUENCE: 4

| | | | | | |
|---|---|---|---|---|---|
| gatgttcacg | cttgctacgc | gccgcgctgc | tgccgccccc | ctcgcgaacg | ccgcccagat | 60 |
| gggtgtgcgc | accaagtaca | cgctgccgcc | gctgccgtac | gactacggcg | cgctcgagcc | 120 |
| ggcgatctcg | ggcgagatca | tggagacgca | ctacgagaag | caccaccgca | cctacgtcaa | 180 |
| caacctgaac | gccgcggagg | acaagctgat | cgacgcgctc | ccgcagcaga | gcccgctcgg | 240 |
| cgagattgcg | cagctgaacg | cgatcaagtt | caacggcggt | ggccacatca | accactcgct | 300 |
| cttctggaag | aacctcgcgc | cgacgaacaa | gggcggcggc | gagctcgact | cgggcgagct | 360 |
| gcgctccgcg | atcgaccgcg | actttggctc | ggtcgacgcc | atgaaggaga | agttcaacgc | 420 |
| ggcgctcgcg | ggcatccagg | gcagcggctg | ggctggctc | ggcctgaacc | ccacgacgca | 480 |
| gaagctcgac | atcatcacga | ccgcgaacca | ggacccgctc | ctgtcgcaca | gccgctgat | 540 |
| tggcatcgat | gcgtgggagc | acgcgttcta | cctgcagtac | aagaacgtca | aggccgacta | 600 |
| cttcaaggcg | atctggaccg | tgatcaactt | tgaggaggcc | gagaagcgtc | tcaaggaggc | 660 |
| gctcgccaag | aactagacac | gttcggtttt | tttttctcc | gtagcttcgc | aatgacctgc | 720 |
| ccacgctaaa | aaaaaaaaaa | aaaaaaaaaa | aaaaaaaaaa | aaaaaaaaaa | aaaaaaaaaa | 780 |
| aaaaaaaaaa | aaaaaaaaaa | aaaaaaaaaa | aa | | | 812 |

<210> SEQ ID NO 5
<211> LENGTH: 1607
<212> TYPE: DNA
<213> ORGANISM: Malassezia furfur
<220> FEATURE:

<221> NAME/KEY: misc_feature
<222> LOCATION: (1)..(1607)
<223> OTHER INFORMATION: Strandedness:double-Topology:linear-Molecule
       Type:cDNA to mRNA

<400> SEQUENCE: 5

| | | | | | |
|---|---|---|---|---|---|
| gttgagctct | gtgctgaagc | gctcgccgca | gctctctact | aaggctctga | agcagccgct | 60 |
| tacgctcccg | cgtctgctcc | ccattggcgc | tacgccgctg | gctcgtggct | acgcctcgag | 120 |
| ctcggagccg | tacgatgtca | ttgtgatcgg | cggtggcccc | ggtggctacg | tggccgccat | 180 |
| caaggccgca | cagggtggtc | tgaagactgc | gtgtgttgag | aagcgtggtg | cccttggcgg | 240 |
| tacgtgcttg | aacgtgggct | gtatcccgtc | caagtcgttg | ctcaacaact | cgcacatcta | 300 |
| ccaccagacg | cagcatgacc | tcaagaaccg | cggtattgac | gtcggcgaca | ttaagctgaa | 360 |
| cctgccgcag | atgctcaagg | cgaaggagag | ctcggttact | gcactcacca | agggtgtcga | 420 |
| gggtctgttc | aagaagaaca | aggtcgacta | catcaagggc | actgccagct | tgccagcccc | 480 |
| cacgacggtg | gacgtgaagc | tgaacgatgg | tggtgagcag | cagatcgagg | gcaagaacat | 540 |
| catcattgca | accggctctg | aggtgacgcc | cttcccgggt | gttgaaatcg | acgaggagca | 600 |
| gatcatcagc | tcgacgggtg | cgctctcgct | caaggaggtg | cccgagaaga | tggtcgtgat | 660 |
| cggtggtggt | gtgatcggtc | ttgagcttgg | cagcgtgtgg | acccgtctgg | gtgccaaggt | 720 |
| gaccgtggtc | gagttccagg | aggcgatcgg | tggtcccggt | ctggacagcg | aggtgagcca | 780 |
| acagttcaag | aagctgctcg | agaagcaggg | catccacttc | aagctcggca | ccaaggtcaa | 840 |
| cggcattgag | aaggagaacg | gcaaggtgac | tgtccgcact | gagggtaagg | atggcaagga | 900 |
| gcaggactac | gatgccaatg | ttgtgctcgt | gtccattggc | cgtcgcccgg | tgaccaaggg | 960 |
| cctcaacctc | gaggcgatcg | gggtcgagct | cgacaagaag | ggccgcgtgg | tggtggacga | 1020 |
| cgagttcaac | acgacgtgca | agggtgtcaa | gtgcattggt | gacgcgacgt | tcggccccat | 1080 |
| gcttgcgcac | aaggccgagg | acgagggtat | tgccgtcgcc | gagatgcttg | cgaccggtta | 1140 |
| tggccacgtc | aactacgacg | tgatccctgc | ggtgatctac | acgcaccctg | agatcgcgtg | 1200 |
| ggtcggcaag | tcggagcagg | agctcaagaa | cgagggcgtc | cagtacaagg | tgggcaagtt | 1260 |
| cccccttcctg | gccaactcgc | gtgccaagac | caacgtcgac | accgacggct | tcgtcaagtt | 1320 |
| cctcgtggag | aaggagaccg | acaagattct | cggcgtgttc | attatcggcc | gaacgctgg | 1380 |
| cgagatgatc | gccgaggctg | gcctggctat | ggagtacggc | gcgagtgctg | aggatgttgc | 1440 |
| gcgcacctgc | cacgcgcacc | cgacgctctc | cgaggcgttc | aaggagggtg | cgatggccgc | 1500 |
| ctactcgaag | cccatccact | tttgatttcg | taggctaccc | ccgataggcg | cccgatacgt | 1560 |
| tttctctcca | aaaaaaaaaa | aaaaaaaaaa | aaaaaaaaaa | aaaaaaa | | 1607 |

<210> SEQ ID NO 6
<211> LENGTH: 940
<212> TYPE: DNA
<213> ORGANISM: Malassezia furfur
<220> FEATURE:
<221> NAME/KEY: misc_feature
<222> LOCATION: (1)..(940)
<223> OTHER INFORMATION: Strandedness:double-Topology:linear-Molecule
       Type:cDNA to mRNA

<400> SEQUENCE: 6

| | | | | | |
|---|---|---|---|---|---|
| cggatctctc | gcacatcaac | accccgcgg | tgacttcggg | ctacgcccag | gacgacctcg | 60 |
| agggtgccgt | cgacggtgcg | gagattgtgc | tgatccccgc | cggtatgccg | cgcaagcccg | 120 |
| gcatgacccg | tgacgacctg | ttcaactcga | acgcctcgat | tgtccgtgac | ctcgccaagg | 180 |

```
tcgtggctaa ggtcgcccca aaggcttaca tcggcgtcat ctcgaacccc gtcaactcga    240
cggtgccgat cgtcgctgag gtgttcaaga aggccggtgt gtacgacccc aagcgcctct    300
tcggtgtgac cacgctcgac accacgcgcg cggccacctt cctgtcgggc attgctggct    360
cggacccgca gaccaccaac gtccccgtca ttggtggcca ctcgggtgtg accattgtgc    420
ccctgatctc gcaggccgcc cagggtgaca aggtgcaggc tggcgagcag tacgacaagc    480
ttgtgcaccg catccagttc ggtggtgacg aggtcgtcaa ggccaaggac ggtgccggct    540
cggcgacgct ctcgatggcc tacgccgccg ctgtcttcac cgagggcctg ctcaagggtc    600
tcgacggtga ggcggtgacg cagtgcacct tcgtcgagag ccccctgttc aaggaccagg    660
tcgacttctt cgcctcgccc gtcgagttcg gccccgaggg tgtgaagaac atccctgctc    720
tgccgaagct caccgccgag gagcagaagc tgctcgacgc ctgcctgccc gaccttgcca    780
agaacatcaa gaagggcgtt gcgtgggccg ccgagaaccc gtaaatgcgc aaagcaatct    840
tttacggagc ttgcgcgaag gaaaggaaat gtacgtttct atagaacgta gatctgtccc    900
tttccaccta aaaaaaaaaa aaaaaaaaaa aaaaaaaaa                            940

<210> SEQ ID NO 7
<211> LENGTH: 306
<212> TYPE: DNA
<213> ORGANISM: Malassezia furfur
<220> FEATURE:
<221> NAME/KEY: misc_feature
<222> LOCATION: (1)..(306)
<223> OTHER INFORMATION: Strandedness:double-Topology:linear-Molecule
      Type:cDNA to mRNA

<400> SEQUENCE: 7
gaagtggtgt acaagccgga ctcgcagtcc acggacgagt tcatcgtcat cgtcaacccc    60
gactcgtacc agtcgtggcg ctcgggcaac cgcaccatcc cgctcgcgga tgtcgtcgac    120
tccttccaca tctaccactc gggccagggc agccagggca tcctcggcca ggtgtcgaag    180
cagcagctcg actccgtgtt cggtaccgcg aaggaggacg aggcggtgat cctcatcctc    240
gagcgcggcc acctccagca cggcaaaatg cgtggccacg acaagtcggg ccgcaacagc    300
tcgcgc                                                                306

<210> SEQ ID NO 8
<211> LENGTH: 176
<212> TYPE: PRT
<213> ORGANISM: Malassezia furfur

<400> SEQUENCE: 8

Pro Gly Asp Pro Thr Ala Thr Ala Lys Gly Asn Glu Ile Pro Asp
                5                  10                  15

Thr Leu Met Gly Tyr Ile Pro Trp Thr Pro Glu Leu Asp Ser Gly
               20                  25                  30

Glu Val Cys Gly Ile Pro Thr Thr Phe Lys Thr Arg Asp Glu Trp
               35                  40                  45

Lys Gly Lys Lys Val Val Ile Val Ser Ile Pro Gly Ala Tyr Thr
               50                  55                  60

Pro Ile Cys His Gln His Ile Pro Leu Val Lys Arg Val
               65                  70                  75

Asp Glu Leu Lys Ala Lys Gly Val Asp Ala Val Tyr Val Ile Ala
               80                  85                  90

Ser Asn Asp Pro Phe Val Met Ala Ala Trp Gly Asn Phe Asn Asn
```

```
                  95                  100                 105
Ala Lys Asp Lys Val Val Phe Ala Thr Asp Ile Asp Leu Ala Phe
            110                 115                 120

Ser Lys Ala Leu Gly Ala Thr Ile Asp Leu Ser Ala Lys His Phe
            125                 130                 135

Gly Glu Arg Thr Ala Arg Tyr Ala Leu Ile Ile Asp Asp Asn Lys
            140                 145                 150

Ile Val Asp Phe Ala Ser Asp Glu Gly Asp Thr Gly Lys Leu Gln
            155                 160                 165

Asn Ala Ser Ile Asp Thr Ile Leu Thr Lys Val
            170                 175

<210> SEQ ID NO 9
<211> LENGTH: 166
<212> TYPE: PRT
<213> ORGANISM: Malassezia furfur

<400> SEQUENCE: 9

Glu Ile Gly Ser Thr Ile Pro Asn Ala Thr Phe Ala Tyr Val Pro
                  5                  10                  15

Tyr Ser Pro Glu Leu Glu Asp His Lys Val Cys Gly Met Pro Thr
            20                  25                  30

Ser Phe Gln Ser His Glu Arg Trp Lys Gly Lys Lys Val Val Ile
            35                  40                  45

Val Ala Val Pro Gly Ala Phe Thr Pro Thr Cys Thr Ala Asn His
            50                  55                  60

Val Pro Pro Tyr Val Glu Lys Ile Gln Glu Leu Lys Ser Lys Gly
            65                  70                  75

Val Asp Glu Val Val Val Ile Ser Ala Asn Asp Pro Phe Val Leu
            80                  85                  90

Ser Ala Trp Gly Ile Thr Glu His Ala Lys Asp Asn Leu Thr Phe
                  95                  100                 105

Ala Gln Asp Val Asn Cys Glu Phe Ser Lys His Phe Asn Ala Thr
            110                 115                 120

Leu Asp Leu Ser Ser Lys Gly Met Gly Leu Arg Thr Ala Arg Tyr
            125                 130                 135

Ala Leu Ile Ala Asn Asp Leu Lys Val Glu Tyr Phe Gly Ile Asp
            140                 145                 150

Glu Gly Glu Pro Lys Gln Ser Ser Ala Ala Thr Val Leu Ser Lys
            155                 160                 165

Leu

<210> SEQ ID NO 10
<211> LENGTH: 206
<212> TYPE: PRT
<213> ORGANISM: Malassezia furfur

<400> SEQUENCE: 10

Gly Asn Val Met Thr Glu Tyr Thr Leu Pro Pro Leu Pro Tyr Ala
                  5                  10                  15

Tyr Asp Ala Leu Glu Pro Phe Ile Ser Lys Glu Ile Met Thr Val
            20                  25                  30

His His Asp Lys His His Gln Thr Tyr Val Asn Asn Leu Asn Ala
            35                  40                  45

Ala Glu Lys Ala Tyr Ala Glu Ala Thr Ala Asn Asp Val Leu
            50                  55                  60
```

-continued

```
Lys Gln Ile Gln Leu Gln Ser Ala Ile Lys Phe Asn Gly Gly
            65                  70                  75

His Ile Asn His Ser Leu Phe Trp Lys Asn Leu Ala Pro Gln Ser
            80                  85                  90

Glu Gly Gly Gly Gln Leu Asn Asp Gly Pro Leu Lys Gln Ala Ile
            95                 100                 105

Glu Gln Glu Phe Gly Asp Phe Glu Lys Phe Lys Thr Thr Phe Asn
           110                 115                 120

Thr Lys Ala Ala Gly Ile Gln Gly Ser Gly Trp Leu Trp Leu Gly
           125                 130                 135

Val Ala Pro Thr Gly Asn Leu Asp Leu Val Val Ala Lys Asp Gln
           140                 145                 150

Asp Pro Leu Thr Thr His His Pro Val Ile Gly Trp Asp Gly Trp
           155                 160                 165

Glu His Ala Trp Tyr Leu Gln Tyr Lys Asn Asp Lys Ala Ser Tyr
           170                 175                 180

Leu Lys Ala Trp Trp Asn Val Val Asn Trp Ala Glu Ala Glu Lys
           185                 190                 195

Arg Phe Leu Glu Gly Lys Lys Lys Ala Gln Leu
           200                 205

<210> SEQ ID NO 11
<211> LENGTH: 224
<212> TYPE: PRT
<213> ORGANISM: Malassezia furfur

<400> SEQUENCE: 11

Met Phe Thr Leu Ala Thr Arg Arg Ala Ala Ala Pro Leu Ala
             5                  10                  15

Asn Ala Ala Gln Met Gly Val Arg Thr Lys Tyr Thr Leu Pro Pro
            20                   25                  30

Leu Pro Tyr Asp Tyr Gly Ala Leu Glu Pro Ala Ile Ser Gly Glu
            35                   40                  45

Ile Met Glu Thr His Tyr Glu Lys His Arg Thr Tyr Val Asn
            50                   55                  60

Asn Leu Asn Ala Ala Glu Asp Lys Leu Ile Asp Ala Leu Pro Gln
            65                   70                  75

Gln Ser Pro Leu Gly Glu Ile Ala Gln Leu Asn Ala Ile Lys Phe
            80                   85                  90

Asn Gly Gly Gly His Ile Asn His Ser Leu Phe Trp Lys Asn Leu
            95                  100                 105

Ala Pro Thr Asn Lys Gly Gly Gly Glu Leu Asp Ser Gly Glu Leu
           110                 115                 120

Arg Ser Ala Ile Asp Arg Asp Phe Gly Ser Val Asp Ala Met Lys
           125                 130                 135

Glu Lys Phe Asn Ala Ala Leu Ala Gly Ile Gln Gly Ser Gly Trp
           140                 145                 150

Gly Trp Leu Gly Leu Asn Pro Thr Thr Gln Lys Leu Asp Ile Ile
           155                 160                 165

Thr Thr Ala Asn Gln Asp Pro Leu Leu Ser His Lys Pro Leu Ile
           170                 175                 180

Gly Ile Asp Ala Trp Glu His Ala Phe Tyr Leu Gln Tyr Lys Asn
           185                 190                 195

Val Lys Ala Asp Tyr Phe Lys Ala Ile Trp Thr Val Ile Asn Phe
```

Glu Glu Ala Glu Lys Arg Leu Lys Glu Ala Leu Ala Lys Asn
                    215                 220

<210> SEQ ID NO 12
<211> LENGTH: 507
<212> TYPE: PRT
<213> ORGANISM: Malassezia furfur

<400> SEQUENCE: 12

Leu Ser Ser Val Leu Lys Arg Ser Pro Gln Leu Ser Thr Lys Ala
                 5                  10                  15

Leu Lys Gln Pro Leu Thr Leu Pro Arg Leu Leu Pro Ile Gly Ala
                20                  25                  30

Thr Pro Leu Ala Arg Gly Tyr Ala Ser Ser Glu Pro Tyr Asp
                35                  40                  45

Val Ile Val Ile Gly Gly Pro Gly Gly Tyr Val Ala Ala Ile
                50                  55                  60

Lys Ala Ala Gln Gly Gly Leu Lys Thr Ala Cys Val Glu Lys Arg
                65                  70                  75

Gly Ala Leu Gly Gly Thr Cys Leu Asn Val Gly Cys Ile Pro Ser
                80                  85                  90

Lys Ser Leu Leu Asn Asn Ser His Ile Tyr His Gln Thr Gln His
                95                  100                 105

Asp Leu Lys Asn Arg Gly Ile Asp Val Gly Asp Ile Lys Leu Asn
                110                 115                 120

Leu Pro Gln Met Leu Lys Ala Lys Glu Ser Ser Val Thr Ala Leu
                125                 130                 135

Thr Lys Gly Val Glu Gly Leu Phe Lys Lys Asn Lys Val Asp Tyr
                140                 145                 150

Ile Lys Gly Thr Ala Ser Phe Ala Ser Pro Thr Thr Val Asp Val
                155                 160                 165

Lys Leu Asn Asp Gly Gly Glu Gln Gln Ile Glu Gly Lys Asn Ile
                170                 175                 180

Ile Ile Ala Thr Gly Ser Glu Val Thr Pro Phe Pro Gly Val Glu
                185                 190                 195

Ile Asp Glu Glu Gln Ile Ile Ser Ser Thr Gly Ala Leu Ser Leu
                200                 205                 210

Lys Glu Val Pro Glu Lys Met Val Val Ile Gly Gly Gly Val Ile
                215                 220                 225

Gly Leu Glu Leu Gly Ser Val Trp Thr Arg Leu Gly Ala Lys Val
                230                 235                 240

Thr Val Val Glu Phe Gln Glu Ala Ile Gly Gly Pro Gly Leu Asp
                245                 250                 255

Ser Glu Val Ser Gln Gln Phe Lys Lys Leu Leu Glu Lys Gln Gly
                260                 265                 270

Ile His Phe Lys Leu Gly Thr Lys Val Asn Gly Ile Glu Lys Glu
                275                 280                 285

Asn Gly Lys Val Thr Val Arg Thr Glu Gly Lys Asp Gly Lys Glu
                290                 295                 300

Gln Asp Tyr Asp Ala Asn Val Val Leu Val Ser Ile Gly Arg Arg
                305                 310                 315

Pro Val Thr Lys Gly Leu Asn Leu Glu Ala Ile Gly Val Glu Leu
                320                 325                 330

```
Asp Lys Lys Gly Arg Val Val Asp Glu Phe Asn Thr Thr
            335                 340                 345

Cys Lys Gly Val Lys Cys Ile Gly Asp Ala Thr Phe Gly Pro Met
            350                 355                 360

Leu Ala His Lys Ala Glu Asp Glu Gly Ile Ala Val Ala Glu Met
            365                 370                 375

Leu Ala Thr Gly Tyr Gly His Val Asn Tyr Asp Val Ile Pro Ala
            380                 385                 390

Val Ile Tyr Thr His Pro Glu Ile Ala Trp Val Gly Lys Ser Glu
            395                 400                 405

Gln Glu Leu Lys Asn Glu Gly Val Gln Tyr Lys Val Gly Lys Phe
            410                 415                 420

Pro Phe Leu Ala Asn Ser Arg Ala Lys Thr Asn Val Asp Thr Asp
            425                 430                 435

Gly Phe Val Lys Phe Leu Val Glu Lys Glu Thr Asp Lys Ile Leu
            440                 445                 450

Gly Val Phe Ile Ile Gly Pro Asn Ala Gly Glu Met Ile Ala Glu
            455                 460                 465

Ala Gly Leu Ala Met Glu Tyr Gly Ala Ser Ala Glu Asp Val Ala
            470                 475                 480

Arg Thr Cys His Ala His Pro Thr Leu Ser Glu Ala Phe Lys Glu
            485                 490                 495

Gly Ala Met Ala Ala Tyr Ser Lys Pro Ile His Phe
            500                 505

<210> SEQ ID NO 13
<211> LENGTH: 273
<212> TYPE: PRT
<213> ORGANISM: Malassezia furfur

<400> SEQUENCE: 13

Asp Leu Ser His Ile Asn Thr Pro Ala Val Thr Ser Gly Tyr Ala
            5                   10                  15

Gln Asp Asp Leu Glu Gly Ala Val Asp Gly Ala Glu Ile Val Leu
            20                  25                  30

Ile Pro Ala Gly Met Pro Arg Lys Pro Gly Met Thr Arg Asp Asp
            35                  40                  45

Leu Phe Asn Ser Asn Ala Ser Ile Val Arg Asp Leu Ala Lys Val
            50                  55                  60

Val Ala Lys Val Ala Pro Lys Ala Tyr Ile Gly Val Ile Ser Asn
            65                  70                  75

Pro Val Asn Ser Thr Val Pro Ile Val Ala Glu Val Phe Lys Lys
            80                  85                  90

Ala Gly Val Tyr Asp Pro Lys Arg Leu Phe Gly Val Thr Thr Leu
            95                  100                 105

Asp Thr Thr Arg Ala Ala Thr Phe Leu Ser Gly Ile Ala Gly Ser
            110                 115                 120

Asp Pro Gln Thr Thr Asn Val Pro Val Ile Gly Gly His Ser Gly
            125                 130                 135

Val Thr Ile Val Pro Leu Ile Ser Gln Ala Ala Gln Gly Asp Lys
            140                 145                 150

Val Gln Ala Gly Glu Gln Tyr Asp Lys Leu Val His Arg Ile Gln
            155                 160                 165

Phe Gly Gly Asp Glu Val Val Lys Ala Lys Asp Gly Ala Gly Ser
            170                 175                 180
```

```
Ala Thr Leu Ser Met Ala Tyr Ala Ala Ala Val Phe Thr Glu Gly
            185                 190                 195

Leu Leu Lys Gly Leu Asp Gly Glu Ala Val Thr Gln Cys Thr Phe
            200                 205                 210

Val Glu Ser Pro Leu Phe Lys Asp Gln Val Asp Phe Phe Ala Ser
            215                 220                 225

Pro Val Glu Phe Gly Pro Glu Gly Val Lys Asn Ile Pro Ala Leu
            230                 235                 240

Pro Lys Leu Thr Ala Glu Glu Gln Lys Leu Leu Asp Ala Cys Leu
            245                 250                 255

Pro Asp Leu Ala Lys Asn Ile Lys Lys Gly Val Ala Trp Ala Ala
            260                 265                 270

Glu Asn Pro

<210> SEQ ID NO 14
<211> LENGTH: 102
<212> TYPE: PRT
<213> ORGANISM: Malassezia furfur

<400> SEQUENCE: 14

Glu Val Val Tyr Lys Pro Asp Ser Gln Ser Thr Asp Glu Phe Ile
              5                  10                  15

Val Ile Val Asn Pro Asp Ser Tyr Gln Ser Trp Arg Ser Gly Asn
             20                  25                  30

Arg Thr Ile Pro Leu Ala Asp Val Val Asp Ser Phe His Ile Tyr
             35                  40                  45

His Ser Gly Gln Gly Ser Gln Gly Ile Leu Gly Gln Val Ser Lys
             50                  55                  60

Gln Gln Leu Asp Ser Val Phe Gly Thr Ala Lys Glu Asp Glu Ala
             65                  70                  75

Val Ile Leu Ile Leu Glu Arg Gly His Leu Gln His Gly Lys Met
             80                  85                  90

Arg Gly His Asp Lys Ser Gly Arg Asn Ser Ser Arg
             95                 100

<210> SEQ ID NO 15
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Strandedness:single-Topology:linear
<220> FEATURE:
<221> NAME/KEY: Unsure
<222> LOCATION: (1)..(23)
<223> OTHER INFORMATION: any n=a,t,c,g, unknown or other

<400> SEQUENCE: 15
ccnggngayc cnacngcnac ngc                                              23

<210> SEQ ID NO 16
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

```
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 16
acnytnatgg gntayathcc ntggac                                        26

<210> SEQ ID NO 17
<211> LENGTH: 599
<212> TYPE: DNA
<213> ORGANISM: Malassezia furfur
<220> FEATURE:
<221> NAME/KEY: misc_feature
<222> LOCATION: (1)..(599)
<223> OTHER INFORMATION: Strandedness:double-Topology:linear-Molecule
      Type:cDNA to mRNA

<400> SEQUENCE: 17
acactgatgg gatacattcc ctggaccccg gagctcgact cgggtgaggt gtgtggtatc    60
ccccaccacc ttccaagacc cgcgacgagt ggaagggcaa gaaggttgtg attgtctcga   120
tcccgggtgc ctacaccccc atctgtccac cagcagaaca tcccccgct  ttgtgaagcg   180 tgtggatgag ctcaaggcca agggtgtccc gacgccgtgt acgtcattgc gtcgaacgac   240
cccttcgtca tggctgcctg gggccaactt caacaacgcc aaggacaagg tcgtctttgg   300
caccgacatt gacctggcct ctcccaagg  ctctcggcgc gacgatccga cctgagcgcc   360
aagcactttg gtgagcgcac ggcccgctac gctctgatca ttgacgacaa caagattgtc   420
gactttggtt cggacgaggg cgacactggc aagctccaga acgcgtcgat cgacacgatc   480
ctcaccaagg tcttaaaatt ggcgcatgtg cgttgtggtg accactacct aaagggtccg   540
tagagttcca agtcaagtcg tatattttta atttaaaaaa aaaaaaaaa  aaaaaaaaa   599

<210> SEQ ID NO 18
<211> LENGTH: 991
<212> TYPE: DNA
<213> ORGANISM: Malassezia furfur
<220> FEATURE:
<221> NAME/KEY: misc_feature
<222> LOCATION: (1)..(991)
<223> OTHER INFORMATION: Strandedness:double-Topology:linear-Molecule
      Type: genomic DNA

<400> SEQUENCE: 18
agacagcagg gacatggttt agaagcacaa ttcgcggtag ctggcgctga agcgatactc    60
gctgagaaat tcactttccc cccgctgacg gccagacccc cgaactgtcc cgaattacca   120
agcaaatgca cgtgacgttt gtggaggctc ggggattatc aggccacgta tcagtgagcc   180
gagcaccgcg tggcttcggc tggctgcata taaagcccgg tgggccgtgc tcacagcttc   240
atcttccacg acaatcatta tgcctggtgt aggtaccgcg aagtgacacg catgctgacc   300
atcaggatcc tactgctact gccaagggta acgagatccc cgacaccctc atgggctaca   360 tccctggac  cccggagctc gactcgggtg aggtgtgtgg tatccccacc accttcaaga   420
cccgcgacga gtggaaggc  aagaaggttg tgattgtctc gatcccgggt gcctacaccc   480
ccatctgcca ccagcagcac atcccccgc  ttgtgaagcg tgtggatgag ctcaaggcca   540
agggtgtcga cgccgtgtac gtcattgcgt cgaacgaccc cttcgtcatg gtatgtact   600 gctctgtcat ttctttatgc taaccgacag ctgcctgggg caacttcaac aacgccaagg   660
```

-continued

```
acaaggtcgt ctttgccacc gacattgacc tggccttctc caaggctctc ggcgcgacga    720
tcgacctgag cgccaagcac tttggtgagc gcacggcccg ctacgctctg atcattgacg    780
acaacaagat tgtcgacttt gcttcggacg agggcgacac tggcaagctc cagaacgcgt    840
cgatcgacac gatcctcacc aaggtctaaa atggcgcatg tgcgttgtgt gaccactacc    900
taaagggtcc gtagagttcc aagtcaagtc gtatattttt tttttacagg atggtgtgta    960
ctgccacctg cctttgagca aggcgtgcca g                                   991
```

<210> SEQ ID NO 19
<211> LENGTH: 177
<212> TYPE: PRT
<213> ORGANISM: Malassezia furfur

<400> SEQUENCE: 19

```
Met Pro Gly Asp Pro Thr Ala Thr Ala Lys Gly Asn Glu Ile Pro
                 5                  10                  15

Asp Thr Leu Met Gly Tyr Ile Pro Trp Thr Pro Glu Leu Asp Ser
             20                  25                  30

Gly Glu Val Cys Gly Ile Pro Thr Thr Phe Lys Thr Arg Asp Glu
         35                  40                  45

Trp Lys Gly Lys Val Val Ile Val Ser Ile Pro Gly Ala Tyr
     50                  55                  60

Thr Pro Ile Cys His Gln Gln His Ile Pro Pro Leu Val Lys Arg
 65                  70                  75

Val Asp Glu Leu Lys Ala Lys Gly Val Asp Ala Val Tyr Val Ile
                 80                  85                  90

Ala Ser Asn Asp Pro Phe Val Met Ala Ala Trp Gly Asn Phe Asn
             95                 100                 105

Asn Ala Lys Asp Lys Val Val Phe Ala Thr Asp Ile Asp Leu Ala
        110                 115                 120

Phe Ser Lys Ala Leu Gly Ala Thr Ile Asp Leu Ser Ala Lys His
    125                 130                 135

Phe Gly Glu Arg Thr Ala Arg Tyr Ala Leu Ile Ile Asp Asp Asn
140                 145                 150

Lys Ile Val Asp Phe Ala Ser Asp Glu Gly Asp Thr Gly Lys Leu
                155                 160                 165

Gln Asn Ala Ser Ile Asp Thr Ile Leu Thr Lys Val
            170                 175
```

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Strandedness:single-Topology:linear
<220> FEATURE:
<221> NAME/KEY: Unsure
<222> LOCATION: (1)..(25)
<223> OTHER INFORMATION: any n=a,t,c,g, unknown or other

<400> SEQUENCE: 20

```
acnttygcnc argaygtnaa ytgyg                                           25
```

<210> SEQ ID NO 21
<211> LENGTH: 261

```
<212> TYPE: DNA
<213> ORGANISM: Malassezia furfur
<220> FEATURE:
<221> NAME/KEY: misc_feature
<222> LOCATION: (1)..(599)
<223> OTHER INFORMATION: Strandedness:double-Topology:linear-Molecule
      Type:cDNA to mRNA

<400> SEQUENCE: 21
acctttgcac aggacgtcaa ttgcgagttc tccaagcact ttaacgcgac gctggacctg    60
tcgtcgaagg gcatgggcct gcgcaccgcg cgctacgcgc tgatcgcgaa cgacctcaag   120
gtcgagtact ttggcatcga cgagggcgag ccgaagcagt cgtcggccgc gacggtgctg   180
agcaagctgt agtgccgttc tacttagtca aacaatcggg tatagtcgcg ttggaaaaaa   240
aaaaaaaaaa aaaaaaaaaa a                                             261

<210> SEQ ID NO 22
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 22
caracntayg tnaayaayyt naaygc                                         26

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(25)
<223> OTHER INFORMATION: Strandedness:single-Topology:linear
<220> FEATURE:
<221> NAME/KEY: Unsure
<222> LOCATION: (1)..(25)
<223> OTHER INFORMATION: any n=a,t,c,g, unknown or other

<400> SEQUENCE: 23
acncaycayc cngtnathgg ntggg                                          25

<210> SEQ ID NO 24
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 24
atnacnggrt grtgngtngt narngg                                         26
```

<210> SEQ ID NO 25
<211> LENGTH: 371
<212> TYPE: DNA
<213> ORGANISM: Malassezia furfur
<220> FEATURE:
<221> NAME/KEY: misc_feature
<222> LOCATION: (1)..(371)
<223> OTHER INFORMATION: Strandedness:double-Topology:linear-Molecule
      Type:cDNA to mRNA

<400> SEQUENCE: 25

```
cagacctatg tcaacaacct gaacgccgcc gagaaggcgt acgctgaggc gacggccgcg      60
aacgacgtgc ttaagcagat ccagctgcag agtgcgatca agttcaacgg cggtggccac    120
atcaaccact cgctgttctg gaagaacctg gcccccagagcgagggtgg tggccaactg     180
aacgatggcc ctctcaagca ggccatcgag caggagttcg gcgactttga gaaattcaag    240
acgaccttca acacgaaggc ggccggcatc cagggttcgg gctggctgtg gctcggtgtt    300
gccccgacgg gcaacctcga cctggtcgtt gccaaggacc aggacccgct gaccacccat    360
caccccgtga t                                                         371
```

<210> SEQ ID NO 26
<211> LENGTH: 263
<212> TYPE: DNA
<213> ORGANISM: Malassezia furfur
<220> FEATURE:
<221> NAME/KEY: misc_feature
<222> LOCATION: (1)..(263)
<223> OTHER INFORMATION: Strandedness:double-Topology:linear-Molecule
      Type:cDNA to mRNA

<400> SEQUENCE: 26

```
acgcatcatc ccgtgattgg ctgggatggc tgggagcacg cctggtacct gcagtacaag      60
nacgacaagg cttcctacct taaggcctgg tggaacgtgg tgaactgggc cgaggccgag    120
aagcgcttcc tcgagggtaa gaagaaggcc cagctgtaat ggcacgtttg tagatgatga    180
acgacacacg attttaggtc gccaaaaaaa aaaaaaaaa aaaaaaaaaa aaaaaaaaaa      240
aaaaaaaaaa aaaaaaaaaa aaa                                            263
```

<210> SEQ ID NO 27
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 27

```
ccnccnytnc cntaygayta yggngc                                          26
```

<210> SEQ ID NO 28
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:

```
<221> NAME/KEY: misc_feature
<222> LOCATION: (1)..(28)
<223> OTHER INFORMATION: Strandedness:single-Topology:linear
<220> FEATURE:
<221> NAME/KEY: Unsure
<222> LOCATION: (1)..(28)
<223> OTHER INFORMATION: any n=a,t,c,g, unknown or other

<400> SEQUENCE: 28
garccngcna thwsnggnga rathatgg                                    28

<210> SEQ ID NO 29
<211> LENGTH: 630
<212> TYPE: DNA
<213> ORGANISM: Malassezia furfur
<220> FEATURE:
<221> NAME/KEY: misc_feature
<222> LOCATION: (1)..(630)
<223> OTHER INFORMATION: Strandedness:double-Topology:linear-Molecule
      Type:cDNA to mRNA

<400> SEQUENCE: 29
gaacctgctt tctgggggga gataatggag acgcactacg agaagcacca ccgcacctac     60
gtcaacaacc tgaacgccgc ggaggacaag ctgatcgacg cgctcccgca gcagagcccg    120
ctcggcgaga ttgcgcagct gaacgcgatc aanttcatcg gcggtggcca catcaaccac    180
tcgctcttct ggaagaacct cgcgccgacg aacaagggcg gcggcgagct cgactcgggc    240
gagctgcgct ccgcgatcga ccgcgacttt ggctcggtcg acgccatgaa ggagaagttc    300
aacgcggcgc tcgcgggcat ccagggtatc ggctggggct ggctcggcct gaaccccacg    360
acgcagaagc tcgacatcat cacgaccgcg aaccaggacc cgctcctgtc gcacaagccg    420
ctgattggca tcgatgcgtg ggagcacgcg tactacctgc agtacaagaa cgtcaaggcc    480
gactacttca aggcgatctg gaccgtgatc aactttgagg aggccgagaa gcgtctcang    540
gaggcgctcg ccaagaacta gacacgttcg gtttttttttt tatcactagc ttagcaatga    600
cctgcccacg ctaaaaaaaa aaaaaaaaaa                                     630

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Strandedness:single-Topology:linear
<220> FEATURE:
<221> NAME/KEY: Unsure
<222> LOCATION: (1)..(23)
<223> OTHER INFORMATION: any n denotes inosine

<400> SEQUENCE: 30
ggntaygtng cngcnathaa rgc                                            23

<210> SEQ ID NO 31
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Strandedness:single-Topology:linear
<220> FEATURE:
```

```
<221> NAME/KEY: Unsure
<222> LOCATION: (1)..(23)
<223> OTHER INFORMATION: any n denotes inosine

<400> SEQUENCE: 31
tcytcngcyt trtgngcnar cat                                              23

<210> SEQ ID NO 32
<211> LENGTH: 938
<212> TYPE: DNA
<213> ORGANISM: Malassezia furfur
<220> FEATURE:
<221> NAME/KEY: misc_feature
<222> LOCATION: (1)..(938)
<223> OTHER INFORMATION: Strandedness:double-Topology:linear-Molecule
      Type:cDNA to mRNA

<400> SEQUENCE: 32
gggtncgtgg cggcgataaa ggccgcgcag ggtggtctga agactgcatg tgttgagaag        60
cgcggtgcgc ttggtggtac ctgcttgaac gtgggctgta tcccttccaa gtcgttggtg       120
aacaactcgc acatcttcca ccagacgcag cacgacctca agaaccgcgg tattgacgtc       180
agcgaggtca agttgancct gccgcagatg ctcaaggcga aggagagctc ggtcactgcg       240
ctcaccaagg gtgtcgaggg cctgttcaag aagaacaagg tcgcctacct caaggggaca       300
gacagattcg cgagccctac gacggtggac gtgaagctga gcgatggcgg tgaacagnag       360
attgagggca agaacattat cattgcgact ggctctgagg tgacgccttn ccctggtgtg       420
gagatcgccg aggagcagat tatcagctcg acgggtgcgc tctcgctcaa ggaggtgcct       480
nagaagatgg tcgtgatcgg tggtggtgtg ancgctcttg agctcgntag cgtgtggagc       540
cgtctggncc ccaaggtgac cgtggntgag ttccaggacg cgattgttgc ccccggtctg       600
gacagcgagg tgacccagca gttcaagaag ctgctcgaga agcagggcat ccagttcaag       660
cttgccacta aggtgaacgg gattgagaag caggatgcca aagtgatggt ccgcaccgag       720
ggcaaggacg gcaaggagca ggacnacgac gccaacgttg tgctcgtgtc catcggtcnc       780
cncccggtga cgaagggctt gaacctcgag gcgatcggcg ttgagcttga taagaaggcc       840
cgcgtggtgg tggacgatga gttcaacacg acgtgcaagg gtgtcaagtg cattggtgac       900
gcgacgttcg gccctatgct cgcccacaag gccgaaga                              938

<210> SEQ ID NO 33
<211> LENGTH: 1600
<212> TYPE: DNA
<213> ORGANISM: Malassezia furfur
<220> FEATURE:
<221> NAME/KEY: misc_feature
<222> LOCATION: (1)..(1600)
<223> OTHER INFORMATION: Strandedness:double-Topology:linear-Molecule
      Type:cDNA to mRNA

<400> SEQUENCE: 33
gttgagctct gtgctgaagc gctcgccgca gctctctact aaggctctga agcagccgct        60
tacgctcccg cgtctgctgc ccattggtgc tgcgccgctg gctcgtggct atgcctcgag       120
ctcggagcca tacgatgtca ttgtgattgg tggtggcccc ggtggctacg tggccgcgat       180
caaggccgcg cagggtggtc tgaagactgc atgtgttgag aagcgcggtg cgcttggtgg       240
tacctgcttg aacgtgggct gtatcccttc caagtcgttg ctgaacaact cgcacatctt       300
ccaccagacg cagcacgacc tcaagaaccg cggtattgac gtcagcgagg tcaagttgaa       360
cctgccgcag atgctcaagg cgaaggagag ctcggtcact gcgctcacca aggtgtcga       420
```

```
gggcctgttc aagaagaaca aggtcgacta cctcaagggc acagccagct tcgcgagccc      480
tacgacggtg acgtgaagc tgaacgatgg cggtgaacag cagattgagg gcaagaacat      540
tatcattgcg actggctctg aggtgacgcc cttccctggt gtggagatcg acgaggagca     600
gattatcagc tcgacgggtg cgctctcgct caaggaggtg cctgagaaga tggtcgtgat     660
cggtggtggt gtgatcggtc tggagctcgg tagcgtgtgg agccgtctgg cgccaaggt      720 gaccgtggtt gagttccagg acgcgattgg tggccccggt ctggacagcg aggtgagcca     780
gcagttcaag aagctgctcg agaagcaggg catccagttc aagcttggca ctaaggtgaa     840
cgggattgag aagcaggatg gcaaagtgat ggtccgcacc gagggcaaag acggcaagga     900
gcaggactac gacgccaacg ttgtgctcgt gtccatcggt cgccgcccgg tgacgaaggg     960
cttgaacctc gaggcgatcg cgttgagct tgataagaag ggccgcgtgg tggtggacga    1020
tgagttcaac acgacgtgca agggtgtcaa gtgcattggt gacgcgacgt tcggccctat    1080
gcttgcgcac aaggccgagg acgagggtat cgccgttgct gagatgctcg cgaccggcta    1140
cggccacgtc aactacgacg tgatccctgc ggtgatctac acgcaccccg agattgcgtg    1200
ggtcggcaag tcggagcagg agctcaagaa cgatggcgtg cagtacaagg tgggcaagtt    1260
ccccttcctg gccaactcgc gtgctaagac caacgtcgac accgacggtt ttgtcaagtt    1320
cctcgtggag aaggacaccg acaagattct cggcgtgttc atcatcggtc gaacgccgg     1380 cgagatgatt gccgaggctg gcctggctat ggagtacggt gcgagtgcag aggatgtcgc    1440
gcgcacctgc cacgcgcacc cgacgctctc ggaggccttc aaggagggtg cgatggccgc    1500
ctactcgaag ccgattcact tttgatttcg taggtttccc ccgataggcg cccgatacgt    1560
cttcctcaaa aaaaaaaaaa aaaaaaaaaa aaaaaaaaa                           1600
```

<210> SEQ ID NO 34
<211> LENGTH: 507
<212> TYPE: PRT
<213> ORGANISM: Malassezia furfur

<400> SEQUENCE: 34

Leu Ser Ser Val Leu Lys Arg Ser Pro Gln Leu Ser Thr Lys Ala
                5                  10                  15

Leu Lys Gln Pro Leu Thr Leu Pro Arg Leu Leu Pro Ile Gly Ala
            20                  25                  30

Ala Pro Leu Ala Arg Gly Tyr Ala Ser Ser Glu Pro Tyr Asp
        35                  40                  45

Val Ile Val Ile Gly Gly Gly Pro Gly Gly Tyr Val Ala Ala Ile
    50                  55                  60

Lys Ala Ala Gln Gly Gly Leu Lys Thr Ala Cys Val Glu Lys Arg
65                  70                  75

Gly Ala Leu Gly Gly Thr Cys Leu Asn Val Gly Cys Ile Pro Ser
            80                  85                  90

Lys Ser Leu Leu Asn Asn Ser His Ile Phe His Gln Thr Gln His
        95                 100                 105

Asp Leu Lys Asn Arg Gly Ile Asp Val Ser Glu Val Lys Leu Asn
           110                 115                 120

Leu Pro Gln Met Leu Lys Ala Lys Glu Ser Ser Val Thr Ala Leu
           125                 130                 135

Thr Lys Gly Val Glu Gly Leu Phe Lys Lys Asn Lys Val Asp Tyr
           140                 145                 150

-continued

```
Leu Lys Gly Thr Ala Ser Phe Ala Ser Pro Thr Thr Val Asp Val
            155                 160                 165
Lys Leu Asn Asp Gly Gly Glu Gln Gln Ile Glu Gly Lys Asn Ile
        170                 175                 180
Ile Ile Ala Thr Gly Ser Glu Val Thr Pro Phe Pro Gly Val Glu
            185                 190                 195
Ile Asp Glu Glu Gln Ile Ile Ser Ser Thr Gly Ala Leu Ser Leu
            200                 205                 210
Lys Glu Val Pro Glu Lys Met Val Val Ile Gly Gly Val Ile
            215                 220                 225
Gly Leu Glu Leu Gly Ser Val Trp Ser Arg Leu Gly Ala Lys Val
            230                 235                 240
Thr Val Val Glu Phe Gln Asp Ala Ile Gly Gly Pro Gly Leu Asp
            245                 250                 255
Ser Glu Val Ser Gln Gln Phe Lys Lys Leu Leu Glu Lys Gln Gly
            260                 265                 270
Ile Gln Phe Lys Leu Gly Thr Lys Val Asn Gly Ile Glu Lys Gln
            275                 280                 285
Asp Gly Lys Val Met Val Arg Thr Glu Gly Lys Asp Gly Lys Glu
            290                 295                 300
Gln Asp Tyr Asp Ala Asn Val Val Leu Val Ser Ile Gly Arg Arg
            305                 310                 315
Pro Val Thr Lys Gly Leu Asn Leu Glu Ala Ile Gly Val Glu Leu
            320                 325                 330
Asp Lys Lys Gly Arg Val Val Asp Asp Glu Phe Asn Thr Thr
            335                 340                 345
Cys Lys Gly Val Lys Cys Ile Gly Asp Ala Thr Phe Gly Pro Met
            350                 355                 360
Leu Ala His Lys Ala Glu Asp Glu Gly Ile Ala Val Ala Glu Met
            365                 370                 375
Leu Ala Thr Gly Tyr Gly His Val Asn Tyr Asp Val Ile Pro Ala
            380                 385                 390
Val Ile Tyr Thr His Pro Glu Ile Ala Trp Val Gly Lys Ser Glu
            395                 400                 405
Gln Glu Leu Lys Asn Asp Gly Val Gln Tyr Lys Val Gly Lys Phe
            410                 415                 420
Pro Phe Leu Ala Asn Ser Arg Ala Lys Thr Asn Val Asp Thr Asp
            425                 430                 435
Gly Phe Val Lys Phe Leu Val Glu Lys Asp Thr Asp Lys Ile Leu
            440                 445                 450
Gly Val Phe Ile Ile Gly Pro Asn Ala Gly Glu Met Ile Ala Glu
            455                 460                 465
Ala Gly Leu Ala Met Glu Tyr Gly Ala Ser Ala Glu Asp Val Ala
            470                 475                 480
Arg Thr Cys His Ala His Pro Thr Leu Ser Glu Ala Phe Lys Glu
            485                 490                 495
Gly Ala Met Ala Ala Tyr Ser Lys Pro Ile His Phe
            500                 505
```

<210> SEQ ID NO 35
<211> LENGTH: 26
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: misc_feature
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 35
aargtngcng tnytnggngc nwsngg                                          26

<210> SEQ ID NO 36
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: Strandedness:single-Topology:linear
<220> FEATURE:
<221> NAME/KEY: Unsure
<222> LOCATION: (1)..(26)
<223> OTHER INFORMATION: any n=a,t,c,g, unknown or other

<400> SEQUENCE: 36
ytnwsnytny tnatgaaryt naaycc                                          26

<210> SEQ ID NO 37
<211> LENGTH: 1009
<212> TYPE: DNA
<213> ORGANISM: Malassezia furfur
<220> FEATURE:
<221> NAME/KEY: misc_feature
<222> LOCATION: (1)..(1009)
<223> OTHER INFORMATION: Strandedness:double-Topology:linear-Molecule
      Type:cDNA to mRNA

<400> SEQUENCE: 37
ttctctctgt tgatgaagct caaccccaag gtcaccgagc tgcgcctgta cgacatccgt      60
cttgctccgg gtgttgctgc ggacctctcg cacatcaaca cgcctgcggt gacctcgggc     120
tacgcccagg acnatcttga gggtgccgtt gacggcgcaa agattgtcct gatccccgcc     180
ggtatgccgc gcaagcccgg catgacccgt gacgatctgt tcaactcgaa cgcctcgatc     240
gtccgtgacc tcgccaagac cgtggccaag gttgccccca aggcctacat tggtatcatc     300
tcgaaccccg tcaactcgac ggtgccgatc gtcgccgagg tgttcaagaa ggcgggtgtg     360
tacgacccca gcgcctctt cggtgtgacc acgctcgaca ccacgcgtgc ggccaccttc     420
ctgtcgggca tcactggctc ggaaccgcag accaccaatg tcccggtcat tggtggtcac     480
tcgggtgtga ccatcgtgcc tctggtctcg caggcccccc agggtgacaa ggtgcaggcc     540
ggcgagcagt acgacaagct cgtccaccgc attcagttcg tggtgacga ggtcgttaag     600 gccaaggacg gtgcgggttc ggcgacgctg tcgatggcct acgccgccgc tgtcttcact     660
gagggcctgc tcaagggtct tgacggtgag gcggtgacgc agtgcacctt cgttgagagc     720 ccctgttca aggaccaggt tgacttcttc gcttcgcccg tcgagttcgg ccccgagggc     780
gtgaagaaca tccctgccct gcccaagctc accgctgagg agcagaagct gntngacgcc     840
tgcctgcccg accttgccaa gaacatcaag aagggtgttg cgtgggttgc cgagaacccc     900
taaatgcgca gaaccagctt ccacggagct tgcgccaagg aaaggaaacg cacatttnta     960
tagagcgtag ctttgtccct ttccattttaa aaaaaaaaaa aaaaaaaa              1009
```

<210> SEQ ID NO 38
<211> LENGTH: 1008
<212> TYPE: DNA
<213> ORGANISM: Malassezia furfur
<220> FEATURE:
<221> NAME/KEY: misc_feature
<222> LOCATION: (1)..(1008)
<223> OTHER INFORMATION: Strandedness:double-Topology:linear-Molecule
      Type:cDNA to mRNA

<400> SEQUENCE: 38

```
ctaagattct tgatgaagct gaaccccaag gttaccgagc tccgcctgta cgacatccgc      60
ctcgctccgg gtgttgctgc ggatctctcg cacatcaaca ccccgcggt gacttcgggc      120
tacgcccagg acgacctcga gggtgccgtc gacggtgcgg agattgtgct gatccccgcc     180
ggtatgccgc gcaagcccgg catgacccgt gacgacctgt tcaactcgaa cgcctcgatt     240
gtccgtgacc tcgccaaggt cgtggctaag gtcgccccaa aggcttacat cggcgtcatc     300
tcgaaccccg tcaactcgac ggtgccgatc gtcgctgagg tgttaaagaa ggccggtgtg     360
tacgacccca agcgcctctt cggtgtgacc acgctcgaca ccacgcgcgc ggccaccttc     420
ctgtcgggca ttgctggctc ggaaccgcag accaccaacg tccccgtcat tggtggccac     480
tcgggtgtga ccattgtgcc cctgatctcg caggccgccc agggtgacaa ggtgcaggct     540
ggcgagcagt acgacaagct tgtgcaccgc atccagttcg gtggtgacga ggtcgtcaag     600
gccaaggacg gtgccggttc ggcgacgctc tcgatggcct acgccgccgc tgttttcacc     660
gagggcctgc ccaagggtct cgacggtgag gcggtgacgc agtgcacctt cgtcgagagc     720
cccctgttca aggaccaggt cganttcttc gcttcgcccg tcgagttcgg ccccgagggt     780
gtgaagaaca tccctgntct gccgaagctc accgccgagg agcagaagct gntngacgcc     840
tgcctgcccg accttgccaa gaacatcaag aagggcgttg cgtgggccgc cgagaacccg     900
taaatgcgca aagcaatntt ttacggagct tgcgcgaagg aaaggaaatg tacgttttnta    960
tagaacgtag atctgtccct ttccacctaa aaaaaaaaa aaaaaaaa                  1008
```

<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(23)
<223> OTHER INFORMATION: Strandedness:single-Topology:linear
<220> FEATURE:
<221> NAME/KEY: Unsure
<222> LOCATION: (1)..(23)
<223> OTHER INFORMATION: any n denotes inosine

<400> SEQUENCE: 39
ggnaayaayg gnytnwsnga rgt                                              23

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: Strandedness:single-Topology:linear

```
<220> FEATURE:
<221> NAME/KEY: Unsure
<222> LOCATION: (1)..(20)
<223> OTHER INFORMATION: any n denotes inosine

<400> SEQUENCE: 40
gargtngtnt ayaarccnga                                                    20

<210> SEQ ID NO 41
<211> LENGTH: 427
<212> TYPE: DNA
<213> ORGANISM: Malassezia furfur
<220> FEATURE:
<221> NAME/KEY: misc_feature
<222> LOCATION: (1)..(427)
<223> OTHER INFORMATION: Strandedness:double-Topology:linear-Molecule
      Type:cDNA to mRNA

<400> SEQUENCE: 41
gaagtggtgt acaagccgga ctcgcagtcc acggacgagt tcatcgtcat cgtcaacccc         60
gactcgtacc agtcgtggcg ctcgggcaac cgcaccatcc cgctcgcgga tgtcgtcgac        120
tccttccaca tctaccactc gggccagggc agccagggca tcctcggcca ggtgtcgaag        180
cagcagctcg actccgtgtt cggtaccgcg aaggaggacg aggcggtgat cctcatcctc        240
gagcgcggcc acctccagca cggcaaaatg cgtggccacg acaagtcggg ccgcaacagc        300
tcgcgctaag ccatagtggt acagtaggta ccgggccccc aaggcccgat gcgggcgctg        360
ccgcctgcta tccaacatga ttgtacctac gtaaaaaaaa aaaaaaaaaa aaaaaaaaaa        420
aaaaaaa                                                                 427

<210> SEQ ID NO 42
<211> LENGTH: 15
<212> TYPE: PRT
<213> ORGANISM: Malassezia furfur

<400> SEQUENCE: 42

Ile Pro Trp Thr Pro Glu Leu Asp Ser Gly Glu Val Cys Gly Ile
                5                  10                  15

<210> SEQ ID NO 43
<211> LENGTH: 15
<212> TYPE: PRT
<213> ORGANISM: Malassezia furfur

<400> SEQUENCE: 43

Ser Lys Ala Leu Gly Ala Thr Ile Asp Leu Ser Ala Lys His Phe
                5                  10                  15

<210> SEQ ID NO 44
<211> LENGTH: 15
<212> TYPE: PRT
<213> ORGANISM: Malassezia furfur

<400> SEQUENCE: 44

Ala Thr Ile Asp Leu Ser Ala Lys His Phe Gly Glu Arg Thr Ala
                5                  10                  15

<210> SEQ ID NO 45
<211> LENGTH: 28
<212> TYPE: PRT
<213> ORGANISM: Malassezia furfur

<400> SEQUENCE: 45
```

```
Pro Gly Asp Pro Thr Ala Thr Ala Lys Gly Asn Glu Ile Pro Asp
                5              10                  15

Thr Leu Met Gly Tyr Ile Pro Trp Thr Pro Glu Leu Asp
            20                  25

<210> SEQ ID NO 46
<211> LENGTH: 12
<212> TYPE: PRT
<213> ORGANISM: Malassezia furfur

<400> SEQUENCE: 46

Val Glu Tyr Phe Gly Ile Asp Glu Gly Glu Pro Lys
                5                   10

<210> SEQ ID NO 47
<211> LENGTH: 13
<212> TYPE: PRT
<213> ORGANISM: Malassezia furfur

<400> SEQUENCE: 47

Asp Asn Leu Thr Phe Ala Gln Asp Val Asn Cys Glu Phe
                5                   10

<210> SEQ ID NO 48
<211> LENGTH: 24
<212> TYPE: PRT
<213> ORGANISM: Malassezia furfur
<220> FEATURE:
<221> NAME/KEY: Unsure
<222> LOCATION: (1)..(24)
<223> OTHER INFORMATION: any Xaa = any amino acid, unknown or other

<400> SEQUENCE: 48

Val Val Ile Val Ala Val Pro Gly Xaa Phe Thr Pro Thr Cys Thr
                5                   10                  15

Ala Asn His Val Pro Xaa Tyr Xaa Glu
            20

<210> SEQ ID NO 49
<211> LENGTH: 20
<212> TYPE: PRT
<213> ORGANISM: Malassezia furfur
<220> FEATURE:
<221> NAME/KEY: Unsure
<222> LOCATION: (1)..(20)
<223> OTHER INFORMATION: any Xaa = any amino acid, unknown or other

<400> SEQUENCE: 49

Asp Gln Asp Pro Leu Thr Thr His His Pro Val Ile Gly Trp Asp
                5                   10                  15

Xaa Xaa Glu His Ala
            20

<210> SEQ ID NO 50
<211> LENGTH: 13
<212> TYPE: PRT
<213> ORGANISM: Malassezia furfur

<400> SEQUENCE: 50

Ala Trp Trp Asn Val Val Asn Trp Ala Glu Ala Glu Lys
                5                   10

<210> SEQ ID NO 51
<211> LENGTH: 12
<212> TYPE: PRT
```

```
<213> ORGANISM: Malassezia furfur
<220> FEATURE:
<221> NAME/KEY: Unsure
<222> LOCATION: (1)..(12)
<223> OTHER INFORMATION: any Xaa = any amino acid, unknown or other

<400> SEQUENCE: 51

Phe Xaa Gly Gly Gly His Ile Asn Xaa Ser Leu Phe
                5                   10

<210> SEQ ID NO 52
<211> LENGTH: 30
<212> TYPE: PRT
<213> ORGANISM: Malassezia furfur

<400> SEQUENCE: 52

Lys Tyr Thr Leu Pro Pro Leu Pro Tyr Asp Tyr Gly Ala Leu Glu
                5                   10                  15

Pro Ala Ile Ser Gly Glu Ile Met Glu Thr His Tyr Glu Lys His
                20                  25                  30

<210> SEQ ID NO 53
<211> LENGTH: 28
<212> TYPE: PRT
<213> ORGANISM: Malassezia furfur
<220> FEATURE:
<221> NAME/KEY: Unsure
<222> LOCATION: (1)..(28)
<223> OTHER INFORMATION: any Xaa = any amino acid, unknown or other

<400> SEQUENCE: 53

Xaa Xaa Xaa Xaa Xaa Glu Pro Tyr Asp Val Ile Val Ile Gly Gly
                5                   10                  15

Gly Pro Gly Gly Tyr Val Ala Xaa Xaa Lys Xaa Xaa Gln
                20                  25

<210> SEQ ID NO 54
<211> LENGTH: 30
<212> TYPE: PRT
<213> ORGANISM: Malassezia furfur

<400> SEQUENCE: 54

Arg Lys Val Ala Val Leu Gly Ala Ser Gly Gly Ile Gly Gln Pro
                5                   10                  15

Leu Ser Leu Leu Met Lys Leu Asn Pro Lys Val Thr Glu Leu Arg
                20                  25                  30

<210> SEQ ID NO 55
<211> LENGTH: 23
<212> TYPE: PRT
<213> ORGANISM: Malassezia furfur
<220> FEATURE:
<221> NAME/KEY: Unsure
<222> LOCATION: (1)..(23)
<223> OTHER INFORMATION: any Xaa = any amino acid, unknown or other

<400> SEQUENCE: 55

Gly Asn Asn Gly Leu Ser Glu Val Val Tyr Lys Pro Asp Xaa Gln
                5                   10                  15

Xaa Thr Xaa Glu Phe Xaa Val Ile
                20

<210> SEQ ID NO 56
<211> LENGTH: 9
<212> TYPE: PRT
```

```
<213> ORGANISM: Malassezia furfur
<220> FEATURE:
<221> NAME/KEY: Unsure
<222> LOCATION: (1)..(9)
<223> OTHER INFORMATION: any Xaa = any amino acid, unknown or other

<400> SEQUENCE: 56

Val Asp Gln Xaa Tyr Phe Gly Leu Xaa
                5

<210> SEQ ID NO 57
<211> LENGTH: 25
<212> TYPE: PRT
<213> ORGANISM: Malassezia furfur

<400> SEQUENCE: 57

Ser Asn Val Phe Phe Asp Ile Thr Lys Asn Gly Ser Pro Leu Gly
                5                   10                  15

Thr Ile Lys Phe Lys Leu Phe Asp Asp Val
                20                  25

<210> SEQ ID NO 58
<211> LENGTH: 14
<212> TYPE: PRT
<213> ORGANISM: Malassezia furfur
<220> FEATURE:
<221> NAME/KEY: Unsure
<222> LOCATION: (1)..(14)
<223> OTHER INFORMATION: any Xaa = any amino acid, unknown or other

<400> SEQUENCE: 58

His His Gln Thr Tyr Val Asn Asn Leu Asn Ala Ala Xaa Lys
                5                   10
```

ANTIGENIC PROTEIN ORIGINATING IN *MALASSEZIA*

This application is a divisional of application Ser. No. 10/109,670 filed on Apr. 1, 2002 now U.S. Pat. No. 6,911,208 which is a Divisional of application Ser. No. 09/091,097 filed on Jun. 12, 1998, now U.S. Pat. No. 6,432,407, and for which priority is claimed under 35 U.S.C. §120. Application Ser. No. 09/091,097 is the national phase of PCT International Application No. PCT/JP96/03602 filed on Dec. 10, 1996 under 35 U.S.C. § 371. The entire contents of each of the above-identified applications are hereby incorporated by reference. This application also claims priority of the following: Application No. 7-346627 filed in Japan on Dec. 12, 1995; Application No. 8-257612 filed in Japan on Sep. 5, 1996; and Application No. 8-257613 filed in Japan on Sep. 5, 1996 under 35 U.S.C. § 119.

TECHNICAL FIELD

The present invention relates to a novel antigenic protein which is isolated and purified from *Malassezia* fungi, useful for diagnosis, treatment, and prophylaxis for allergoses and infectious diseases of which causative microorganisms are *Malassezia* fungi, and to antigenic fragments thereof, an antibody against the antigenic protein or antigenic fragments thereof, and the like.

Further, the present invention relates to a recombinant *Malassezia* antigenic protein, a gene encoding the antigenic protein, and also to an epitope of the protein, and the like.

BACKGROUND ART

As a result of sensitization by the causative antigen for the diseases, in many of the allergoses, an antigen (allergen)-specific IgE antibody (reagin antibody) is produced in sera and tissue. Upon re-exposure to the same antigen, IgE bound to the mast cells or basophiles and the specific allergen become coupled together to cause IgE crosslink on the cell surface, resulting in physiological effects due to the IgE-antigen interaction. Such physiological effects include the release of histamine, serotonin, heparin, eosinophilic chemotactic factor, or various leukotrienes, whereby persisting constriction of bronchial smooth muscle is caused. These released substances act as chemical mediators to induce allergic symptoms due to a coupling of IgE and a particular allergen. The effects of an allergen manifest themselves via these symptoms, and such effects can occur systemically or locally, depending on the route of antigen invasion in the body and the pattern of IgE sedimentation on mast cells or basophiles. Local symptoms generally occur on the epithelial surface at the position of allergen invasion in the body. Systemic effects are consequences of IgE-basophile response to the antigen in the blood vessels, which are typically exemplified by anaphylactic shock. The helper T (Th) cell plays a key role in the series of reactions. Among the various cytokines produced by Th cells activated by antigen stimulation, IL4 promotes IgE production.

A wide variety of substances induce allergic symptoms in humans. To date, allergens have been viewed as an assembly of a large number of substances represented by pollens or house dusts. As a result of recent advances in separation and purification techniques and methods for evaluating allergen activity, it has been clearly obvious that the allergen comprises a single substance or several kinds of principal substances. In particular, a rapid progress in research into allergens of *Cryptomeria japonica* (Japanese cedar) pollen, ticks, cats, and the like has been made, and major allergens, such as Cry j 1 and Cry j 2 have been isolated from *Cryptomeria japonica* pollen; Der f 1, Der f 2, and Der f 3 have been isolated from ticks; and Fel d 1 has been isolated from cats. Furthermore, genes encoding these allergenic proteins have also been isolated, thereby making it possible to prepare pure allergenic proteins in large amounts by genetic engineering techniques.

In the diagnosis of allergoses, it is necessary to first identify the antigen of which the microorganisms are causative, and in order to accomplish this purpose, over 100 kinds of commercially available antigen extracts, and in some cases, those prepared in-house, are first subjected to intracutaneous tests using suspected antigen extracts. In the case where an antigen of which is a very likelihood of being the causative antigen is found, the antigen can be specifically identified by assaying serum IgE antibody titration by RAST method and the like, provocative tests, or histamine release tests using whole blood or lymphocytes. Because these antigen extracts do not have their potency well titrated, however, attention should be marked to the risk of anaphylactogenesis upon use. Usable therapies for allergoses include antihistaminics, steroidal anti-inflammatory drugs, and mediator release suppressors, and the therapy of hyposensitization using a diagnostically specified antigen serves excellently. It should be noted, however, that the currently available method of therapy of hyposensitization requires an antigen solution to be intracutaneously administered little by little once or twice each week for three to four months over which period the starting dose is escalated to a maintenance dose, which is then maintained for one to three years. If dose escalation is easy, it can be expected that excellent therapeutic effects can be obtained. However, grave side reactions can occur because of the above uncertain potency of the antigen used, and because of the presence of various impurity substances therein, thereby greatly limiting its use of the antigen.

Fungi belonging to the genus *Malassezia* (hereinafter abbreviated as M.) are known to include *M. furfur* (also known as *Pityrosporum ovale* or *Pityrosporum orbiculare*), *M. pachydermatis, M. sympodialis*, and the like. *Malassezia* is reportedly commonly present on the body surfaces of various animals and on those of humans. Its pathogenicity and role in allergoses have long been studied. Regarding pathogenicity, *Malassezia* is suspected of being causative microorganisms for dermatitis, tinea versicolor, folliculitis, dandruff, and other conditions. It is also suspected of being associated with allergoses, such as atopic dermatitis, and there is a great chance that it is involved in these diseases as a causative microorganism.

Currently, antigen extracts from *Malassezia* are commercially available. These extracts are unpurified or partially purified products obtained from cultures of *M. furfur*, and are thus considered complex mixtures comprising proteins, sugars, and lipids.

Conventionally, a large number of allergenic proteins from *Malassezia* have been reported to be contained in such antigen extracts, including 87, 76, 67, 45, 37, 28, 25, 14, 13 kDa IgE-binding proteins, which are detected by immunoblotting using IgE antibodies in sera of patients after a crude extract from a *Malassezia* fungus is separated by SDS-polyacrylamide gel electrophoresis (PAGE) (Siv Johansson et al., *Acta Derm. Venereol.*, 71, 11-16, 1991; E. Jensen-Jarolim et al., *J. Allergy Clin. Immunol.*, 89, 44-51, 1992; Zargari et al., *Allergy*, 49, 50-56, 1994). Thus, since the proteins produced by the *Malassezia* fungi are beyond a wide variety of proteins, simple separation by SDS-PAGE alone is unsatisfactory, and it cannot be thought that a single protein band in SDS-PAGE which is conventionally reported represents a homogenous protein. In other words, because a plurality of proteins sharing the same protein band in SDS-PAGE are usually present, an IgE-binding protein, even if a single protein band is shown, must be separated from many other proteins contained in the band, which in turn necessitates combining with another effective separation method. Furthermore, in order to be useful for a diagnostic or therapeutic purpose, it is necessary to isolate an antigenic protein and clarify its antigenicity using a number of sera from patients, to identify it as the major allergen, and to establish a method for producing it for supplying the desired produce with demonstrated protein chemical quality. For these reasons, a homogenous and single antigenic protein must be isolated by repeating separation by various chromatographies and assay of the antigen activity. The protein finally obtained needs to be confirmed as having homogeneity in ion exchange chromatography and homogeneity in isoelectric electrophoresis, as well as that in SDS-PAGE.

According to the above-mentioned various reports, however, such substances observed in SDS-PAGE are dealt with as if they each represent a single IgE-binding protein. Actually, however, no one have yet been successful to isolate and purify them, and there have never been discussed on the identity of the band as a mixture of many mutually unrelated proteins. Accordingly, as a matter of course, no attempts have been yet made to isolate IgE-binding proteins from the complicated mixture and confirm the antigenicity thereof as isolated proteins using sera of patients with allergy. Further, no reports have been yet made regarding the properties of protein chemistry or amino acid sequences thereof. For this reason, it remains unknown as to the mutual identity or relevancy (for example, one is a decomposition product by protease of the other protein), and other aspects of IgE-binding proteins discussed in the above reports.

Even though the *Malassezia* fungi have been remarked as causative microorganisms for allergoses, including atopic dermatitis, as described above, no one have yet succeeded in isolating and purifying an IgE-binding protein from a crude extract comprising a complicated protein mixture. As a matter of course, the antigenicity of such an isolated protein has not been confirmed using sera of patients with allergy. Moreover, there have been no reports of the properties of protein chemistry or amino acid sequences thereof, and there are no reported cases on isolation of the gene encoding the above protein.

DISCLOSURE OF THE INVENTION

In order to assess the likelihood of being a causative microorganism, skin tests using crude antigens, *Malassezia* cell extracts as described above, provocative tests, quantitative assay tests for various IgE antibodies by RAST method, assay for histamine release, and the like, and other approaches are performed, in addition to microbiological cultivation tests. Because these crude antigens contain a large number of different impurity substances, however, accurate diagnosis cannot be made. In addition, when used for skin tests and provocative tests, the crude antigen can pose a risk of development of adverse reactions, and the like. Moreover, when using the crude antigen for therapy of hyposensitization, there is a risk of anaphylactogenesis associated therewith, posing extreme limitation on the dose of the crude antigen, so that therapeutic effects cannot be expected. In addition, it is also difficult to use the crude antigen as a vaccine for preventing infections. To date, there have been no successful cases on isolation of such purified pure antigen from *Malassezia*, and there is, therefore, a major set back on the infections caused by *Malassezia* fungi and the diagnosis and therapy of allergoses.

Accordingly, in consideration of the present situation, the following objects are achieved by the present invention.
(1) A first object of the present invention is to provide a substantially pure, isolated, antigenic protein from fungi of the genus *Malassezia*, namely a purified *Malassezia* allergen, preferably a main allergen for patients with *Malassezia* allergoses, and to provide their properties of protein chemistry. Further, the object is also to provide a functionally equivalent antigenic protein having properties immunologically equivalent to those of the antigenic protein.
(2) A second object of the present invention is to provide an antigenic fragment having an antigenic epitope contained in these purified antigenic proteins.
(3) A third object of the present invention is to provide an antibody or fragments thereof against the above antigenic protein or antigenic fragments.
(4) A fourth object of the present invention is to provide a diagnostic agent for diseases, such as allergoses of which causative microorganisms are *Malassezia* fungi, the diagnostic agent including, as an active ingredient, the above antigenic protein or antigenic fragments.
(5) A fifth object of the present invention is to provide a therapeutic agent for diseases, such as allergoses of which causative microorganisms are *Malassezia* fungi, the therapeutic agent including, as an active ingredient, the above antigenic protein or antigenic fragments.
(6) A sixth object of the present invention is to provide a method for immunological, quantitative assay of the *Malassezia* allergen.
(7) A seventh object of the present invention is to provide a novel recombinant *Malassezia* antigenic protein having immunological properties equivalent to those of the purified antigenic protein of item (1).
(8) A eighth object of the present invention is to provide a polynucleotide encoding a novel recombinant *Malassezia* antigenic protein.
(9) A ninth object of the present invention is to provide an antigenic fragment having an epitope contained in the recombinant *Malassezia* antigenic protein.
(10) A tenth object of the present invention is to provide an antibody or fragments thereof which specifically bind to the above recombinant *Malassezia* antigenic protein or antigenic fragments thereof.
(11) An eleventh object of the present invention is to provide a synthesized oligonucleotide probe or a synthesized oligonucleotide primer which hybridizes to the above polynucleotide.
(12) A twelfth object of the present invention is to provide a diagnostic agent for *Malassezia* allergoses or *Malassezia* infectious diseases, including, as an active ingredient, the above recombinant *Malassezia* antigenic protein or antigenic fragments thereof.
(13) A thirteenth object of the present invention is to provide a therapeutic agent for *Malassezia* allergoses or *Malassezia* infectious diseases, including, as an active ingredient, the above recombinant *Malassezia* antigenic protein or antigenic fragments thereof.

For the purpose of isolating *Malassezia* allergens useful for the diagnosis and therapy of patients with allergy with the cell components of *M. furfur* TIMM2782, a fungal strain belonging to the genus *Malassezia*, the present inventors have screened sera of patients with RAST-positive and positive skin tests for antigenic proteins, using cell extract crude antigens. As a result, the present inventors have succeeded in isolating 13 kinds of antigenic proteins designated as MF-1 to -13, respectively, and also succeeded in determination of the partial amino acid sequences of some of the antigenic proteins. Moreover, the present inventors have synthesized a polynucleotide to be used for primers on the basis of the information for the partial amino acid sequences of the *Malassezia* antigenic proteins thus isolated, and carried out polymerase chain reaction (PCR) with a cDNA derived from *M. furfur* cell mRNA as the starting material, using the polynucleotide as a primer, to give a portion of the gene encoding the desired *Malassezia* antigenic protein. Next, the desired gene has been isolated from an *M. furfur* cell cDNA library using the entire or partial fragment of this PCR fragment as a probe. Also, an overlapping peptide has been synthesized on the basis of the amino acid sequence of MF-1. The present inventors have clarified that an epitope for T cell and an epitope for B cell can be found by carrying out search for an epitope against the patient serum IgE antibody and search for another epitope against the MF-1 monoclonal antibody, using the above peptide. The present invention has been completed based on the above finding.

In other words, one embodiment of the present invention relates to a substantially pure, isolated, antigenic protein or antigenic fragments thereof from fungi of the genus *Malassezia*, characterized by having a binding ability to an IgE antibody from patients with allergoses.

Another embodiment of the present invention relates to a recombinant *Malassezia* antigenic protein or antigenic fragments thereof, characterized by having immunological properties functionally equivalent to those of the isolated and purified antigenic protein.

Another embodiment of the present invention relates to a polynucleotide encoding the recombinant *Malassezia* antigenic protein or antigenic fragments thereof of the present invention.

Another embodiment of the present invention relates to an antibody or fragments thereof against the isolated and purified antigenic protein or antigenic fragments thereof of the present invention, or against the recombinant *Malassezia* antigenic protein or antigenic fragments thereof of the present invention.

Another embodiment of the present invention relates to a synthesized oligonucleotide probe or a synthesized oligonucleotide primer which hybridizes to the polynucleotide of the present invention.

Another embodiment of the present invention relates to a diagnostic agent for *Malassezia* allergoses or *Malassezia* infectious diseases, characterized in that the diagnostic agent includes, as an active ingredient, the isolated and purified antigenic protein or antigenic fragments thereof of the present invention, or the recombinant *Malassezia* antigenic protein or antigenic fragments thereof of the present invention.

Another embodiment of the present invention relates to a therapeutic agent for *Malassezia* allergoses or *Malassezia* infectious diseases, characterized in that the therapeutic agent includes, as an active ingredient, the isolated and purified, antigenic protein or antigenic fragments thereof of the present invention, or the recombinant *Malassezia* antigenic protein or antigenic fragments thereof of the present invention.

Another embodiment of the present invention relates to a method for quantitative assay of *Malassezia* allergen, characterized in that the immunological, quantitative assay of the *Malassezia* allergen is conducted by using the isolated and purified antigenic protein of the present invention, or the recombinant *Malassezia* antigenic protein of the present invention as a standard and antibodies against the above antigenic protein.

BRIEF DESCRIPTION OF THE DRAWINGS

FIG. 17 is comparative figures of two nucleotide sequences of MF-5 cDNA (SEQ ID NOS: 5 and 33).

FIG. 18 is comparative figures of two nucleotide sequences of MF-6 PCR fragment (SEQ ID Nos: 37 and 38).

FIG. 19 is comparative figures of nucleotide sequences of MF-1 cDNA and MF-2 cDNA (SEQ ID NOS: 1 and 2).

FIG. 20 is comparative figures of nucleotide sequences of MF-3 cDNA and MF-4 cDNA (SEQ ID NOS: 3 and 4).

FIG. 21 shows amino acid sequences of MF-1 overlapping peptides.

FIG. 23 is comparative figures of MF-1 cDNA and MF-1 genomic DNA (SEQ ID NOS: 18 and 19).

BEST MODE FOR CARRYING OUT THE INVENTION

Figure 1:
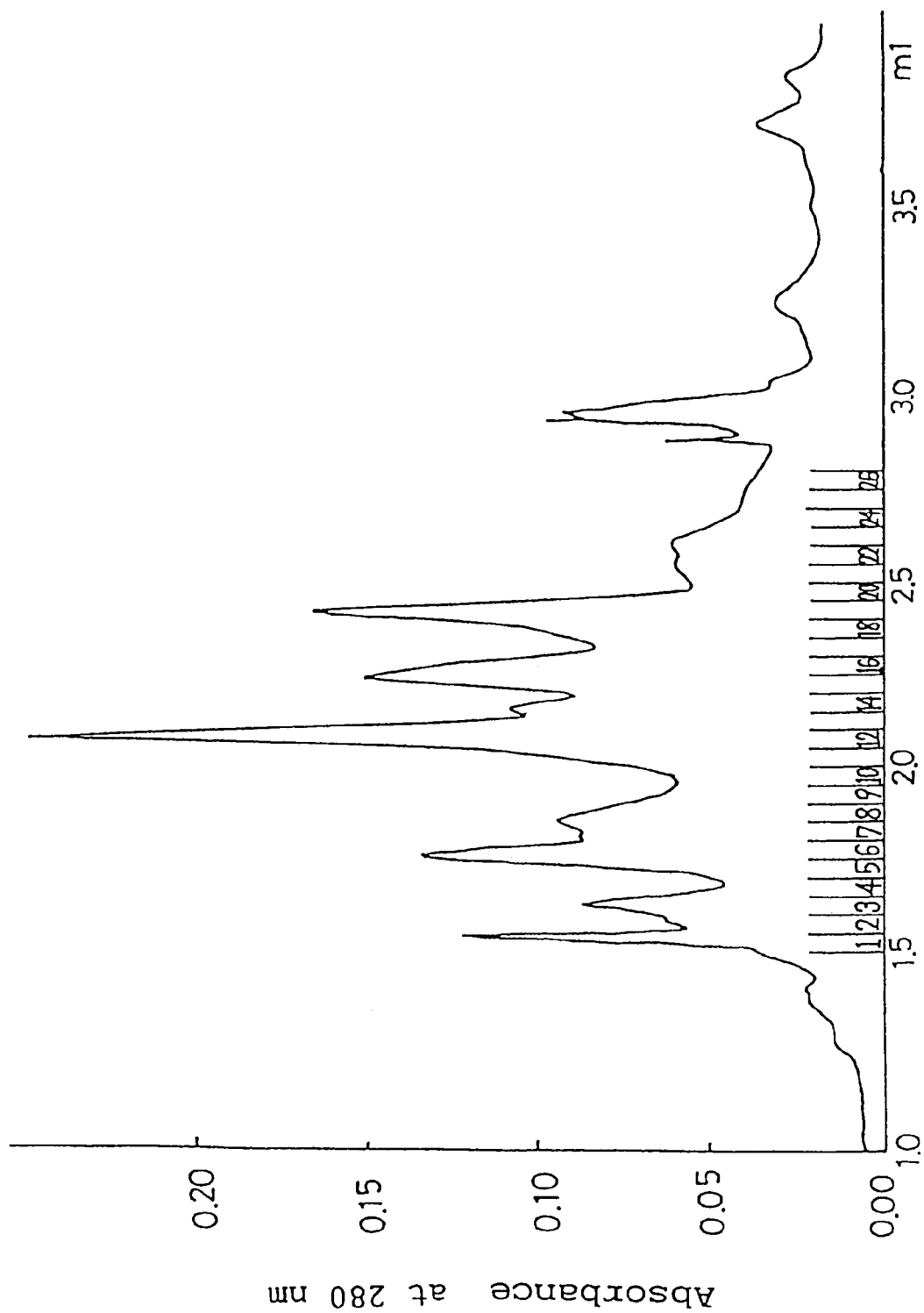
FIG. 1 is a graph showing chromatographic analysis by Mono Q of a partially purified, crude antigen 2782 of *Malassezia*.

The present invention is hereinafter described in detail.

(1) Purified Antigenic Protein of Present Invention and Functionally Equivalent Antigenic Proteins Thereof The antigenic protein of the present invention is a substantially pure, isolated, antigenic protein from fungi of the genus *Malassezia*, which is, in some cases, hereinafter simply referred to as "isolated and purified antigenic protein from *Malassezia*" or more simply "purified, antigenic protein", characterized in that the antigenic protein has a binding ability to IgE antibodies from patients with allergoses. Here, the phrase "substantially pure, isolated" as used herein means that the protein of interest is substantially homogenous as a protein, wherein the protein does not substantially contain other impurity proteins, and wherein the isolated protein is recognized as a single substance as determined by SDS-PAGE and isoelectric electrophoresis.

In addition, the purified, antigenic protein of the present invention is characterized in that the antigenic protein is a major allergen from *Malassezia* reactive to patients with allergoses showing a positive reaction in a skin test to a crude antigen of *Malassezia*.

Also, the purified, antigenic protein of the present invention is an antigenic protein present in the fungal cells of the genus *Malassezia*.

Additionally, the purified, antigenic protein of the present invention is characterized in that the antigenic protein has an epitope therein recognized by IgE antibodies from patients with allergoses, especially IgE antibodies from patients with *Malassezia* allergoses.

The strain which can be used in order to obtain the purified, antigenic protein of the present invention may be any strain, as long as the strain belongs to the genus *Malassezia*, and is exemplified, for instance, by *M. furfur*(*Malassezia furfur*) TIMM2782. The above strain is identified as *Malassezia furfur* TIMM2782 and deposited with an accession number FERM BP-5611 with National Institute of Bioscience and Human-Technology, Agency of Industrial Science and Technology, which is addressed at 1-3, Higashi 1-chome, Tsukuba-shi, Ibaraki-ken, Japan, zip code: 305; date of original deposit: Sep. 12, 1995; and date of transfer request to the International Deposit: Jul. 29, 1996.

The term "major allergen from *Malassezia*" referred in the present specification is defined as a purified, antigenic protein which is recognized by IgE antibodies, and reactive to not less than 50% of the patients with *Malassezia* allergoses, i.e. patients with allergoses with positive skin reaction to commercially available crude antigen extracts of *Malassezia*.

The phrase "binding ability to IgE antibodies from patients with allergoses" referred in the present specification means that significantly enhanced binding, in comparison with standard sera, can be obtained, as determined by RAST method using a $^{125}$I-labeled anti-IgE serum, or direct-RAST RIA method or ELISA method using an enzyme-labeled anti-IgE serum.

The isolated and purified, antigenic protein from *Malassezia* of the present invention has a molecular weight of from 10,000 to 100,000, as determined by SDS-PAGE, under reduced conditions or non-reduced conditions, and an isoelectric point of from 4 to 10 in a native state or in a denatured state with 8 M urea, and the isolated and purified, antigenic protein from *Malassezia* is present in the fungal cells of the genus *Malassezia*. Concrete examples thereof include MF-1, MF-2, MF-3, MF-4, MF-5, MF-6, MF-7, MF-8, MF-9, MF-10, MF-11, MF-12, MF-13, and the like. The molecular weights, the isoelectric points, and the partial amino acid sequences of these purified, antigenic proteins will be described hereinbelow.

(I) MF-1 has a molecular weight, as determined by SDS-PAGE, of about 21 kDa under reduced conditions and about 40 kDa under non-reduced conditions, an isoelectric point of about 4.8 in a native state, and an isoelectric point of about 5.3 in a denatured state with 8 M urea, and contains an amino acid sequence as shown by SEQ ID NO:45 in Sequence Listing.

(II) MF-2 has a molecular weight, as determined by SDS-PAGE, of about 20 kDa under reduced conditions and about 40 kDa under non-reduced conditions, an isoelectric point of about 4.8 in a native state, and an isoelectric point of about 5.8 in a denatured state with 8 M urea, and contains amino acid sequences as shown by SEQ ID NO:46, SEQ ID NO:47, and SEQ ID NO:48, and its N-terminus is blocked.

(III) MF-3 has a molecular weight, as determined by SDS-PAGE, of about 27 kDa under reduced conditions and also about 27 kDa under non-reduced conditions, an isoelectric point of about 5.2 in a native state, and an isoelectric point of about 6.5 in a denatured state with 8 M urea, and contains amino acid sequences as shown by SEQ ID NO:49, SEQ ID NO:50, and SEQ ID NO:51, and its N-terminus is blocked.

(IV) MF-4 has a molecular weight, as determined by SDS-PAGE, of about 26 kDa under reduced conditions and also about 26 kDa under non-reduced conditions, an isoelectric point of about 5.2 in a native state, and an isoelectric point of about 6.3 in a denatured state with 8 M urea, and contains an amino acid sequence as shown by SEQ ID NO:52.

(V) MF-5 has a molecular weight, as determined by SDS-PAGE, of about 66 kDa under reduced conditions, and an isoelectric point of about 6.1 in a denatured state with 8 M urea, and contains an amino acid sequence as shown by SEQ ID NO:53.

(VI) MF-6 has a molecular weight, as determined by SDS-PAGE, of about 43 kDa under reduced conditions, and an isoelectric point of about 6.2 in a denatured state with 8 M urea, and contains an amino acid sequence as shown by SEQ ID NO:54.

(VII) MF-7 has a molecular weight, as determined by SDS-PAGE, of about 15 kDa under reduced conditions, and an isoelectric point of about 6.0 in a denatured state with 8 M urea, and contains an amino acid sequence as shown by SEQ ID NO:55.

(VIII) MF-8 has a molecular weight, as determined by SDS-PAGE, of about 30 kDa under reduced conditions, and an isoelectric point of about 5.4 in a denatured state with 8 M urea, and its N-terminus is blocked.

(IX) MF-9 has a molecular weight, as determined by SDS-PAGE, of about 40 kDa under reduced conditions, and an isoelectric point of about 5.3 in a denatured state with 8 M urea.

(X) MF-10 has a molecular weight, as determined by SDS-PAGE, of about 44 kDa under reduced conditions, and an isoelectric point of about 6.2 in a denatured state with 8 M urea, and contains an amino acid sequence as shown by SEQ ID NO:56.

(XI) MF-11 has a molecular weight, as determined by SDS-PAGE, of about 45 kDa under reduced conditions, and an isoelectric point of about 6.4 in a denatured state with 8 M urea, and its N-terminus is blocked.

(XII) MF-12 has a molecular weight, as determined by SDS-PAGE, of about 100 kDa under reduced conditions, and an isoelectric point of about 5.0 in a denatured state with 8 M urea.

(XIII) MF-13 has a molecular weight, as determined by SDS-PAGE, of about 16 kDa under reduced conditions, and an isoelectric point of about 8.1 in a native state, and contains an amino acid sequence as shown by SEQ ID NO:57.

The isolated and purified, antigenic protein from *Malassezia* of the present invention may be any protein, as long as the antigenic protein is from *Malassezia* and recognized as an antigen of mammals, including humans, and the antigenic protein is not limited to the 13 kinds of purified, antigenic proteins exemplified above.

Furthermore, diagnoses using these purified, antigenic proteins yield results correlating to those of diagnoses based on skin tests and RAST method using extracts of crude conventional antigen of *Malassezia*. Specifically, many of the patients showing positive reaction in a skin test using crude antigens also show positive reaction for IgE antibody titer against the crude antigens of *Malassezia*. Not less than 50% of the patients with positive reaction for IgE antibody titer against crude antigens have high IgE antibody titers against the above-described isolated and purified, antigenic protein of the present invention (see Tables 2 and 3 in Examples set forth below).

Also, when administered to patients with *Malassezia* allergoses, the purified, antigenic protein of the present invention is capable of lowering the allergic response to *Malassezia* fungi in patients with *Malassezia* allergoses administered therewith.

Moreover, the present invention provides functionally equivalent antigenic proteins having properties immunologically equivalent to those of the above-described purified, antigenic protein. For example, as functional equivalents having properties immunologically equivalent to those of the above-described 13 kinds of purified, antigenic proteins, functional equivalents of various strains of *M. furfur*, and functional equivalents of fungal species of the genus *Malassezia* other than *M. furfur*, are also encompassed in the scope of the present invention. Specifically, MF-2 is homologous to a peroxisome membrane protein PMP-20 [L. Garrard et al., *J. Biol. Chem.*, 23, 13929-13937 (1989)], and proteins from *Malassezia* having similar immunological properties are encompassed in the scope of the present invention. Also, MF-3 and MF-4, which are different proteins, are both homologous to iron/manganese-superoxide dismutase [T. Matsumoto et al., *Biochemistry*, 30, 3210-3216 (1991); M. L. Ludwig et al., *J. Mol. Biol.*, 219, 335-358 (1991)]; and MF-5, MF-6, and MF-13 are homologous to dihydrolipoamide dehydrogenase (DLDH), malate dehydrogenase (MDH), and cyclophilin, respectively, and proteins from *Malassezia* having similar immunological properties are encompassed in the scope of the present invention.

Incidentally, the purified, antigenic protein of the present invention can be modified, derivatized, or bound to polyethylene glycol (PEG) by the PEG method [Wie et al., *Int. Arch. Allergy Appl. Immunol.*, 64, 84-99 (1981)], in order to enhance stability and/or desired reactivity, i.e. to enhance antigen-antibody specific binding for diagnostic purposes, or to attenuate allergic reaction or eliminate enzymatic activity for therapeutic purposes. Protein modifications include pyridylethylation, reduction, alkylation, acylation, chemical coupling to suitable carriers, gentle formalin treatment, and guanidine hydrochloride treatment.

(2) Antigenic Fragment of Present Invention

The antigenic fragment of the present invention is an antigenic fragment derived from the purified, antigenic protein, characterized in that the antigenic protein has an antigenic epitope contained in the above-described purified, antigenic protein. The antigenic fragments are exemplified by, for instance, antigenic fragments derived from purified, antigenic protein containing at least one antigenic epitope contained in MF-1, MF-2, MF-3, MF-4, MF-5, MF-6, MF-7, MF-8, MF-9, MF-10, MF-11, MF-12, MF-13, and the like, among which preference is given to those containing at least one T cell epitope or B cell epitope. The antigenic fragments of the present invention include fragments derived from the purified, antigenic protein of *Malassezia*. The fragments cause immune responses in mammals, especially in humans, for instance, minimum levels of stimulation of IgE production, IgE binding, induction of IgG and IgM antibody production, and T cell proliferation, and/or lymphokine secretion, and/or induction of T cell anergy.

When using the antigenic fragment of the present invention for therapeutic purposes, it is desired that the antigenic fragment is weak in activation of T cell response, or induces T cell anergy. Also, it is preferred that the antigenic fragment of the present invention does not substantially have a binding ability to IgE antibodies specific to *Malassezia* fungi, or even when the antigenic fragment is bound to the IgE antibody, the binding is at a level where no mediators, such as histamine, are released from mast cells or basophiles. In other words, it is preferred that even when binding to IgE antibodies occurs, the antigenic fragment binds to IgE antibodies at levels substantially lower than those for the purified, antigenic proteins from *Malassezia*. As described above, the antigenic fragment of the present invention preferably has a lower activity of activation in IgE-mediated immune response than that of the purified, antigenic proteins when used for therapeutic purposes. Therefore, when administered to patients with *Malassezia* allergoses, it is made possible to reduce allergic responses to *Malassezia* fungi in patients with *Malassezia* allergoses administered therewith.

The antigenicity of the antigenic fragment of the present invention can also be assessed in in vitro tests, such as RAST method, ELISA method, and histamine release tests, as well as in skin tests and intracutaneous tests to human volunteers.

The term "epitope" is a basic element or minimum unit recognized by receptors, especially antibodies, such as immunoglobulins, histocompatibility antigens, and T cell receptors, and contains amino acid sequences essential for receptor recognition. Other peptides resembling the amino acid sequence of an epitope, which can lower the allergic response to a *Malassezia* allergen, can also be used as epitopes. It is possible to design a *Malassezia* allergen peptide which is likely to change the allergic response to *Malassezia* fungi in patients with *Malassezia* allergoses when administered in sufficient amounts to the patients by currently available information on protein structures. It is also possible to design reagents or drugs which inhibit induction of allergic reaction in patients with *Malassezia* allergoses. For example, such drugs can be designed to bind to IgE antibodies against *Malassezia* allergens, and to thereby interfere with IgE-allergen binding and subsequent degranulation from mast cells.

Also, selection of peptides containing a T cell epitope can be carried out by culturing T lymphocytes obtained from an individual sensitive to a *Malassezia* allergen, i.e. individuals with IgE-mediated immune response, with a peptide from allergen, and then measuring stimulating activity for human T cell, i.e. blast formation activity, for instance, by means of determining whether or not T cell proliferation occurs in response to the addition of the peptide by measuring incorporation of tritiated thymidine into cells. Peptides containing a B cell epitope can be selected by reacting sera obtained from an individual sensitive to a *Malassezia* allergen with each peptide derived from the allergen, and measuring the amount of bound IgE to the peptide.

Peptides having immunological cross-reactivity to the fragment of the purified, antigenic proteins from *Malassezia*, including *Malassezia* allergens, for instance, those recognized by specific antibodies or T cells against the fragment thereof are encompassed in the antigenic fragment of the present invention.

In order to prepare the antigenic fragment of the present invention, an isolated and purified, antigenic protein, a starting material, is enzymatically digested with a protease, such as lysylendopeptidase or trypsin, or cleaved by chemical treatment with agents such as cyanogen bromide, after which a fragment having a desired antigenicity is isolated and purified by known methods of protein purification. It is also possible to express and prepare the desired antigenic fragment using a portion of the gene encoding an antigenic protein derived from *Malassezia*. Further, it can be also prepared by chemical synthesis utilizing peptide synthesis technology based on information on the chemical structure of the antigenic fragment.

In addition, amino acid substitution, insertion and deletion can be carried out using genetic engineering techniques and chemical synthesis techniques. For example, to enhance stability and/or enhance the desired reactivity, the antigenic fragment of the present invention may be derivatized, or modified by deletion, insertion, substitution or addition of at least one amino acid. The modified protein or peptide of the present invention can also be modified by replacing an amino acid with a D-amino acid, a non-natural amino acid, or a non-natural amino acid analogue, or by adding these amino acids or analogues. The antigenic fragment of the present invention can also be chemically modified by binding with polyethylene glycol. Modifications of the antigenic fragment include reduction, alkylation, acylation, and chemical coupling to suitable carriers.

The antigenic fragment thus obtained can be determined and isolated by measuring the induction of immune responses, including activation of T cell response, induction of T cell anergy, binding with antibody, and the like.

Next, the method for producing the purified, antigenic protein of the present invention will be described below. Conventionally used crude antigens have been lyophilized products of culture filtrates, or purified products obtained from cultured cells by very limited means of purification, such as disrupting the cells by a suitable method to obtain an extract, and then subjected to precipitation with ammonium sulfate and lyophilizing. The present inventors have also attempted purification using such crude antigens as starting materials by commonly used methods of protein purification, e.g., gel filtration, ion exchange and other chromatographies, but they have not succeeded in isolation of a single pure, antigenic protein using these techniques only.

The isolated and purified, antigenic protein from *Malassezia* of the present invention can be isolated by fractionating a crude antigen prepared from *Malassezia* cells as a starting material by an appropriate combination of effective separation methods using ion exchange chromatography, chelate resin chromatography, hydrophobic chromatography, gel filtration chromatography, and the like, then measuring the binding of each fraction with an IgE antibody of patient sera by RAST method, immunoblotting, and the like, to search for a protein that binds to the IgE antibody in the allergic patient sera, or to search for a protein that induces immune responses, including activation of T cell response, T cell anergy, and the like, by various methods using patient lymphocytes.

Specifically, a fungus of the genus *Malassezia*, such as *M. furfur*, is cultured under appropriate temperature, aeration and other conditions using a medium containing nutrients suitable for the growth of *Malassezia* fungi, supplemented with olive oil or Tween 40 or Tween 60, such as Dixon medium. The obtained cells are disrupted by a suitable method to yield an extract. From this extract, the antigenic protein can be purified using separation means, including ion exchange chromatography, chelate resin chromatography, and hydrophobic chromatography. In other words, the antigenic protein can be isolated as a high-purity protein using an appropriate combination of various known methods of peptide and protein purification, such as ion exchange chromatography, hydrophobic chromatography, gel filtration chromatography, chelate resin chromatography, electrophoresis, and affinity chromatography using a resin coupled with an antibody specific to an antigenic protein derived from *Malassezia* or an antigenic fragment thereof. The antigenic protein contained in the culture filtrate can be isolated in the same manner.

Specifically, as shown in Examples below, a group of a large number of well-resembled proteins that are inseparable on the basis of molecular weight can be separated from each other by combining ion exchange chromatography, utilizing the differences in isoelectric points; hydrophobic chromatography, utilizing differences in hydrophobicity; chelate resin chromatography, utilizing differences in chelating abilities with metals; gel filtration chromatography, utilizing the molecular weight differences, and the like. These findings have been unexpected from the findings concerning differences of the antigenic proteins on the basis of the molecular weight shown by conventional SDS-PAGE immunoblotting. For example, MF-1 and MF-2 are almost identical in terms of molecular weight, and they are mutually inseparable by conventional SDS-PAGE. It is also impossible to mutually separate MF-3 and MF-4 on the basis of molecular weight.

Concrete examples of the combinations of various separation means are given below, as exemplified by the following steps:

Step a: Centrifuging a cell disruption extract of a cultured *Malassezia* fungus, lyophilizing the resulting supernatant, and thereafter subjecting the lyophilized product to anionic exchange chromatography (for instance, DEAE-cellulose column chromatography, manufactured by Wako Pure Chemical Industries) to obtain a fraction eluted with 0.1 M NaCl;

Step b: Concentrating the eluted fraction obtainable in Step a using an ultrafiltration membrane (MW 10,000), and thereafter subjecting the resulting concentrate to gel filtration chromatography (for instance, Sephacryl S-200HR column chromatography, manufactured by Pharmacia) to obtain a fraction eluted at molecular weights of 30,000 to 50,000;

Step c: Concentrating the eluted fraction obtainable in Step b using an ultrafiltration membrane (MW 10,000), and thereafter subjecting the concentrate to gel filtration chromatography (for instance, Sephadex G-75 Superfine column chromatography, manufactured by Pharmacia) to obtain a fraction eluted at a molecular weight of about 40,000;

Step d: Subjecting the eluted fraction obtainable in Step c to zinc chelating chromatography (for instance, Zinc Chelating Sepharose fast flow column chromatography, manufactured by Pharmacia), and further subjecting the resulting effluent fraction to copper chelate chromatography to obtain an effluent fraction or a fraction eluted at pH about 4;

Step e: Concentrating the effluent fraction or the fraction eluted at pH about 4 obtainable in Step d, and thereafter purifying the resulting concentrate by gel filtration chromatography (for instance, Sephadex G-75 Superfine column chromatography, manufactured by Pharmacia) to obtain a fraction eluted at a molecular weight of about 40,000; and Step f: Further purifying the eluted fraction obtainable in Step e by ion exchange chromatography of Mono Q.

Alternatively, there may be included the following steps as one example.

Step a: Centrifuging a cell disruption extract of a cultured *Malassezia* fungus; lyophilizing the resulting supernatant, and thereafter subjecting the lyophilized product to anionic exchange chromatography (for instance, DEAE-cellulose column chromatography) to obtain a fraction eluted with 0.1 M NaCl;

Step b: Concentrating the eluted fraction obtainable in Step a using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000;

Step c: Concentrating the eluted fraction obtainable in Step b using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000;

Step d: Subjecting the eluted fraction obtainable in Step c to zinc chelating chromatography (for instance, Zinc Chelating Sepharose fast flow column chromatography) to obtain a fraction eluted at pH about 5; and Step g: Concentrating the eluted fraction obtainable in Step d, and thereafter purifying the resulting concentrate by subjecting the concentrate to gel filtration chromatography (for instance, Sephadex G-75 Superfine column chromatography).

Next, the method of the present invention will be explained in further detail by taking, as examples, the production methods for purified, antigenic proteins (MF-1, MF-2, MF-3, MF-4, and MF-13) of the present invention. However, the following steps are simply examples, without intending to limit the scope of the present invention thereto.

1. Production Example of MF-1

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography), and further subjecting the resulting effluent fraction to copper chelate chromatography to obtain a fraction eluted at a pH of about 4; and concentrating the resulting eluted fraction, and thereafter purifying the concentrate by gel filtration chromatography (for instance, Sephadex G-75 Superfine column chromatography) to obtain a fraction eluted at a molecular weight of about 40,000.

2. Production Example MF-2

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain a fraction eluted at a pH of about 5; and concentrating the resulting eluted fraction, and thereafter purifying the resulting concentrate by gel filtration chromatography (for instance, Sephadex G-75 Superfine column chromatography).

3. Production Example MF-3

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain an effluent fraction, and further subjecting the effluent fraction to copper chelate chromatography; concentrating the resulting effluent fraction, and thereafter purifying the resulting concentrate by gel filtration chromatography (for instance, Sephadex G-75 Superfine column chromatography) to obtain a fraction eluted at a molecular weight of about 40,000; and further purifying the resulting fraction by anionic exchange chromatography of Mono Q.

4. Production Example MF-4

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to obtain a fraction eluted with 0.1 M NaCl; concentrating the resulting eluted fraction using an ultrafiltration membrane (MW 10,000), and thereafter subjecting the resulting concentrate to gel filtration chromatography (for instance, Sephacryl S-200HR column chromatography) to obtain a fraction eluted at molecular weights of 30,000 to 50,000; concentrating the resulting eluted fraction using an ultrafiltration membrane (MW 10,000), and thereafter subjecting the resulting concentrate to gel filtration chromatography (for instance, Sephadex G-75 Superfine column chromatography) to obtain a fraction eluted at a molecular weight of about 40,000; subjecting the resulting eluted fraction to zinc chelating chromatography (for instance, Zinc Chelating Sepharose fast flow column chromatography) to obtain an effluent fraction, and further subjecting the effluent fraction to copper chelate chromatography; concentrating the resulting effluent fraction, and thereafter purifying the resulting concentrate by gel filtration chromatography (for instance, Sephadex G-75 Superfine column chromatography) to obtain a fraction eluted at a molecular weight of about 40,000; and further purifying the resulting fraction by anionic exchange chromatography of Mono Q.

5. Product Example MF-13

This method comprises centrifuging a cell disruption extract of cultured *M. furfur* (*Malassezia furfur*) TIMM 2782 cells, lyophilizing the resulting supernatant, and thereafter subjecting the lyophilized product to anionic exchange chromatography (for instance, DEAE-cellulose column chromatography) to collect a non-adsorbing fraction; subjecting the fraction to gel filtration chromatography (for instance, Superdex 75 pg) to obtain an eluted fraction with a molecular weight of not more than 20,000; subjecting the resulting fraction to SP cationic exchange chromatography to obtain a fraction eluted with 0.2 M NaCl; and further purifying the eluted fraction by gel filtration chromatography (for instance, Superdex 75 pg).

In addition, the antigenic protein derived from *Malassezia* of the present invention can be prepared as a recombinant protein by a method comprising isolating a gene encoding the protein by such methods as PCR based on the information on the amino acid sequence mentioned above, and inserting the genes into a vector by genetic engineering techniques so as to be expressed in *E. coli*, yeasts, molds, mammalian cells, and the like.

(3) Antibody or Antibody Fragment of Present Invention Against Purified, Antigenic Protein or Antigenic Fragment Thereof The antibody of the present invention against an isolated and purified, antigenic protein from *Malassezia* or an antigenic fragment thereof can be prepared by using as an antigen the purified, antigenic protein from *Malassezia* of the present invention, an antigenic fragment obtainable by enzymatic or chemical treatment of the above protein, or an antigenic peptide obtained by chemical synthesis. The antibody can be prepared by a conventional method including, e.g., a method comprising immunizing an animal, such as a rabbit, with the above-described protein or a fragment thereof together with an adjuvant to obtain an antiserum. Also, a monoclonal antibody can be prepared by fusing an antibody-producing B cell obtainable by immunizing an antigen and a myeloma cell, selecting a hybridoma for producing the desired antibody, and culturing this cell. These antibodies can be used for production of an antigenic protein, measurement of titration of antigen extract of *Malassezia* allergen, and other purposes, as described later. As hybridomas mentioned above, a hybridoma for producing an M-40 monoclonal antibody against the antigenic protein MF-1 is named and identified as 5B4; a hybridoma for producing an M-3 monoclonal antibody against the antigenic protein MF-2 is named and identified as 8G11; and hybridoma for producing an M-1 monoclonal antibody against the against the antigenic protein MF-3 is named and identified as 10C1, and these hybridomas are deposited as FERM BP-5608, FERM BP-5609, and FERM BP-5610, respectively, with National Institute of Bioscience and Human-Technology, Agency of Industrial Science and Technology, addressed at 1-3, Higashi 1-chome, Tsukubashi, Ibaraki-ken, Japan (zip code: 305; date of original deposit: Sep. 12, 1995; date of transfer request to the International Deposit: Jul. 29, 1996.

(4) Diagnostic Agent of Present Invention Containing as Active Ingredient Purified, Antigenic Protein or Antigenic Fragment Thereof The present invention provides a diagnostic agent for allergoses or infectious diseases of which causative microorganisms are *Malassezia* fungi, using an isolated and purified, antigenic protein from *Malassezia* or an antigenic fragment having at least one antigenic epitope derived from the antigenic protein.

The term "allergoses of which causative microorganisms are *Malassezia* fungi" as used herein is defined as any allergoses of which causative microorganisms are *Malassezia* fungi, exemplified by atopic bronchial asthma, allergic rhinitis, allergic conjunctivitis, and atopic dermatitis. The term "infectious disease of which causative microorganisms are *Malassezia* fungi" is defined as any infectious disease of which causative microorganisms are *Malassezia* fungi, exemplified by tinea versicolor, *Malassezia* folliculitis, and dandruff.

The diagnostic agent for allergoses of the present invention is used as an intracutaneous reaction diagnostic agent and titration reagent for allergy diagnosis in allergoses caused by *Malassezia* fungi. When used as an intracutaneous reaction diagnostic agent, the isolated and purified, antigenic protein of the present invention or the antigenic fragment of the present invention is dissolved in a buffer and diluted in phenol-containing physiological saline by a conventional method.

Also, when used as a titration reagent for allergy diagnosis, it can be prepared by a conventional method. For example, the isolated and purified, antigenic protein of the present invention or the antigenic fragment of the present invention may be suitably dissolved and diluted in a Hanks' buffer to be used as a histamine release titration reagent. The method can be usually carried out by the following procedures. Specifically, a given volume of blood of a patient with allergoses or a given number of blood cells prepared by suspending a fraction of blood cells obtained by centrifugation is titrated with a solution of the mentioned purified, antigenic protein as a titration reagent by measuring the amount of histamine, which is released from basophiles, upon allergen stimulation by HPLC.

The isolated and purified, antigenic protein of the present invention or the antigenic fragment of the present invention can also be used for detection and diagnosis of *Malassezia* allergoses. For example, the diagnosis can be carried out by incubating blood or a blood component sampled from a patient whose sensitivity to *Malassezia* fungi is to be assessed, together with the isolated and purified, antigenic protein of the present invention, and the like under appropriate conditions, and determining the degree of binding of the purified, antigenic protein with a blood component, including, for instance, antibody, T cell, B cell, or the like.

(5) Therapeutic Drug of Present Invention Containing as Active Ingredient Purified, Antigenic Protein or Antigenic Fragment Thereof The present invention provides a therapeutic drug for allergoses of which causative microorganisms are *Malassezia* fungi, including, as an active ingredient, an isolated and purified, antigenic protein from *Malassezia* or an antigenic fragment having at least one antigenic epitope.

The therapeutic drug of the present invention for allergoses can be administered via ordinary pathways, including, for instance, oral, intracutaneous, subcutaneous, intramuscular, and intraperitoneal pathways. Further, it can be used as percutaneous or transmucosal drugs, such as troches, sublingual tablets, eyedrops, intranasal sprays, poultices, creams, and lotions. Regarding the dosage and administration frequency of the therapeutic drug of the present invention for allergoses, the therapeutic drug can be suitably administered at a selected dose in a range of about not more than 20 mg per administration for an adult, depending on administration pathways, symptoms, and the like, and about once every week. Also, the therapeutic drug of the present invention for allergoses is useful not only as a therapeutic drug but also as a prophylactic drug for allergoses caused by *Malassezia* fungi. This is because it exhibits little or no anaphylaxis-inducing action and thus can be used safely in humans.

The therapeutic drug of the present invention for *Malassezia* allergoses contains as an active ingredient the above-described purified, antigenic protein or an antigenic fragment thereof, and is used as a therapeutic drug and prophylactic drug for various allergoses caused by *Malassezia* fungi.

The method of preparing the therapeutic drug of the present invention for allergoses is not particularly limited. For example, the purified, antigenic protein of the present invention or an antigenic fragment thereof having an epitope may be dried to a powder form and used as a hyposensitization therapeutic drug for allergoses caused by *Malassezia* fungi. In this case, it can be used alone, or in the form of a combination drug containing commonly used adjuvants and various additives, such as stabilizers, excipients, dissolution aids, emulsifiers, buffers, soothing agents, preservatives, and coloring agents, which are added by conventional methods as occasion demands. For example, a purified, antigenic protein in the powder form is dissolved in a phenol-supplemented physiological saline and used for a stock solution of an antigen for hyposensitization treatment.

In order to use it as a hyposensitization therapeutic drug, it is particularly advantageous that the therapeutic agent has an epitope that does not bind to IgE specific to *Malassezia* fungi, or even when the antigenic fragment is bound to the IgE, the binding is at a level where no histamine is released from mast cells or basophiles.

(6) Method for Quantitative Assay of *Malassezia* Allergen

The present invention also provides a method for quantitative assay of the *Malassezia* allergen. The antibody against the purified, antigenic protein from *Malassezia* can be used for an immunological quantitative analysis of the *Malassezia* allergen usable in diagnoses of allergoses or infectious diseases of which causative microorganisms are *Malassezia* fungi.

It is easy to establish a method for quantitative assay by such methods as ELISA, using, the isolated and purified, antigenic protein of the present invention or the recombinant antigenic protein descried later as a standard allergen and the antibody against the antigenic protein. Some *Malassezia* antigen extracts are commercially available, as described above. Also, because *Malassezia* fungi are commonly present on skins, including the human scalp, it is thought that commercially available house dust samples contain *Malassezia* allergens. It is extremely useful from diagnostic and therapeutic viewpoints to make known the *Malassezia* allergen contents in these commercially available antigen extracts.

(7) Recombinant *Malassezia* Antigenic Protein

The present invention provides a recombinant *Malassezia* antigenic protein (hereinafter, simply abbreviated as "recombinant antigenic protein" in some cases) having immunological properties equivalent to those of the pure, isolated and purified antigenic protein from *Malassezia* of Item (1) above, the purified, antigenic protein having a binding ability to an IgE antibody from patients with allergoses. Examples thereof include, for instance, a group of peptides comprising rMF-1 to -7 having amino acid sequences as shown by any one of SEQ ID NOs:8 to 14 (here, the term "rMF-1 to -7" means MF-1 to -7 obtained by means of a genetic recombination method), and having immunological properties equivalent to those of the above peptides. Specifically, there are included in the present invention peptides having an entire or partial amino acid sequence as shown by any one of SEQ ID NOs:8 to 14; peptides including the above peptides having immunological properties equivalent to those of each of MF-1 to -7 corresponding to rMF-1 to -7; and peptides comprising amino acid sequences, wherein the antigenic protein results from at least one of deletion, addition, insertion or substitution of one or more amino acid residues in the amino acid sequence as shown by any one of SEQ ID NOs:8 to 14, or a partial sequence thereof, wherein the antigenic protein has immunological properties equivalent to those of each of MF-1 to -7 corresponding to rMF-1 to -7.

For instance, in a case where rMF-1 is taken as an example, rMF-1 includes peptides which are antigenic proteins having immunological properties equivalent to those of MF-1, and having an entire or partial amino acid sequence as shown by SEQ ID NO:8 in Sequence Listing, or recombinant *Malassezia* antigenic proteins including the above peptide. Further, rMF-1 includes recombinant *Malassezia* antigenic proteins wherein the antigenic protein results from at least one of deletion, addition, insertion or substitution of one or more amino acid residues in the amino acid sequence as shown by SEQ ID NO:8 in Sequence Listing, or a partial sequence thereof, wherein the antigenic protein has immunological properties equivalent to those of each of MF-1 corresponding to rMF-1. The same can be said for rMF-2 to -7.

Here, the phrase "immunological properties equivalent" refers to those having equivalent *Malassezia* allergen activity, and the term "*Malassezia* allergen activity" refers to a binding ability to IgE antibodies from patients with allergoses, especially those with *Malassezia* allergoses.

The recombinant *Malassezia* antigenic protein of the present invention is obtained by, as a recombinant protein, selecting an appropriate vector so as to express the protein in bacteria, such as *Escherichia coli*, yeasts, such as budding yeasts, fungi, such as *Aspergillus*, insect cells, mammalian cells, and the like, by genetic engineering techniques using the gene of the present invention described later, preparing an expression vector, and introducing it into the above cells. The recombinant *Malassezia* antigenic protein is, therefore, essentially free of other proteins from *Malassezia*.

Functional equivalents to the recombinant antigenic protein of the present invention may be obtained by modifying the recombinant antigenic protein by known methods using mutagenesis in a specific site of the DNA encoding the recombinant antigenic protein of the present invention. For example, substitution, insertion, deletion or addition of one or more bases on the polynucleotide described later enables to make substitution, insertion, deletion or addition of an amino acid residue. It is also possible to select a mutant retaining the biological activity.

Known methods of preparing the above mutants include a gapped duplex method [*Nucleic Acids Research*, 12, 24, 9441-9456 (1984)], a deletion method [*Gene*, 33, 103-119 (1985)], a PCR method [*Gene*, 102, 67-70 (1991)], uracil DNA methods [*Methods in Enzymology*, 154, 367-382

(1987); *Proc. Natl. Acad. Sci. USA*, 79, 7258-7262 (1982)], and a cassette mutation method [*Gene*, 24, 315-323 (1985)].

A tag group may be added to the peptide chain to facilitate the purification of the recombinant antigenic protein of the present invention or to increase its solubility. An example of the tag group includes polyhistidine, which can be purified by metal affinity chromatography. Additionally, if necessary, an endoprotease-specific recognition site may be introduced between the tag group and the desired peptide, and the resulting peptide is then treated with the protease, to facilitate the isolation of the peptide free of undesirable sequences.

In order to succeed in desensitization of a patient to a peptide antigen, it is necessary to increase the solubility of the peptide by adding a functional group to the peptide, or by not including a hydrophobic T cell epitope, a hydrophobic epitope, or a hydrophobic region in the peptide. Also, in order to aid appropriate antigen processing of the T cell epitope in the peptide antigen, an endoprotease recognition site may be prepared between two regions each containing at least one T cell epitope by the above-described recombination technique or synthesis. For example, a charged amino acid pair, such as LysLys or ArgArg, may be introduced between such regions within the peptide, and the resulting peptide is sensitive to cleavage with cathepsin and/or other trypsin-like enzymes, permitting production of a peptide fragment containing 1 or more T cell epitopes. In the addition, the charged amino acid residues as described above are also capable of increasing peptide solubility.

(8) Polynucleotide Encoding Recombinant *Malassezia* Antigenic Protein of Present Invention The present invention provides a polynucleotide encoding the recombinant *Malassezia* antigenic protein, or a polynucleotide encoding antigenic fragments thereof. The polynucleotides include polynucleotides each having an entire or partial sequence of the base sequence as shown by any one of SEQ ID NOs:1 to 7 in Sequence Listing, or a polynucleotide containing the polynucleotide, wherein each of the polynucleotide encoding rMF-1 to -7 or an antigenic protein having immunological properties equivalent to these proteins. In addition, there are also included polynucleotides encoding the recombinant *Malassezia* antigenic protein, wherein the polynucleotide results from at least one of deletion, addition, insertion or substitution of one or more bases in the base sequence having an entire or partial sequence of the base sequence as shown by any one of SEQ ID NOs:1 to 7 in Sequence Listing. Further, there are included polynucleotides capable of hybridizing to the polynucleotide, wherein the polynucleotides each encodes an antigenic protein having *Malassezia* allergen activity.

For instance, in a case where rMF-1 is taken as an example, there are encompassed in the present invention polynucleotides each having an entire sequence of the base sequence as shown by SEQ ID NO:1 in Sequence Listing, or a partial sequence thereof, or a polynucleotide containing the polynucleotide, wherein each of the polynucleotide encoding rMF-1 or an antigenic protein having immunological properties equivalent to the protein. In addition, there are also encompassed in the present invention polynucleotides encoding the recombinant *Malassezia* antigenic protein, wherein the antigenic protein results from at least one of deletion, addition, insertion or substitution of one or more bases in a base sequence comprising an entire sequence as shown by SEQ ID NO:1 in Sequence Listing, or a partial sequence thereof. Further, there are included polynucleotides capable of hybridizing to the polynucleotide, wherein the polynucleotides each encodes an antigenic protein having *Malassezia* allergen activity. The same can be said for rMF-2 to -7.

The polynucleotide encoding a recombinant *Malassezia* antigenic protein can be obtained by a method as described below. It is possible to determine the N-terminal amino acid sequence or internal amino acid sequence of a *Malassezia* antigenic protein purified by a combination of various ordinary chromatographies, or that of a *Malassezia* antigenic protein purified by one-dimensional or two-dimensional electrophoresis. An oligonucleotide capable of encoding these amino acid sequences is synthesized and purified. Since one kind of amino acid is usually encoded by a number of codons, this oligonucleotide is a mixture prepared in consideration of all these codons. PCR is carried out to yield a polynucleotide of the present invention encoding the *Malassezia* antigenic protein, using this oligonucleotide and oligo(dT) as primers, and a cDNA synthesized from a total RNA or a genomic DNA extracted and purified from *Malassezia* fungi as a template. Oligonucleotides corresponding to two portions of an amino acid sequence for the antigenic protein may be used as primers for PCR, and PCR may be repeated in cases when the cDNA is not amplified by carrying out PCR once.

A polynucleotide containing the entire sequence or a polynucleotide capable of hybridizing to a polynucleotide encoding antigenic protein can easily be obtained by screening a cDNA library or genomic DNA library prepared from the poly(A)$^+$ RNA or genomic DNA of *Malassezia* fungi, using the cDNA fragment obtained by the PCR reaction as a probe for DNA hybridization. The vector used for library preparation may be of phage origin or plasmid origin.

As another method, a cDNA clone encoding a *Malassezia* antigenic protein possessing *Malassezia* allergen activity can be obtained by preparing a cDNA expression library prepared from a poly(A)$^+$ RNA of *Malassezia* fungi, and screening a clone producing the proteins that binds to the IgE antibody derived from a patient with allergoses. The protein expressed by this cDNA clone is a *Malassezia* antigenic protein.

The genes encoding the epitopes from *Malassezia* described below are also encompassed in the present invention, having sequences with a less number of bases than those in the base sequence encoding the entire amino acid sequence of a *Malassezia* allergen. Generally, although the base sequence encoding an epitope is selected from base sequences encoding mature proteins, in some cases, it is desired that a base sequence is selected to contain the leader sequence portion of the present invention. The gene of the present invention may contain a linker sequence containing a restriction endonuclease recognition site and/or a sequence useful for the cloning, expression, or purification of the desired gene. Specifically, there are encompassed in the present invention polynucleotides encoding at least one B cell epitope and having a partial sequence of any one of the base sequences shown by SEQ ID NOs:1 to 7, or polynucleotides resulting from partial modifications thereof by chemical or physical methods. For example, there are also encompassed in the present invention the corresponding polynucleotides possessed by *M. furfur* strains other than the strain used in the present invention or other fungi of the genus *Malassezia*, for example, *M. pachydermatis* and *M. sympodialis*. Specifically, *M. furfur* can be classified into five groups according to physiological properties ("Japanese Journal of Medical Mycology," Katsuhisa Uchida), each having a corresponding gene, and these genes are also encompassed in the present invention.

Moreover, the present invention includes polynucleotides capable of hybridizing to a polynucleotide having a base sequences shown by any one of SEQ ID NOs:1 to 7, or a base sequence encoding at least one B cell epitope. In the present invention, the term "capable of hybridizing" refers to a polynucleotide capable of hybridizing to another polynucleotide under the conditions shown below. A membrane on which DNA is immobilized is incubated with a probe at 50° C. for 12 to 20 hours in 6×SSC (1×SSC showing 0.15 M NaCl and 0.015 M sodium citrate, pH 7.0) containing 0.5% SDS, 0.1% bovine serum albumin (BSA), 0.1% polyvinylpyrrolidone, 0.1% Ficol 400, and 0.01% denatured salmon sperm DNA. After termination of the incubation, the membrane is washed until the signal from the immobilized DNA becomes distinguishable from the background firstly at 37° C. in 2×SSC containing 0.5% SDS, wherein the SSC concentration is changed to 0.1 fold the starting level, and wherein the temperature is changed to 50° C., and then the detection with a probe is carried out. By examining the activity owned by the protein encoded by the new DNA thus obtained in the same manner as above, whether or not the resulting DNA is the desired product can be confirmed.

Examples of polynucleotides capable of hybridizing to the gene of the present invention are shown below. The *M. furfur* TIMM2782 strain used herein has the MF-5 gene, as shown by SEQ ID NO:5, and also a gene having the putative base sequence shown in FIG. 17, which has 90% or more homology to the MF-5 gene base sequence. The proteins encoded by the two genes each has homology to dihydrolipoamide dehydrogenase (DLDH) in the known protein. This strain also has the MF-6 gene as shown by SEQ ID NO:6, and also a gene having the putative base sequence as shown in FIG. 18, which has 90% or more homology to the MF-6 gene base sequence. The proteins encoded by the two genes each has homology to malate dehydrogenase (MDH) in the known protein. Moreover, the MF-1 gene (SEQ ID NO:1) and MF-2 gene (SEQ ID NO:2) of the present invention each has 60% or more homology in terms of base sequence (FIG. 19) and are mutually capable of hybridizing. The proteins encoded by the two genes each has homology to the peroxisome membrane protein PMP-20 from *Candida boidinii*. Also, the MF-3 gene (SEQ ID NO:3) and MF-4 gene (SEQ ID NO:4) of the present invention each has 60% or more homology in terms of base sequence (FIG. 20) and are mutually capable of hybridizing. The proteins encoded by the two genes each has homology to superoxide dismutase, and actually possess its enzyme activity. Accordingly, there are also encompassed in the present invention genes capable of hybridizing to the base sequences of the present invention encoding the recombinant antigenic protein, the genes being possessed by other fungi being a causative of allergy.

The gene of the present invention is not particularly limited, and it may be DNA or RNA, natural occurring or synthetic. Useful expression vectors containing promoters, enhancers and other expression regulatory elements suited for the expression of the gene of the present invention include, for example, application of those described in "Molecular Cloning, A Laboratory Manual, 2nd edition, J. Sambrook et al., published 1989 by Cold Spring Harbor Laboratory." Recombinant proteins expressed in mammalian, yeast, fungal or insect cells can undergo modifications, such as glycosylation and appropriate disulfide bonding. Available vectors suitable for expression in yeast cells include pYES2, YepSec, and the like, which are made available. For those expressed in insect cells, the baculovirus vector is commercially available (manufactured by Pharmingen, San Diego, Calif.), and for those expressed in mammalian cells, the pMSG vector is available (manufactured by Pharmacia).

In the case of those expressed in *E. coli*, the pTV118 vector, and the like may be used. Also, when pMAL, pSEM, or pGEX is used, the gene of the present invention can be expressed as a fusion protein with maltose-binding protein, with β-galactosidase, or with glutathione S-transferase, respectively. In the case of those expressed as a fusion protein, it is especially advantageous to introduce an enzyme recognition site at the location of the fusion joint between the carrier protein and the antigenic protein from *Malassezia* or a fragment thereof. After isolating and purifying as a fusion protein, the desired antigenic protein or fragment thereof can be selectively recovered by cleavage at the enzyme recognition site and by subsequent biochemical purification using conventional methods. The enzyme recognition sites include recognition sites of blood coagulation factor Xa or thrombin, and commercial products may be used as these enzymes. It is also possible to use vectors capable of inducing expression by IPTG, temperature, or the like.

Methods for introducing an expression vector into host cells are carried out by conventional methods, such as the calcium phosphate or calcium chloride co-precipitation method, the DEAE-dextran method, or the electroporation method.

(9) Antigenic Fragment of Present Invention

The present invention provides an antigenic fragment containing at least one antigen epitope, and there are also included functional equivalent derivatives thereof. Specifically, the antigenic fragment of the present invention contains an antigen epitope contained in a recombinant *Malassezia* antigenic protein comprising an amino acid sequence as shown by any one of SEQ ID NOs:8 to 14 in Sequence Listing. The antigenic fragment of the present invention is characterized in that the antigenic fragment does not have a binding ability to IgE antibody specific to *Malassezia* fungi, or even when the antigenic fragment binds to the IgE antibody, such binding is at a level where no histamine is released from mast cells or basophiles. The antigenic fragment of the present invention is also characterized in that the antigenic fragment binds to the IgE antibody at a substantially low level as compared to an antigenic protein from *Malassezia*. The antigenic fragment of the present invention is still also characterized in that the antigenic fragment has a lower activity of activation of IgE-mediated immune response than that of the antigenic protein.

The antigenic fragments of the present invention include antigenic fragments containing at least one T cell epitope. Alternatively, there may be included antigenic fragments containing at least one B cell epitope, including, for instance, the antigenic fragments wherein the above B cell epitope is selected from the amino acid sequences as shown by one of SEQ ID NOs:42 to 44 in Sequence Listing. These antigenic fragments may be chemically synthesized by means of peptide synthesis techniques, or they may be obtained as recombinant *Malassezia* allergens from host cells transformed a plasmid having a part of the gene and expressing the desired epitope. For example, an antigenic protein may be prepared by optionally dividing the antigenic protein into non-overlapping fragments of a desired length, preferably overlapping peptide fragments of a desired length. The antigenicities of these peptide fragments are determined by assaying the binding of these peptide fragments to antibodies, or by assaying the effect on immune response, including activation of T cell responses, induction of T cell anergy, and the like.

(10) Antibody or Fragments Thereof Against Recombinant *Malassezia* Antigenic Protein of Present Invention or Antigenic Fragment Thereof The present invention provides an antibody or fragments thereof which specifically binds to the above recombinant

*Malassezia* antigenic protein or antigenic fragments thereof. The antibody of the present invention can be obtained by a conventional method, and it may be polyclonal antibodies or monoclonal antibodies. The antibody fragment is not particularly limited, as long as it specifically binds to the above recombinant *Malassezia* antigenic protein or fragments thereof.

(11) Synthetic Oligonucleotide Probe or Synthetic Oligonucleotide Primer of Present Invention The present invention provides a synthetic oligonucleotide probe and a synthetic oligonucleotide primer capable of hybridizing to the polynucleotide of the present invention. For example, there are encompassed in the present invention probes or primers containing an entire or partial sequence of the base sequences as shown by any one of SEQ ID NOs:1 to 7. The gene encoding proteins having equivalent functions can be isolated by hybridization method using the probe. This probe is prepared by, for instance, inserting the above gene or fragments thereof into an appropriate vector; introducing the vector into *E. coli* to replicate it; subsequently, extracting the replicated product from the disrupted cell solution with phenol or the like; cleaving it with a restriction endonuclease that recognizes the insertion site; carrying out electrophoresis, and cutting the desired product from the gel. The probe can also be prepared on the basis of the base sequences as shown by SEQ ID NOs:1 to 7 by chemical synthesis using DNA synthesizers or by gene amplification technique using PCR. The above probe may be labeled with a radioisotope or fluorescent substance to increase its detection sensitivity upon use.

(12) Diagnostic Agent of Present Invention Containing as Active Ingredient Recombinant *Malassezia* Antigenic Protein or Antigenic Fragment Thereof The present invention provides a diagnostic agent for *Malassezia* allergoses or *Malassezia* infections, including, as an active ingredient, the recombinant *Malassezia* antigenic protein of the present invention or the antigenic fragments thereof. The term "*Malassezia* allergoses" as used herein is defined as any allergoses of which causative microorganisms are *Malassezia* fungi, exemplified by atopic bronchial asthma, allergic rhinitis, allergic conjunctivitis, and atopic dermatitis. The term "*Malassezia* infections" is defined as any infectious disease of which causative microorganisms are *Malassezia* fungi, exemplified by tinea versicolor, *Malassezia* folliculitis, and dandruff.

The diagnostic agent for allergoses of the present invention is used as an intracutaneous diagnostic agent and titration reagent for allergy diagnosis in allergoses caused by *Malassezia* fungi. When used as an intracutaneous diagnostic agent, the recombinant antigenic protein of the present invention or the antigenic fragment of the present invention is dissolved and diluted in phenol-containing physiological saline by a conventional method.

Also, when used as a titration reagent for allergy diagnosis, it can be prepared by a conventional method. For example, the recombinant antigenic protein of the present invention or the antigenic fragment of the present invention may be suitably dissolved and diluted in a Hanks' buffer to be used as a histamine release titration reagent. The method can be usually carried out by the following procedures. Specifically, a given volume of blood of a patient with allergoses or a given number of blood cells prepared by suspending a fraction of blood cells obtained by centrifugation is titrated with a solution of the mentioned recombinant antigenic protein as a titration reagent by measuring the amount of histamine, which is released from basophiles, upon allergen stimulation by HPLC.

The recombinant antigenic protein of the present invention or the antigenic fragment of the present invention can also be used for detection and diagnosis of *Malassezia* allergoses. For example, the diagnosis can be carried out by incubating blood or a blood component sampled from a patient whose sensitivity to *Malassezia* fungi is to assessed, together with the isolated and purified, antigenic protein of the present invention, and the like under appropriate conditions, and determining the degree of binding of the purified, antigenic protein with a blood component, including, for instance, antibody, T cell, B cell, or the like.

(13) Therapeutic Drug Containing Recombinant *Malassezia* Antigenic Protein or Antigenic Fragments of Present Invention as Active Ingredient The present invention provides a therapeutic drug for *Malassezia* allergoses or *Malassezia* infections including, as an active ingredient, the recombinant *Malassezia* antigenic protein or its antigenic fragments of the present invention. When the antigenic fragment from *Malassezia* is used for therapeutic purposes, it is preferred that the antigenic fragment binds to its IgE at concentrations substantially lower than the naturally occurring *Malassezia* allergen, and that mediators are not released from mast cells or basophiles upon binding. More preferably, the antigenic fragment exhibits activity to activate T cell response and/or is capable of inducing T cell anergy. A recombinant *Malassezia* antigenic protein or antigenic fragments thereof can be assessed in in vitro tests, such as RAST method, ELISA method, and histamine release tests, as well as in skin tests and intracutaneous tests in laboratory animals or human volunteers.

The recombinant antigenic protein of the present invention and the gene therefor can be utilized for therapeutic drugs for *Malassezia* allergoses. The therapeutic drug includes, as an active ingredient, the above-described recombinant *Malassezia* antigenic protein, antigenic fragments thereof, or a peptide having an epitope, so that it can be utilized for therapeutic drugs for various allergoses caused by *Malassezia* fungi. Moreover, the above-described gene can also be utilized for a therapeutic drug, in which case the gene is inserted into a vector expressible in a mammal and administered in the form of a DNA molecule or viral particles having the gene in a suitable viral vector. By this administration, tolerance can be induced to treat diseases.

The method of preparing the therapeutic drug of the present invention for allergoses is not particularly limited. For example, the recombinant *Malassezia* antigenic protein prepared by the above method, or antigenic fragments thereof, or a peptide having an epitope, or a DNA molecule having a vector to which the above gene is inserted may be dried to a powder form and used as a hyposensitization therapeutic drug for allergoses caused by *Malassezia* fungi. When the therapeutic drug of the present invention for allergoses is used as a hyposensitization therapeutic drug, it can be used alone, or in the form of a combination drug containing commonly used adjuvants and various additives, such as stabilizers, excipients, dissolution aids, emulsifiers, buffers, soothing agents, preservatives, and coloring agents, which are added by conventional methods as occasion demands. For example, a purified, recombinant antigenic protein in the powder form is dissolved in a phenol-supplemented physiological saline and used for a stock solution of an antigen for hyposensitization treatment.

The therapeutic drug of the present invention for allergoses can be administered via ordinary pathways, including, for instance, oral, intracutaneous, subcutaneous, intramuscular, and intraperitoneal pathways. Further, it can be used as percutaneous or transmucosal drugs, such as troches, sublingual tablets, eyedrops, intranasal sprays, poultices, creams, and lotions. Regarding the dosage and administration frequency of the therapeutic drug of the present invention for allergoses, the administration of the therapeutic drug can be suitably selected so that the therapeutic drug is administered at a dose of about not more than 20 mg per administration for an adult, depending on administration pathways, symptoms, and the like, and about once every week. Also, the therapeutic drug of the present invention for allergoses is useful not only as a therapeutic drug but also as a prophylactic drug for *Malassezia* allergoses. This is because it exhibits little or no anaphylaxis-inducing action and thus can be used safely in humans.

The therapeutic drug of the present invention for *Malassezia* allergoses contains as an active ingredient the above-described recombinant, antigenic protein or antigenic fragments thereof, and is used as a therapeutic drug and prophylactic drug for various *Malassezia* allergoses. In order to use it as a hyposensitization therapeutic drug, it is particularly advantageous that the therapeutic agent has an epitope that does not bind to IgE specific to *Malassezia* fungi, or even when the antigenic fragment binds to the IgE, the binding is at a level where no histamine is released from mast cells or basophiles.

The present invention is hereinafter described in more detail by means of the following working examples and comparative examples, without intending to limit the scope of the present invention thereto.

EXAMPLE 1

Isolation and Physicochemical Properties of Antigenic Protein from *Malassezia*

1-1) Preparation of *Malassezia* Partially Purified Crude Antigen 2782

The culture was obtained by subjecting the *M. furfur* TIMM2782 strain (FERM BP-5611) to shaking culture at 27° C. for 5 days in fifty (50) 500 ml conical flasks each containing 150 ml of Dixon medium (6.0% bacto malt extract broth, 2.0% Bacto Oxgall, 1.0% Tween 40, 0.25% glycerol α-monooleic acid). From the resulting culture, cells were harvested by centrifugation. The cells were washed with a phosphate-buffered saline (PBS) five times, and the cells were then suspended in PBS in an amount double the wet weight of the cells, and disrupted and extracted by adding an equal amount of glass beads 0.5 mm in diameter, and using the MSK cell homogenizer (manufactured by B. Brown). The cell disruption extract obtained was centrifuged (18,000 rpm, 30 min), and the supernatant was obtained. The resulting supernatant was dialyzed against purified water and sterilized by filtration through a 0.45 μm membrane filter, followed by freeze-drying, to give about 900 mg of the *Malassezia* crude antigen 2782.

About 800 mg of the above *Malassezia* crude antigen 2782 was dissolved in a 0.05 M Tris-HCl buffer (pH 8.0) and subjected to ammonium sulfate salting-out. The fraction precipitated on ammonium sulfate from 50% to 90% saturation was collected by centrifugation, and the collected fraction was dissolved in a 0.05 M Tris-HCl buffer (pH 8.0), and the solution was subsequently dialyzed against the same buffer to give the *Malassezia* partially purified crude antigen 2782.

1-2) Screening for Antigenic Proteins from *Malassezia*

After freeze-drying, the *Malassezia* partially purified crude antigen 2782 was dissolved in a 0.1 M potassium phosphate buffer (pH 7.0) containing 2 M ammonium sulfate so as to give a 4 mg/ml solution. Thereafter, 100 μl of the solution was applied to a column of Phenyl Superose PC 1.6/5 (column volume: 0.1 ml, manufactured by Pharmacia), previously equilibrated with the same buffer (pH 7.0) containing 2 M ammonium sulfate, and the elution was carried out with the same 0.1 M buffer on a linear gradient from 2 M to 0 M ammonium sulfate. The antigenic protein-containing fraction obtained was dialyzed against a Bis-Tris buffer (pH 6.5), and the dialyzed fraction was then applied to a column of Mono Q PC 1.6/5 (column volume: 0.1 ml, manufactured by Pharmacia), and the elution was carried out with the same buffer on a linear gradient from 0 M to 0.3 M sodium chloride (FIG. 1, flow rate: 100 μl/min, detection: 280 nm). The eluate was divided into 26 fractions of 50 μl each, and the binding ability of IgE antibody was then examined for Fractions 1 through 20 by the Direct RAST (EIA) method using sera from patients.

Figure 2:
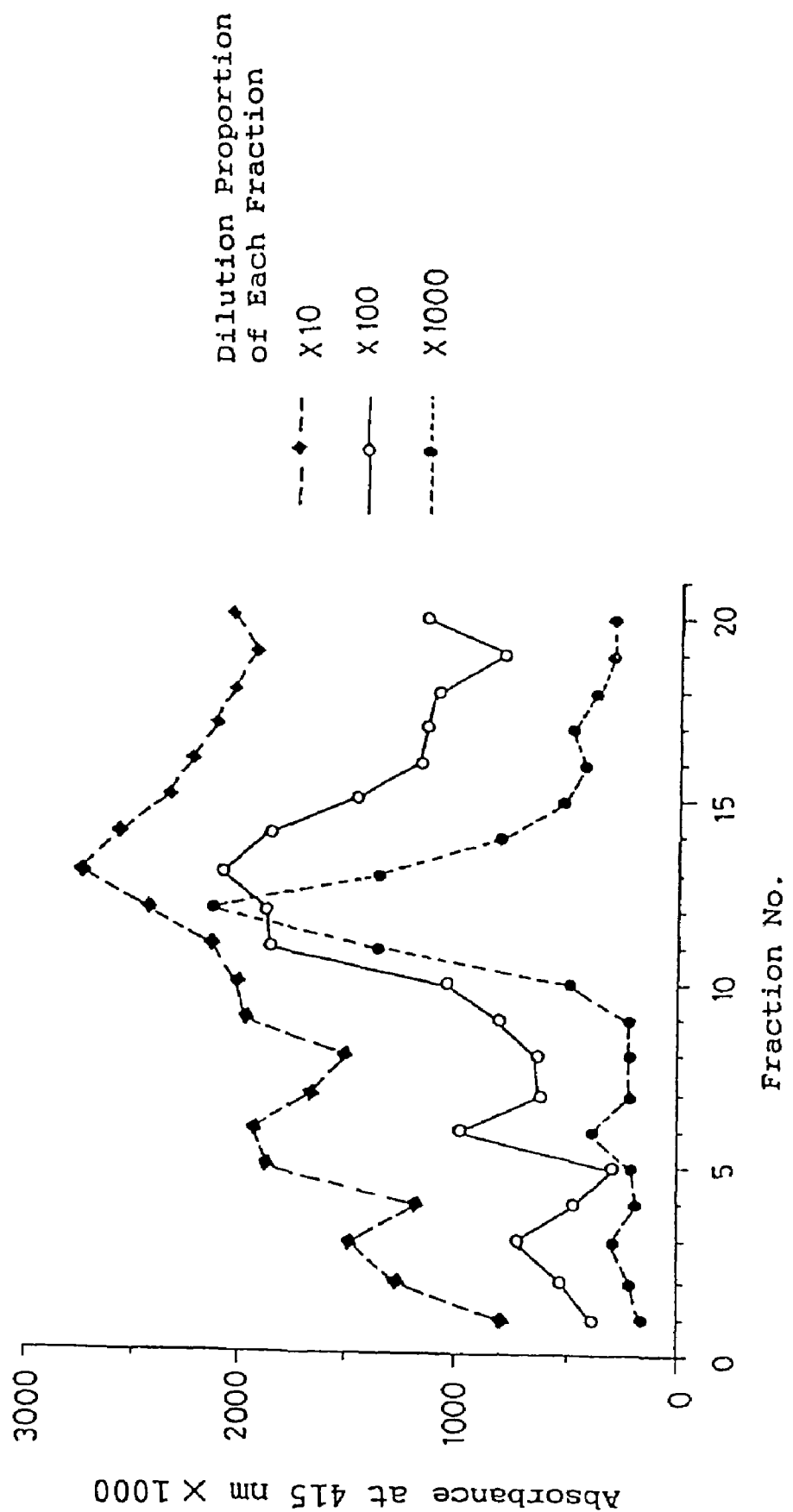
FIG. 2 is a graph showing the binding ability of Mono Q fractions of a partially purified, crude antigen 2782 of *Malassezia* with an IgE antibody in a patient serum.

Specifically, each fraction was diluted 10 folds, 100 folds, and 1,000 folds with a 0.1 M borate buffer (pH 8.0) containing 0.01% Tween 20, and 45 μl of each dilution was coupled to a paper disc activated with cyanogen bromide and subsequently blocked with ethanolamine. Thereafter, each disc was supplemented with 50 μl of a 5-fold dilution of pooled sera (collection of sera from 10 patients showing high values in RAST method), followed by reaction with a diluted β-galactosidase-labeled goat anti-human IgE antiserum. Thereafter, an enzyme substrate was added thereto, followed by absorbance measurement at 415 nm. The results are shown in FIG. 2. It is clear from FIG. 2 that there are a plurality of allergenic proteins. For example, a protein that binds to patient IgE is present in the neighborhoods of Fraction 6, and Fractions 12 and 13.

Figure 3:
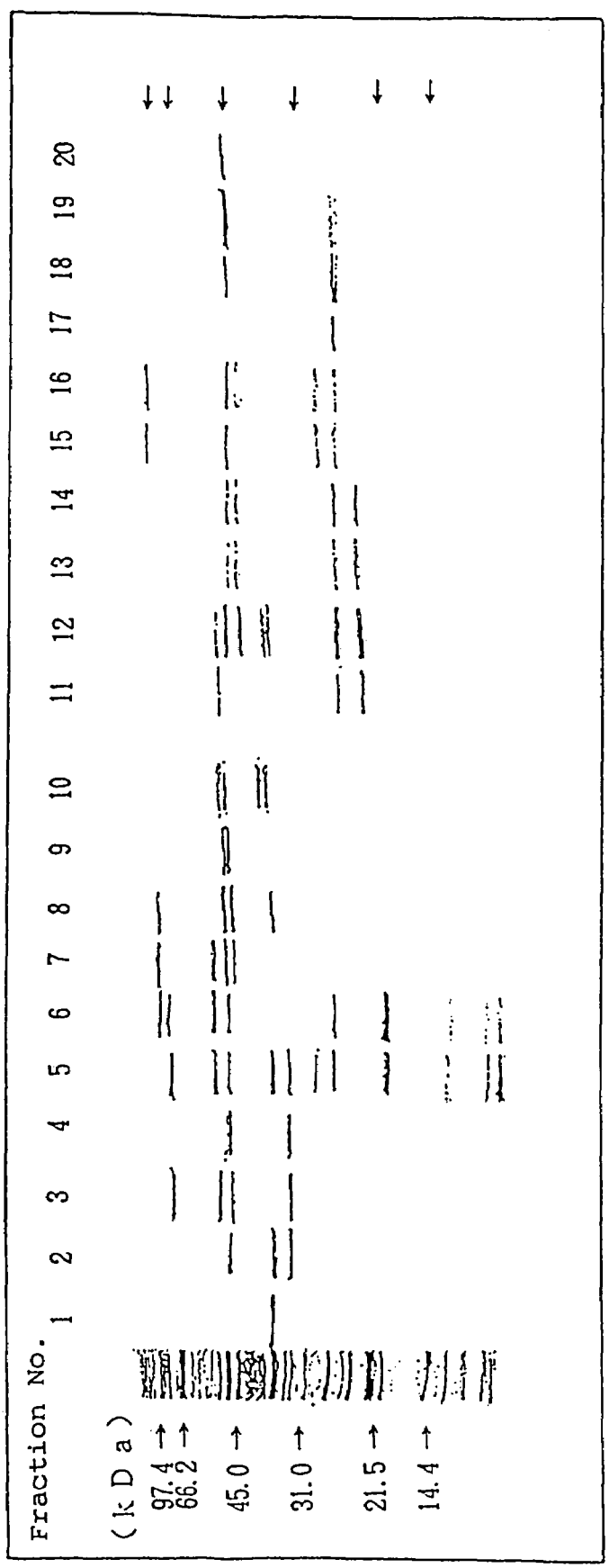
FIG. 3 is an electrophoretic analysis obtained by subjecting Mono Q fractions of a partially purified, crude antigen 2782 of *Malassezia* to SDS-PAGE, and then staining with CBB.

Separately, each fraction was subjected to SDS-PAGE, and it was stained with Coomassie Brilliant Blue (CBB) to detect proteins (FIG. 3), and the representative fractions were subjected to immunoblotting as described below.

Figure 4:
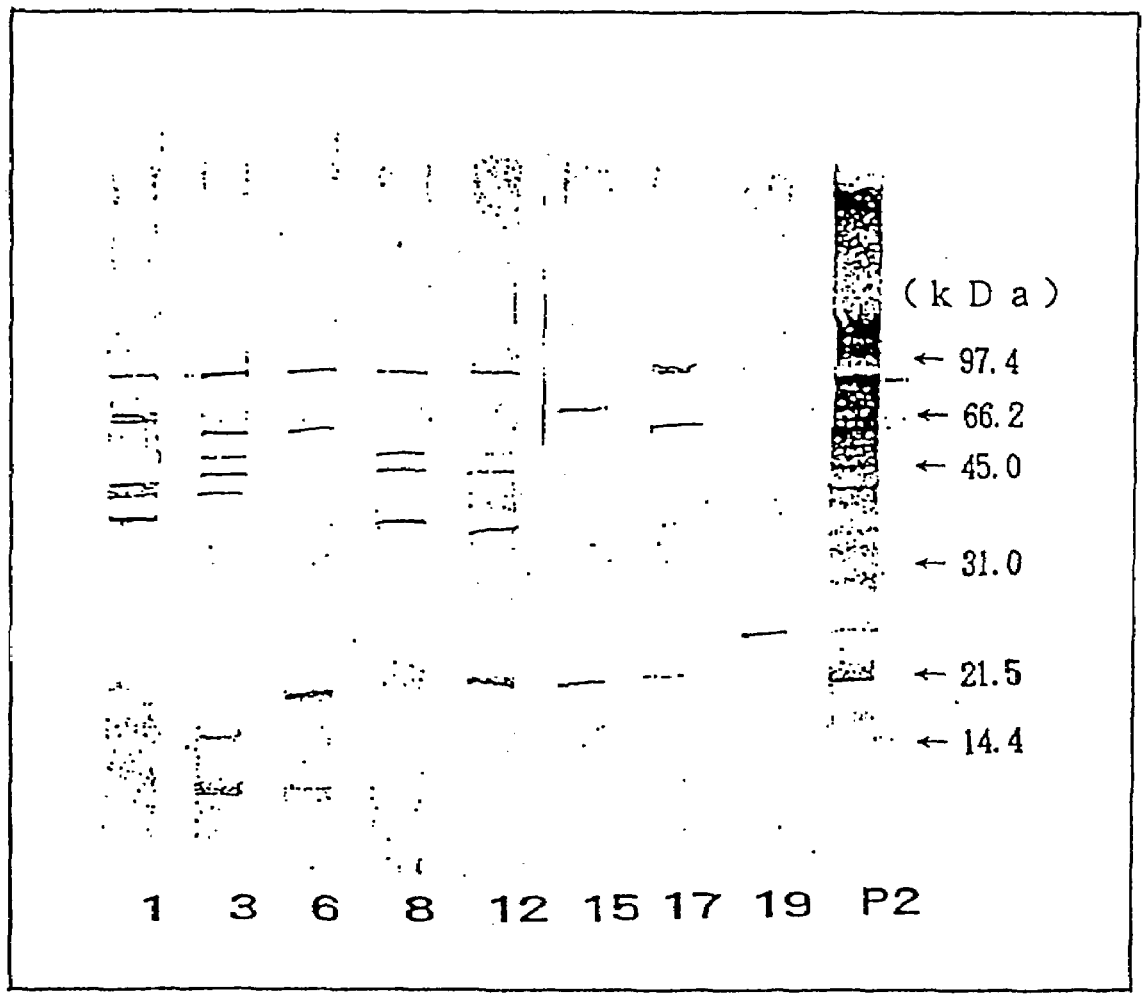
FIG. 4 is an electrophoretic analysis obtained by subjecting Mono Q fractions of a partially purified, crude antigen 2782 of *Malassezia* to SDS-PAGE, and then conducting immunoblotting.

Specifically, each fraction was subjected to SDS-PAGE, and it was then transferred onto a nitrocellulose membrane, blocked with 3% bovine serum albumin (BSA), and treated with pooled sera from patients. Thereafter, the fraction was reacted with a diluted alkaline phosphatase-labeled goat anti-human IgE antiserum, and an enzyme substrate was then added, followed by detection of allergenic protein. As a result, it is made clear from FIG. 4 that there are a plurality of allergenic proteins. For example, it is evident that Fraction 12 contains a protein detected in the neighborhood of 20 kDa on SDS-PAGE (isolated as an allergen MF-1), and the like, as allergenic proteins. It is also evident that Fraction 6 contains an allergenic protein having a molecular weight of 20 kDa, nearly equal to that of Fraction 12 (isolated as an allergen MF-2), and another protein detected in the neighborhood of 80 kDa, and the like.

1-3) Isolation of Purified Antigenic Proteins MF-1, MF-2, MF-3, MF-4, and MF-13

After 0.25 mg of a freeze-dried product of the above-described *Malassezia* partially purified crude antigen 2782 was dissolved in 1 ml of a Bis-Tris buffer (pH 6.5) solution, the resulting solution was applied to a column of Mono Q HR 5/5 (column volume: 1 ml, manufactured by Pharmacia) in the same manner as the Mono Q chromatography described under Item 1-2) above, resulting in four peaks, namely Peak 1 (corresponding to Fractions 5 and 6 in FIG. 1), Peak 2 (corresponding to Fractions 10, 11, and 12 in FIG. 1), Peak 3

(corresponding to Fractions 15 and 16 in FIG. 1), and Peak 4 (corresponding to Fractions 18, 19, and 20 in FIG. 1). Each peak was subjected to gel filtration chromatography, hydrophobic chromatography, and finally ion exchange chromatography by Mono Q, to isolate pure antigenic proteins, wherein the protein named MF-2 was isolated from Peak 1, that named MF-1 isolated from Peak 2, that named MF-3 isolated from Peak 3, and that named MF-4 isolated from Peak 4. Separately, the Mono Q, non-adsorbed fraction of the *Malassezia* partially purified antigen 2782 was subjected to hydrophobic chromatography to isolate a pure antigenic protein named MF-13. It was confirmed that the five isolated proteins were *Malassezia* allergen proteins by examining their binding ability of IgE antibody by EIA method using the above-described pooled sera from patients.

Figure 5:
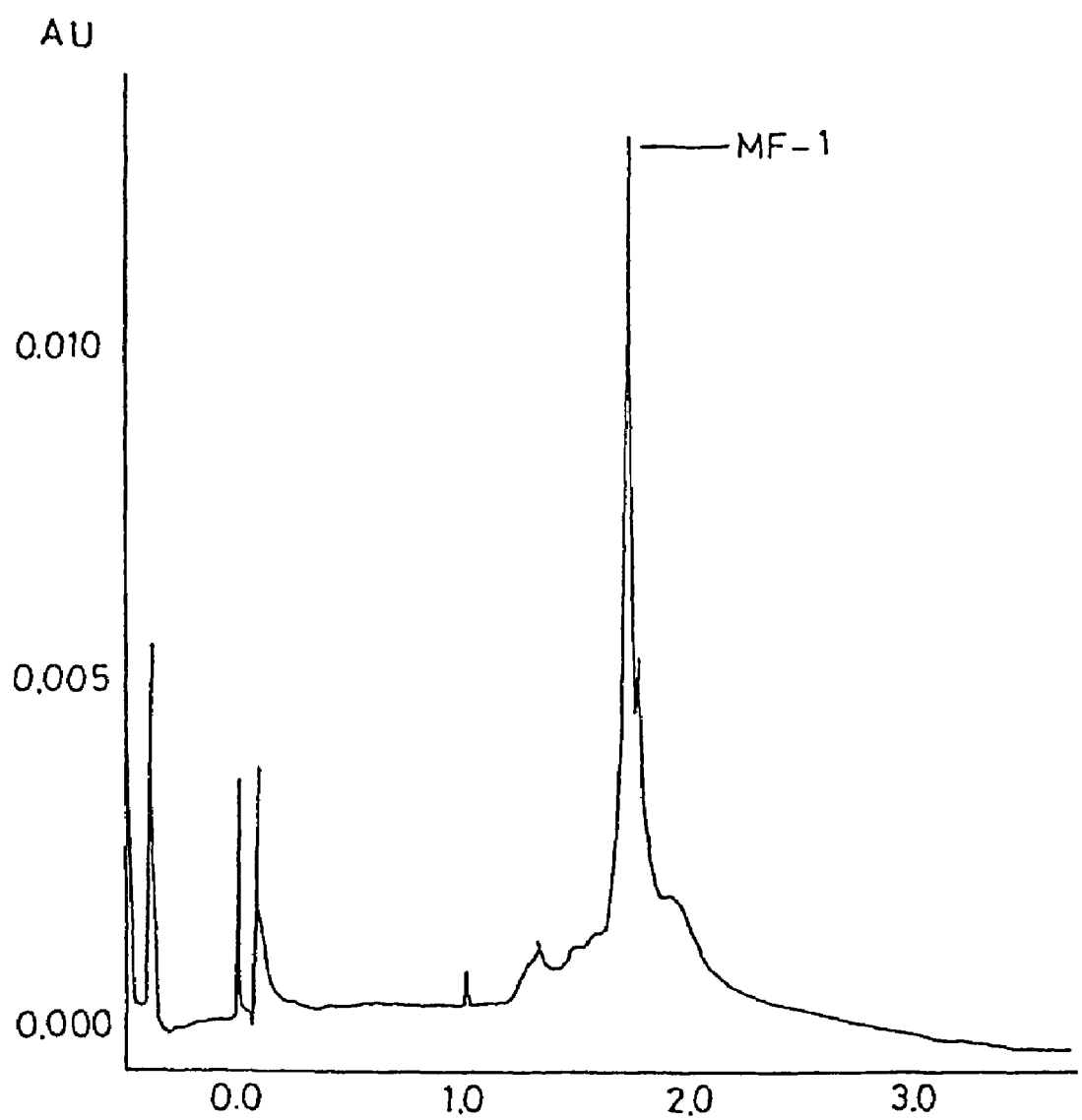
FIG. 5 is a chart showing an MF-1 peak by Mono Q chromatography.
Figure 6:
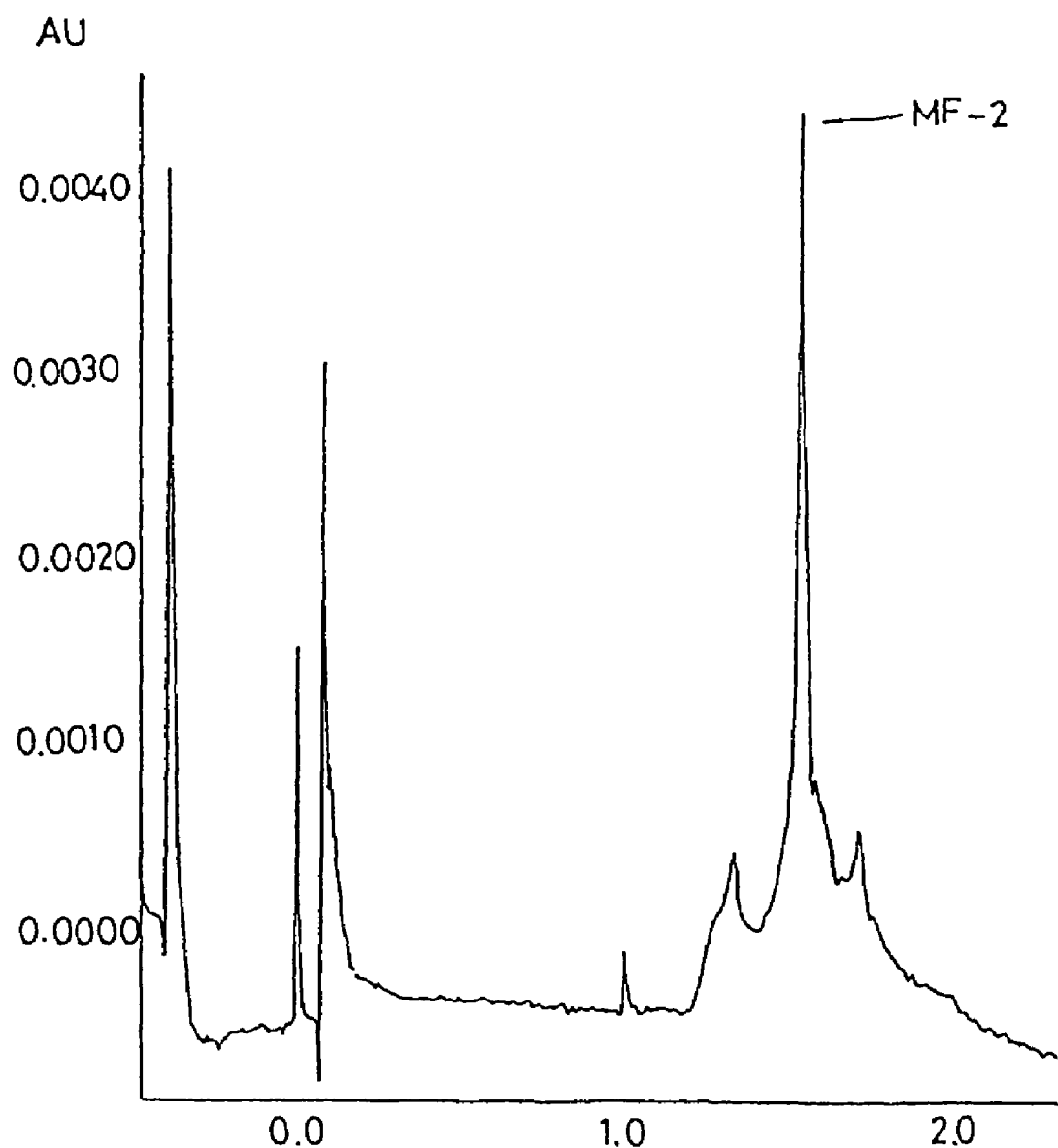
FIG. 6 is a chart showing an MF-2 peak by Mono Q chromatography.
Figure 7:
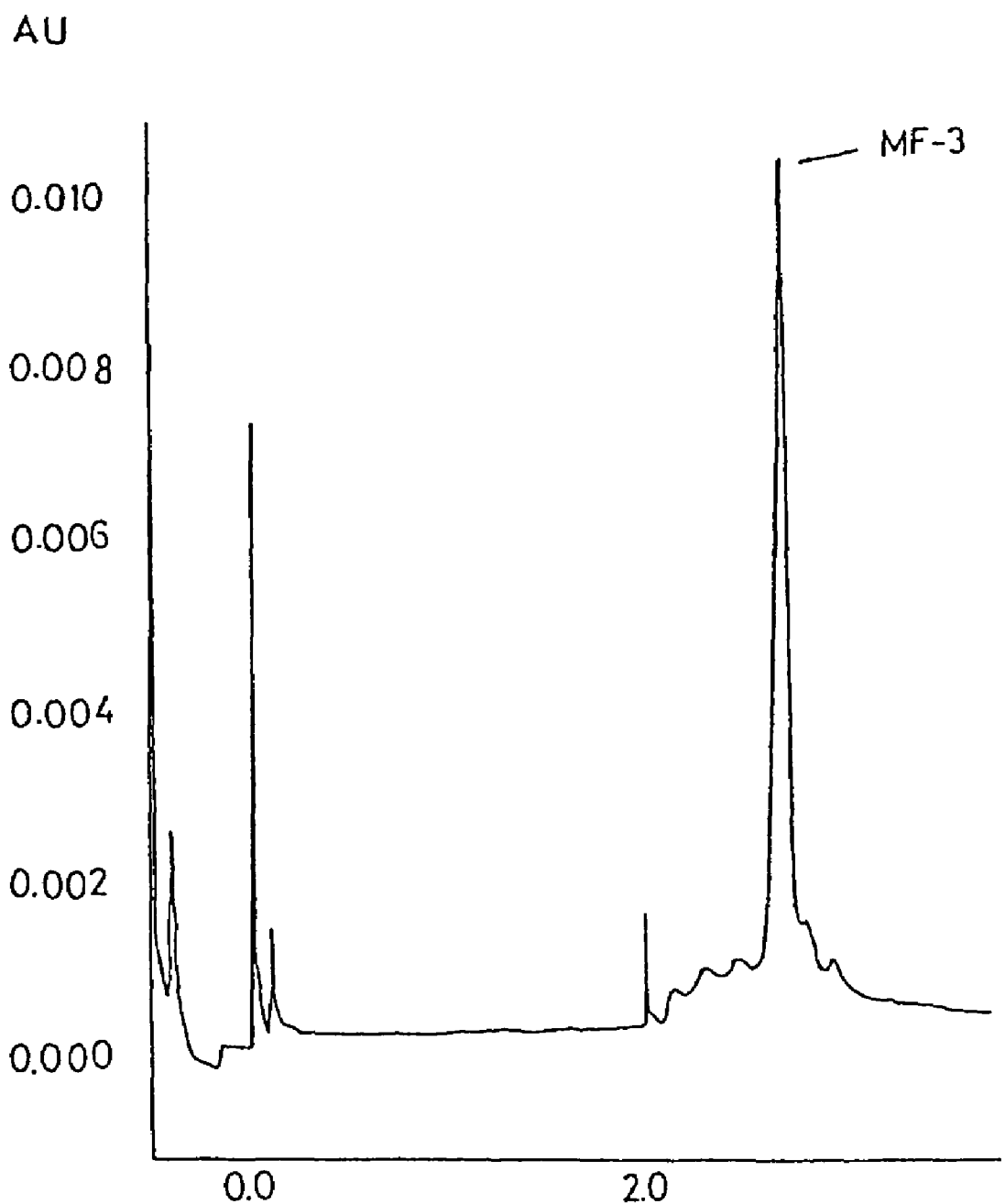
FIG. 7 is a chart showing an MF-3 peak by Mono Q chromatography.
Figure 8:
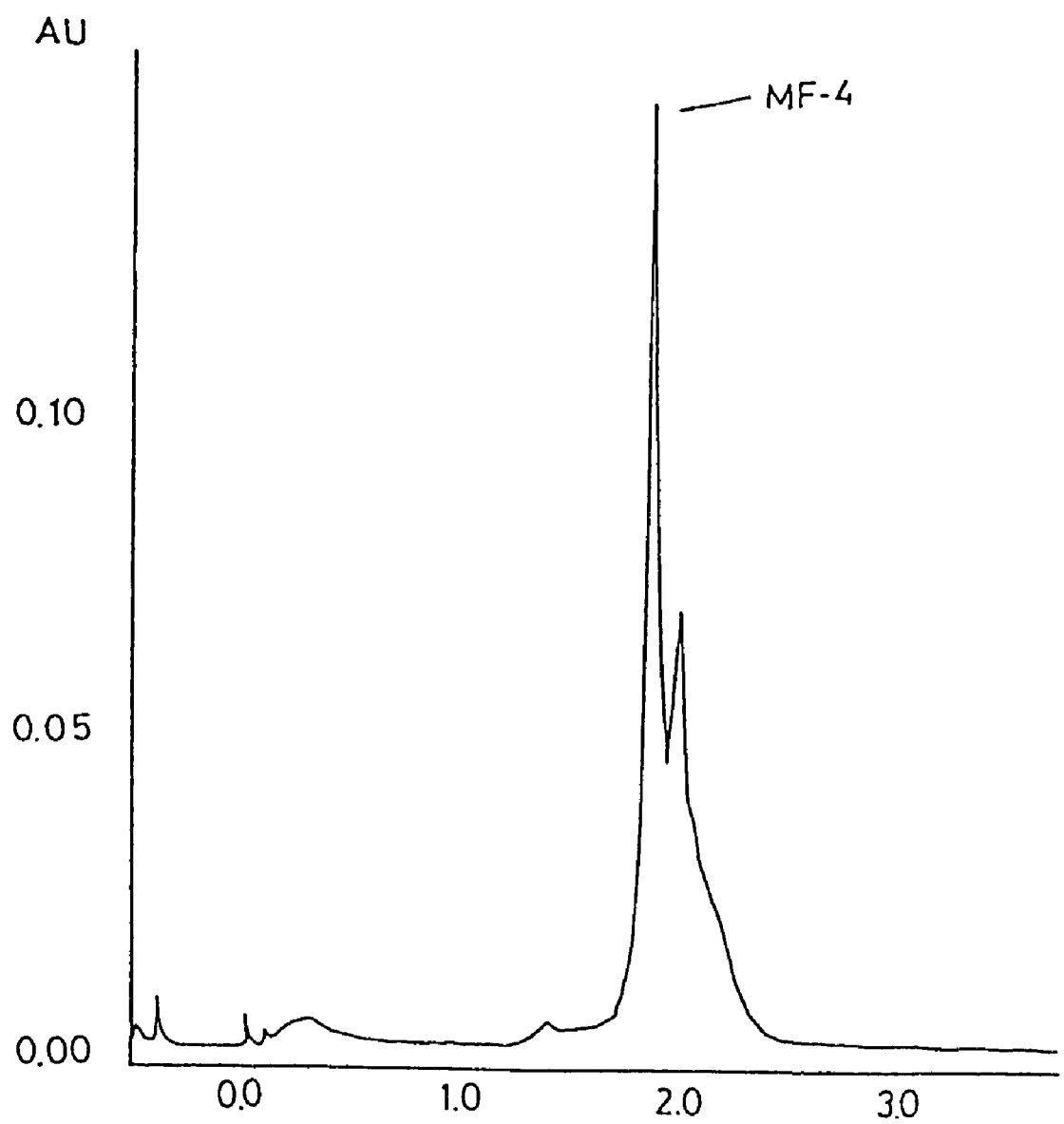
FIG. 8 is a chart showing an MF-4 peak by Mono Q chromatography.
Figure 24:
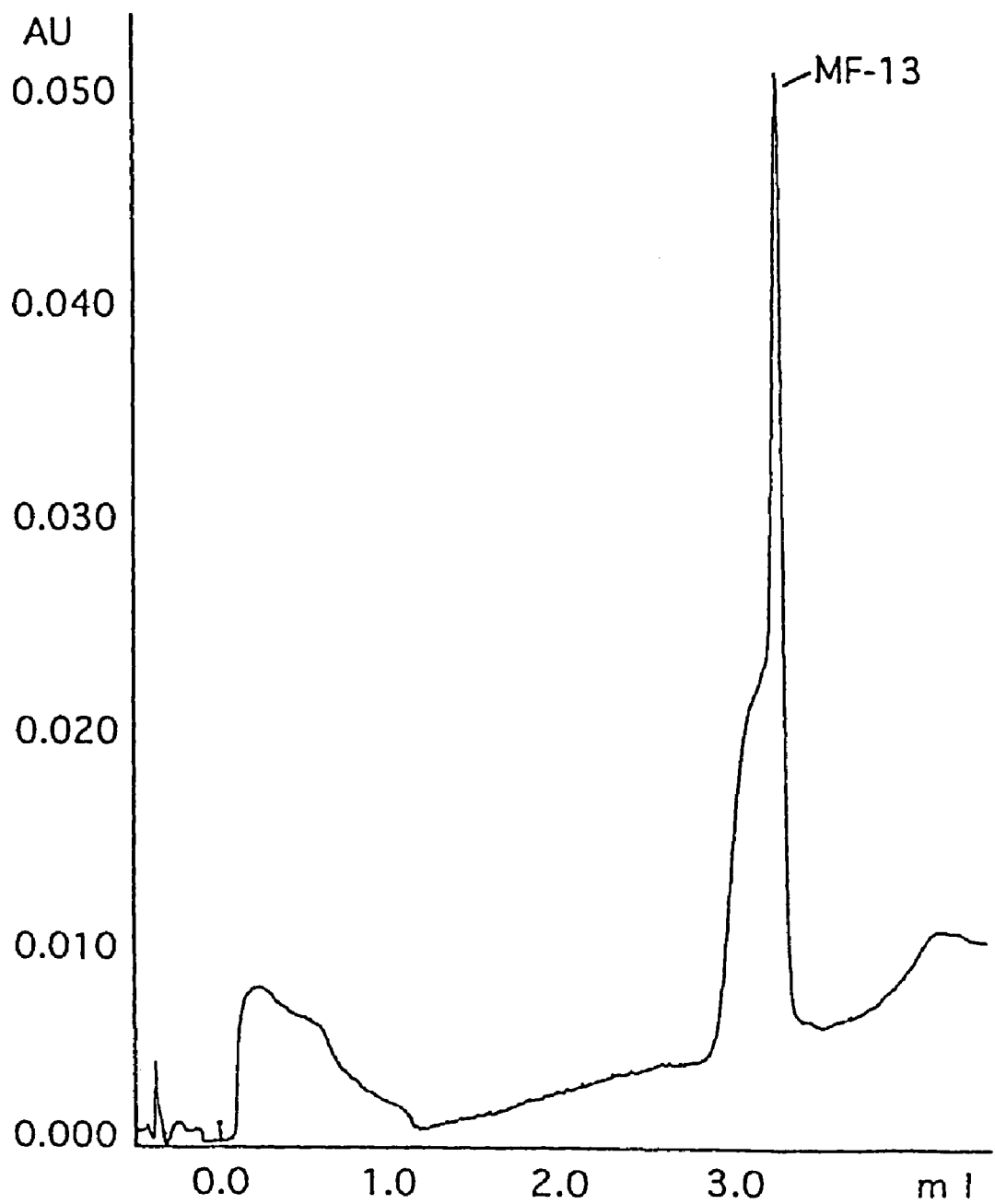
FIG. 24 is a chart showing MF-13 peak obtained by Phenyl Superrose chromatography.

The purification method used is described in detail. Peaks 1 through 4 as separated from Mono Q were each diluted 2 folds with a 0.1 M potassium phosphate buffer (pH 7.0) containing 4 M ammonium sulfate, and thereafter, the dilution was applied to a column of Phenyl Superose PC 1.6/5 (column volume: 0.1 ml, manufactured by Pharmacia), previously equilibrated with a 0.1 M potassium phosphate buffer (pH 7.0) containing 2 M ammonium sulfate, and the elution was carried out with the same 0.1 M buffer on a linear gradient from 2 M to 0 M ammonium sulfate. The antigenic protein-containing fraction obtained was concentrated using an ultrafiltration membrane (MW 10,000), and the resulting concentrate was then subjected to gel filtration chromatography using the Sephadex G-75 Superfine column (1.5×100 cm) to obtain a fraction eluted at a molecular weight of about 40,000. The gel filtration product obtained was further subjected to ion exchange chromatography using a column of Mono Q PC 1.6/5, and elution was carried out in the same manner as above to isolate antigenic proteins. In other words, MF-1 was isolated from Peak 2 (FIG. 5); MF-2 was isolated from Peak 1 (FIG. 6); MF-3 was isolated from Peak 3 (FIG. 7); and MF-4 was isolated from Peak 4 (FIG. 8). Separately, the Mono Q non-adsorbed fraction was applied to the same column of Phenyl Superose PC 1.6/5 (column volume: 0.1 ml, manufactured by Pharmacia), and the elution was carried out with the same 0.1 M buffer on a linear gradient from 2 M to 0 M ammonium sulfate (FIG. 24) to isolate a pure, antigenic protein named MF-13.

1-4) Identification of MF-1 through MF-4 by Two-Dimensional Electrophoresis and Isolation of Purified, Antigenic Proteins MF-5 Through MF-12

Figure 9:
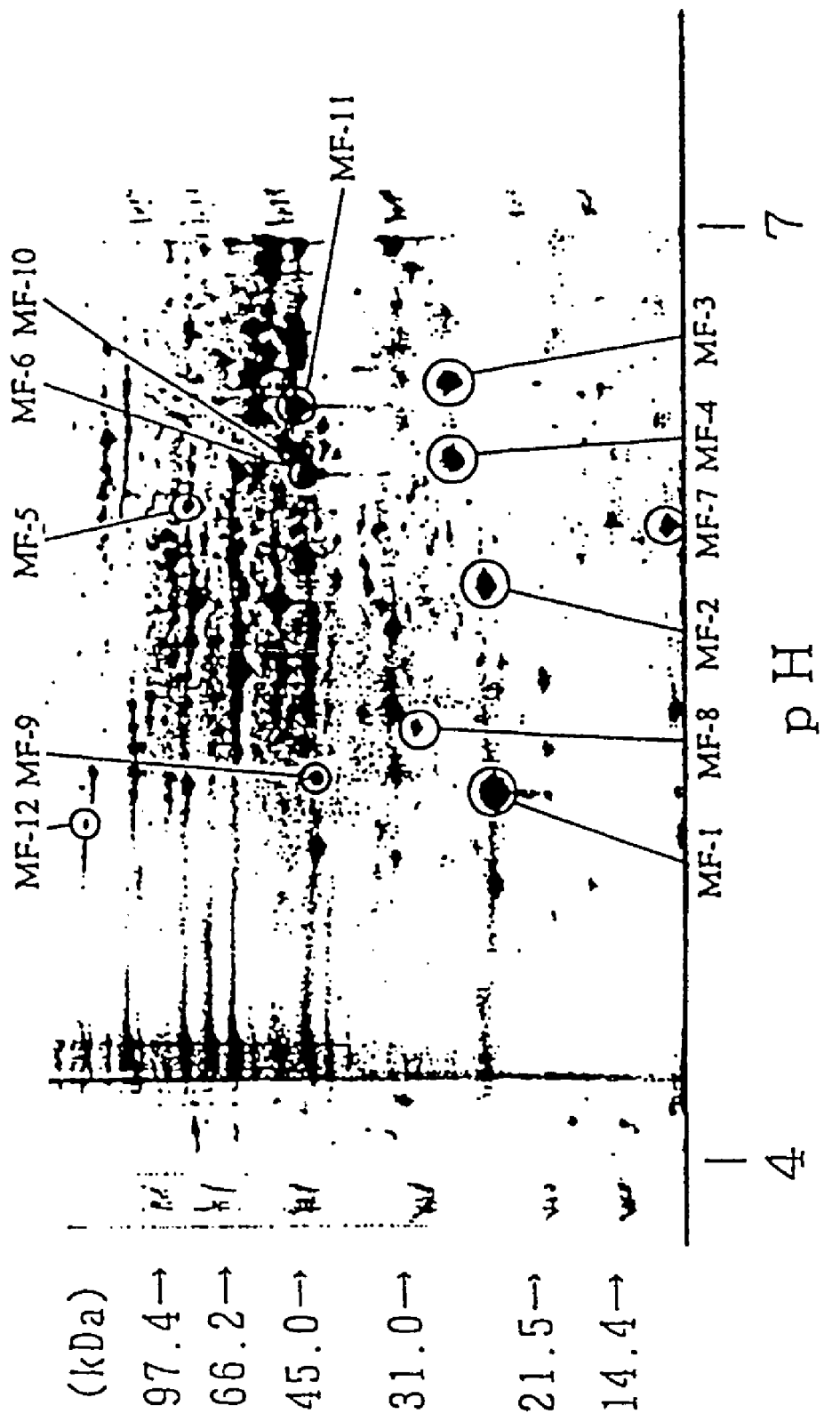
FIG. 9 is a two-dimensional electrophoretic analysis of a crude antigen 2782 of *Malassezia*. Here, the protein is detected by staining with Coomassie brilliant blue.
Figure 10:
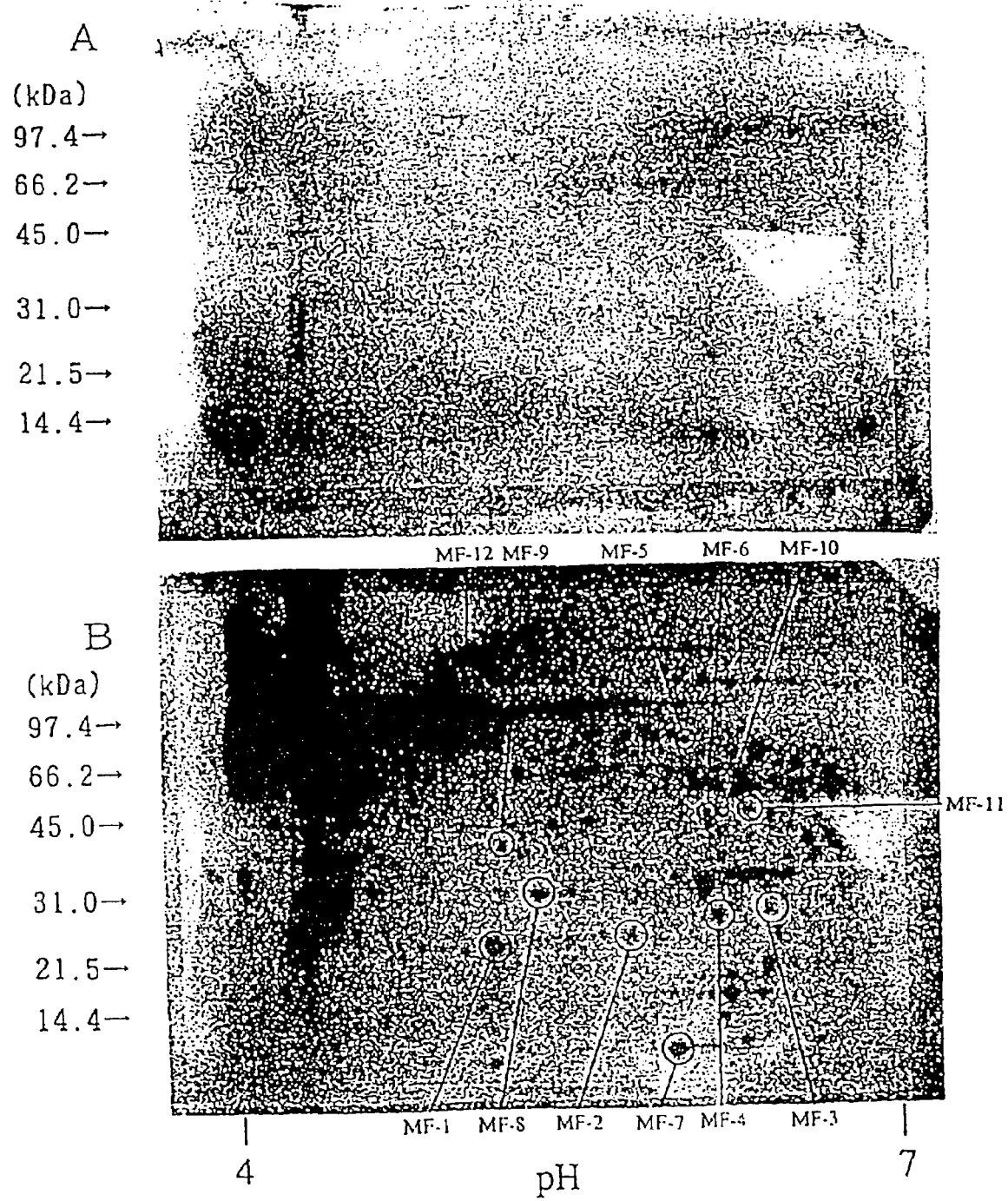
FIG. 10 is a two-dimensional electrophoretic analysis of crude antigen 2782 of *Malassezia*. Here, spots are detected by immunoblotting method using an IgE antibody (A) of a normal individual and an IgE antibody (B) of an allergic patient.

Further, 150 µg of the above-described *Malassezia* partially purified crude antigen 2782 was dissolved in a solution containing 8 M urea, 0.5% NP-40, 2% β-mercapto-ethanol, 0.8% Pharmalyte (manufactured by Pharmacia), and 0.01% Bromophenol Blue. First-dimensional isoelectric electrophoresis was carried out by a conventional method using the Immobiline DryStrip gel (pH 4-7, manufactured by Pharmacia). Second-dimensional SDS-PAGE was carried out using the ExelGel SDS-Homogeneous (12.5%, manufactured by Pharmacia), followed by protein detection by CBB staining (FIG. 9). After protein transfer onto a PVDF membrane (manufactured by Millipore), immunoblotting was carried out using sera from patients with allergoses (IgE antibodies) with a positive response to the crude antigen in skin test and a high value in RAST method, and normal individual sera (IgE antibodies) to detect positive spots (FIG. 10). Of the positive spots found, those judged to have high positive rate, namely, one having a molecular weight of about 21 kDa and an isoelectric point of about 5.3; one having a molecular weight of about 20 kDa and an isoelectric point of about 5.8; one having a molecular weight of about 27 kDa and an isoelectric point of about 6.5; and one having a molecular weight of about 26 kDa and an isoelectric point of about 6.3 were identified as MF-1, MF-2, MF-3, and MF-4, respectively, based on the results of N-terminal sequencing, and the like. Also detected were proteins having a molecular weight of about 66 kDa and an isoelectric point of about 6.1 (named MF-5); a molecular weight of about 43 kDa and an isoelectric point of about 6.2 (named MF-6); a molecular weight of about 15 kDa and an isoelectric point of about 6.0 (named MF-7); a molecular weight of about 30 kDa and an isoelectric point of about 5.4 (named MF-8); a molecular weight of about 40 kDa and an isoelectric point of about 5.3 (named MF-9); a molecular weight of about 44 kDa and an isoelectric point of about 6.2 (named MF-10); a molecular weight of about 45 kDa and an isoelectric point of about 6.4 (named MF-11); and a molecular weight of about 100 kDa and an isoelectric point of about 5.0 (named MF-12) as proteins binding to the IgE antibodies of the patients with allergoses. These proteins were extracted from the gel and isolated.

1-5) Physicochemical Properties of Purified, Antigenic Proteins MF-1, MF-2, MF-3, MF-4, MF-5, MF-6, MF-7, MF-8, MF-9, MF-10, MF-11, MF-12, and MF-13

Figure 11:
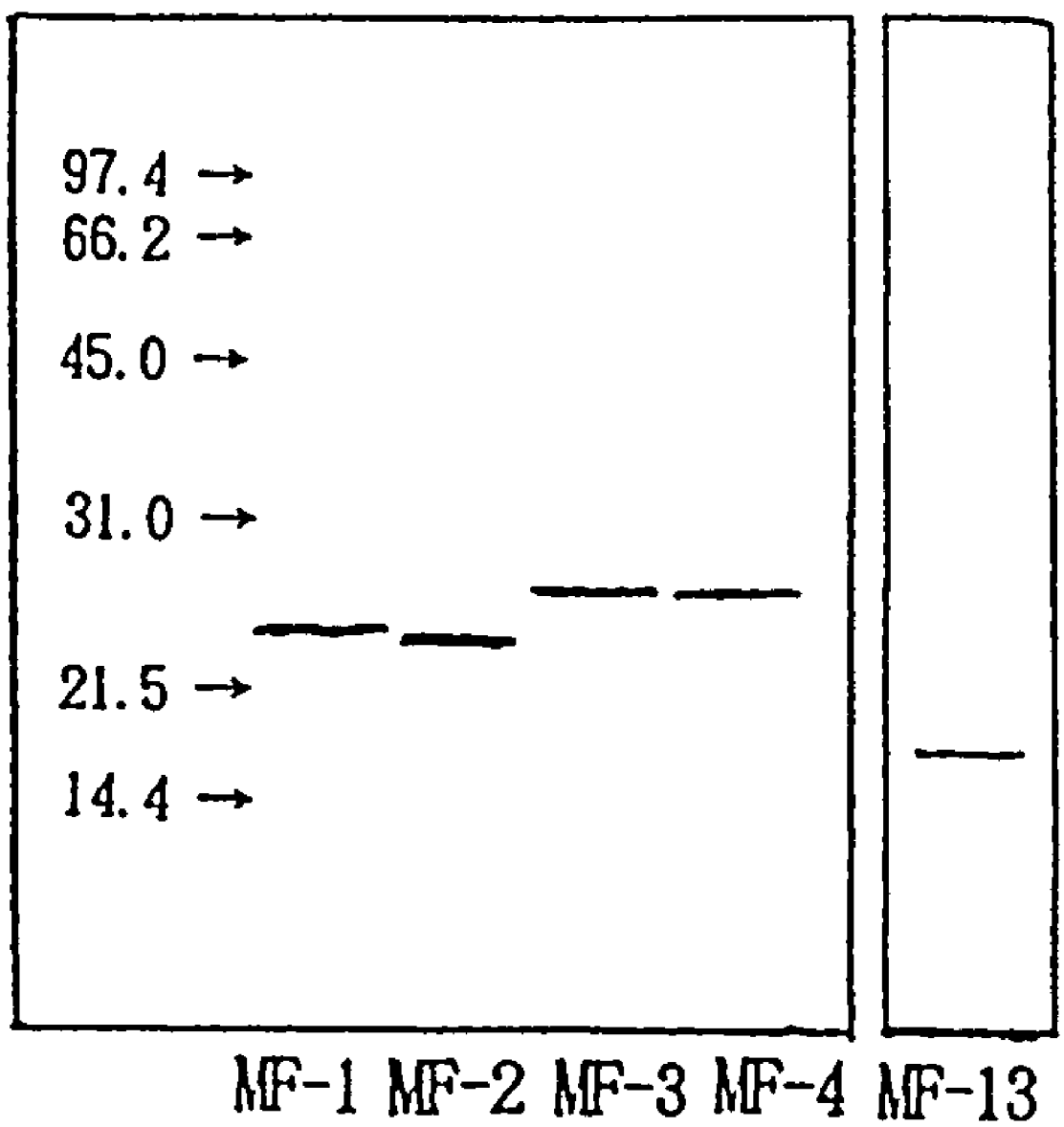
FIG. 11 is an electrophoretic analysis using SDS-PAGE (under reduced conditions) of MF-1, MF-2, MF-3, MF-4, and MF-13.

The isolated MF-1, MF-2, MF-3, MF-4, and MF-13 each showed a single band in SDS-PAGE (FIG. 11). The results of analysis by SDS-PAGE and isoelectric electrophoresis of MF-1 through MF-13 are shown in Table 1. Isoelectric electrophoresis of MF-1 through MF-4 in non-denatured form was carried out by a conventional method using IsoGel Plate at pH 3-10 (manufactured by FMC). The results of analysis of SDS-PAGE and isoelectric electrophoresis of MF-5 through MF-12 were calculated from the results of two-dimensional electrophoresis shown in FIG. 9.

TABLE 1

| | SDS-PAGE (kDa) | | |
|---|---|---|---|
| | Under Reduced Conditions[1] | Under Non-Reduced Conditions | Isoelectric Point[2] |
| MF-1 | 21 | 40 | 4.7 (5.3) |
| MF-2 | 20 | 40 | 4.8 (5.8) |
| MF-3 | 27 | 27 | 5.2 (6.5) |
| MF-4 | 26 | 26 | 5.2 (6.3) |
| MF-5 | 66 | — | — (6.1) |
| MF-6 | 43 | — | — (6.2) |
| MF-7 | 15 | — | — (6.0) |
| MF-8 | 30 | — | — (5.4) |
| MF-9 | 40 | — | — (5.3) |
| MF-10 | 44 | — | — (6.2) |
| MF-11 | 45 | — | — (6.4) |
| MF-12 | 100 | — | — (5.0) |
| MF-13 | 16 | — | 8.1 |

[1]Reduction: Treated with 3% of mercaptoethanol.
[2]Numbers inside brackets each indicate an isoelectric point in a denatured state with 8M urea.

1-6) Preparation of Purified Antigenic Proteins MF-1, MF-2, MF-3, MF-4, and MF-13 in Large Amounts A solution of the above-described *Malassezia* partially purified crude antigen 2782 in a 0.05 M Tris-HCl buffer (pH 8.0) was adsorbed to a column of DEAE-cellulose, previously equilibrated with the same buffer. The column was washed with the same buffer followed by step-by-step elution with the same buffer containing 0.1 M, 0.2 M, and 0.5 M sodium chloride. The fraction eluted with the buffer containing 0.1 M sodium chloride was concentrated using an ultrafiltration membrane (MW 10,000), and the concentrate was then subjected to column chromatography using a column of Sephacryl S-200HR (1.5×90 cm). The eluted fractions having apparent molecular weights of 30,000 to 50,000 were collected and concentrated using an ultrafiltration membrane (MW 10,000), and the concentrates were then subjected to chromatography using the Sephadex G-75 Superfine column (1.5×100 cm) to give Fraction 2 eluted at a molecular weight of about 40,000. This F2 fraction was dialyzed against a 0.05 M Tris-HCl buffer (pH 8.0) containing 0.5 M sodium chloride, and the dialyzed fraction was then subjected to chromatography using the Chelating Sepharose Fast column (1×15 cm), previously chelated with zinc ions and equilibrated with the same buffer. The column was washed with the same buffer followed by elution at buffers pH decreasing levels of 7.0, 6.0, 5.0, and 4.0. The fraction eluted with the pH 5.0 buffer was collected and concentrated, and the concentrate was then further purified by chromatography using the Sephadex G-75 Superfine column (1.5×100 cm), to thereby isolate MF-2.

The effluent fraction in the zinc chelate chromatography was subsequently purified by copper chelate chromatography. Specifically, the effluent fraction was subjected to chromatography using the Chelating Sepharose Fast column (1×15 cm), previously chelated with copper ions and equilibrated with a 0.05 M Tris-HCl buffer (pH 8.0) containing 0.5 M sodium chloride. The column was washed with the same buffer, followed by elution at buffers of decreasing pH levels of 7.0, 6.0, 5.0, and 4.0. The fraction eluted at pH 4.0 was concentrated using an ultrafiltration membrane (MW 10,000), and the concentrate was then further purified by chromatography using the above-mentioned Sephadex G-75 Superfine column, to give MF-1 fraction eluted at a molecular weight of about 40,000. The resulting effluent fraction was concentrated using an ultrafiltration membrane (MW 10,000), and the concentrate was then purified by chromatography using the above-mentioned Sephadex G-75 Superfine column, to give a fraction eluted at a molecular weight of about 40,000. Thereafter, the eluted fraction was purified by anion exchange column chromatography of Mono Q, to isolate MF-3 and MF-4.

A portion of the above-described *Malassezia* partially purified antigen 2782 fraction non-adsorbed to a DEAE-cellulose column was applied to a column of HiLoad 16/60 Superdex 75 pg (manufactured by Pharmacia), previously equilibrated with 0.05 M $NH_4HCO_3$, to collect a fraction having a molecular weight of not more than 20,000. The resulting fraction was adsorbed to HiTrap SP, previously equilibrated with a 0.05 M acetate buffer (pH 5), and elution was carried out with the same buffer supplemented with 0.2 M NaCl. The eluted fraction was applied to a column of HiLoad 16/60 Superdex 75 pg, previously equilibrated with 0.05 M $NH_4HCO_3$, to isolate MF-13.

Finally, using about 0.5 g each of the *Malassezia* partially purified crude antigen 2782 as a starting material, MF-1, MF-2, MF-3, MF-4, and MF-13 were obtained in amounts of 10 mg, 2 mg, 3 mg, 2 mg, and 2 mg, respectively. These antigenic proteins thus prepared in such large amounts gave similar results as those described under Item 1-4) above and Example 10, in terms of SDS electrophoresis, isoelectric electrophoresis, and N-terminal amino acid sequencing analysis.

EXAMPLE 2

Preparation of Monoclonal Antibodies 2-1) Mouse Immunization, Cell Fusion, and Hybridoma Cloning Ten micrograms of each of the purified antigenic proteins MF-1, MF-2, and MF-3 as obtained in Example 1 was suspended in a Freund's complete adjuvant, and each suspension was intraperitoneally administered to male BALB/c mice at 5 weeks of age. Four weeks later, 20 μg of an allergen suspended in a Freund's complete adjuvant was intraperitoneally administered for booster. Additional four weeks later, 20 μg of the same allergen dissolved in a physiological saline was intravenously administered.

Three days after final immunization, cell fusion was carried out by taking out splenocytes and mixing with myeloma cells (P3X63-Ag8.653) in a 4:1 ratio, and then adding 43% polyethylene glycol 2000 thereto. This mixture was sown into 96-well microplate wells at $2 \times 10^5$ splenocytes/well, and hybridomas were proliferated in an HAT medium selectively. The presence of the desired antibody produced was examined by ELISA using the culture supernatant to select antibody-producing cells. As a result, the 5B4 strain (FERM BP-5608) was obtained as a clone of a hybridoma that produces the M-40 monoclonal antibody against the purified antigenic protein MF-1; the 8G11 strain (FERM BP-5609) was obtained as a clone of a hybridoma that produces the M-3 monoclonal antibody against the purified antigenic protein MF-2; and the 10C1 strain (FERM BP-5610) was obtained as a clone of a hybridoma that produces the M-1 monoclonal antibody against the purified antigenic protein MF-3.

2-2) Preparation of Ascites and Purification of Monoclonal Antibodies

To pristane-pretreated nude mice, $10^7$ hybridomas were intraperitoneally injected to allow hybridoma proliferation, and after one to two weeks, ascites was collected. From the resulting ascites, the monoclonal antibodies were purified using a protein A column kit (manufactured by Amersham), to give the M-40 monoclonal antibody against MF-1, the M-3 monoclonal antibody against MF-2, and the M-1 monoclonal antibody against MF-3. These monoclonal antibodies were all of the IgG1 isotype.

2-3) Preparation of Monoclonal Antibody-Immobilized Column and Purification of Antigenic Protein MF-3 Using Above Column Fifteen milligrams of the above M-1 monoclonal antibody was dialyzed against a coupling buffer (0.1 M $NaHCO_3$, 0.5 M NaCl, pH 8.3), and the dialyzed monoclonal antibody was then coupled to 1 g of Sepharose 4B (manufactured by Pharmacia) activated with cyanogen bromide by a conventional method to prepare an antibody-immobilized resin.

The resin obtained was transferred into a lesser column of 5 ml capacity. A solution of 40 mg of the *Malassezia* partially purified crude antigen 2782 in a 0.05 M Tris-HCl buffer (pH 8.0) was applied to the column. After the column was thoroughly washed with a 0.1 M Tris-HCl buffer (pH 8.0), elution of the antibody-bound antigenic protein was carried out with a 0.1 M glycine-HCl buffer (pH 2.5). The eluate was immediately made neutral again by the addition of a 1 M Tris-HCl buffer (pH 8.0), and the neutralized eluate was then concentrated using an ultrafiltration membrane (MW 10,000), followed by gel filtration chromatography using the Sephadex G-75 Superfine column (1.5×100 cm) in the same manner as above, to isolate about 300 μg of MF-3 of high purity.

EXAMPLE 3

Diagnostic Application of Purified Antigenic Proteins 3-1) Determination of Specific IgE Antibodies by RAST Method Paper disc activation with cyanogen bromide and coupling of purified allergens to the paper disc were carried out according to the method of Miyamoto et al. (*Allergy*, 22, 584-594, 1973). One paper disc coupled with the allergen and 50 µl of sera from patients were added to a polystyrene tube, followed by incubation at room temperature for 3 hours. The paper disc was washed three times with a physiological saline containing 0.2% Tween 20, and 50 µl of the $^{125}$I-labeled anti-human IgE antibody of the RAST-RIA kit, manufactured by Pharmacia, was then added, followed by overnight incubation at room temperature. The disc was washed three times again, and radioactivity was then determined using a gamma counter. From a standard curve prepared from a simultaneous radioactivity determination with a reference reagent of the kit, the IgE antibody titer was calculated. For samples that yielded values exceeding the upper limit of the standard curve (>17.5 PRU/ml), the antibody titer was calculated after the samples were diluted 10 folds or 100 folds in equine sera and assayed again.

3-2) Diagnosis Using Purified, Antigenic Proteins MF-1, MF-2, MF-4, and MF-13

A skin test using a *Malassezia* crude antigen was carried out on patients with atopic dermatitis (hereinafter abbreviated AD) or bronchial asthma (hereinafter abbreviated BA) or both (AD+BA). Positive response was observed in 43 out of 57 AD patients (75%), 108 out of 919 of BA patients (12%), and 47 out of 102 AD+BA patients, demonstrating an extremely high positivity rate in the AD patients. Also, 100%, 59%, and 85%, respectively among these AD, BA, and AD+BA patients with positive skin tests, were positive in IgE antibody determination by RAST method.

On the 76 patients (AD patients: 30, BA patients: 20, AD+BA patients: 26) positive both in the skin test using the *Malassezia* crude antigen and in RAST method (1 or higher score), IgE antibody titers against three purified antigenic proteins, i.e., MF-1, MF-2, and MF-4, were determined by RAST method (RIA method). IgE antibody titers for antigenic proteins were determined on 12 normal individuals with negative skin tests as well in the same manner as above. As a result, it was made clear from Table 2 that IgE antibodies against the antigenic proteins were present in sera from patients at very high rates. Especially high positivity rates were obtained against MF-1 and MF-2. Further, there were patients with surprisingly very high IgE antibody titers (Table 3), and particularly the mean titer against MF-1 and MF-2 for the AD patients was 100 PRU, and there were some patients with highest values exceeding 1,000 PRU. Also, the sera from all patients positive to the *Malassezia* crude antigen in RAST method contained the IgE antibody against any one of the purified antigenic proteins MF-1, MF-2, and MF-4.

Also the IgE antibody titer against MF-13 by RAST method for 11 AD patients positive both in the skin test using the *Malassezia* crude antigen and in RAST method. As a result, nine out of 11 patients were found to be positive in RAST.

TABLE 2

Patients with Allergoses (Rate of RAST Positive)

|      | BA (n = 20) | AD + BA (n = 26) | AD (n = 30) | Total (n = 76) | normal individuals (n = 12) |
|------|-------------|------------------|-------------|----------------|-----------------------------|
| MF-1 | 100 (20/20) | 96 (25/26)       | 90 (27/30)  | 95 (72/76)     | 0 (0/12)                    |
| MF-2 | 100 (20/20) | 100 (26/26)      | 87 (26/30)  | 95 (72/76)     | 0 (0/12)                    |
| MF-4 | 75 (15/20)  | 88 (23/26)       | 87 (26/30)  | 84 (64/76)     | 0 (0/12)                    |

BA: Patients with allergic asthmatics.
AD: Patients with atopic dermatitis.
AD + BA: Patients with Atopic dermatitis and allergic asthmatics complications.

TABLE 3

Patients with Allergoses [IgE Antibody Titer (PRU Value)]

|      | BA (n = 20)     | AD + BA (n = 26) | AD (n = 30)       | normal Individuals (n = 12) |
|------|-----------------|------------------|-------------------|-----------------------------|
| MF-1 | 1.65 ± 0.66     | 14.73 ± 4.15     | 119.73 ± 56.95    | <0.35                       |
| MF-2 | 4.32 ± 2.59     | 16.01 ± 4.45     | 112.84 ± 52.23    | <0.35                       |
| MF-4 | 3.54 ± 2.08     | 9.75 ± 2.43      | 94.75 ± 42.43     | <0.35                       |

BA: Patients with allergic asthmatics.
AD: Patients with atopic dermatitis.
AD + BA: Patients with Atopic dermatitis and allergic asthmatics complications.

3-3) Immunological Properties of Purified Antigenic Proteins MF-1, MF-2, MF-3, and MF-4

A RAST cross inhibition test using pooled sera from patients was carried out to evaluate cross reactivity among three purified antigenic proteins (MF-1, MF-2, MF-4) (Table 4). As a result, it was shown that they did not mutually cause cross-reactivity, namely that the specific IgE antibodies against the respective purified antigenic proteins are present in the sera from patients.

TABLE 4

| Antigen Immobilized on Solid Phase | Concentration of Various Antigens Required for 50% Inhibition of Binding Antigen Immobilized on Solid Phase and Patient IgE (µg/ml) | | |
|------------------------------------|-------------|-------------|-------------|
|                                    | MF-1        | MF-2        | MF-4        |
| MF-1                               | 0.038 (1)   | 8.6 (230)   | 52 (1370)   |
| MF-2                               | >100 (>7700)| 0.013 (1)   | >100 (>7700)|
| MF-4                               | 18 (290)    | 30 (480)    | 0.062 (1)   |

Figure 12:
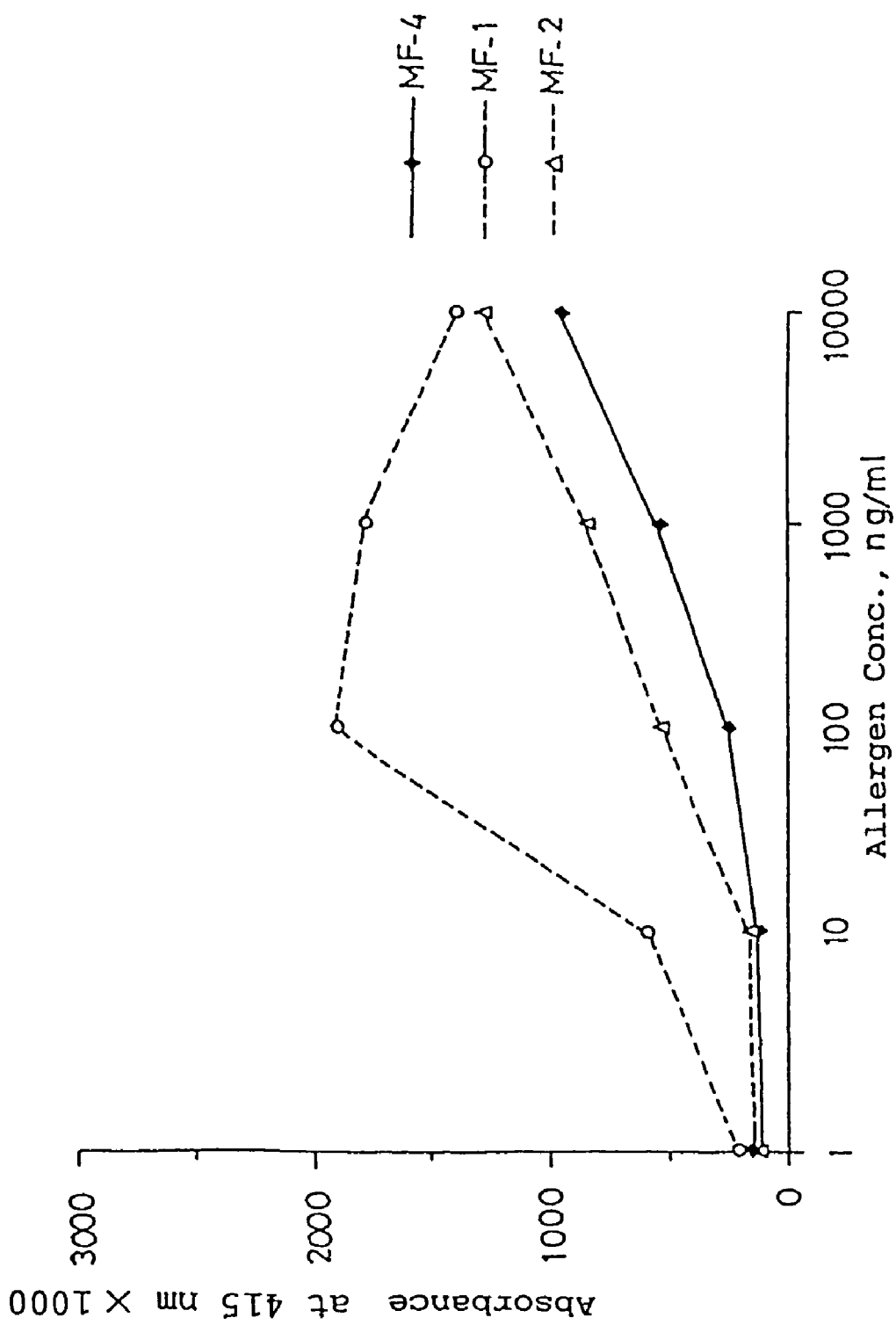
FIG. 12 is a graph showing the concentration dependency of the IgE binding ability of antigenic proteins MF-1, MF-2, and MF-4.

Next, the purified antigenic proteins MF-1, MF-2, and MF-4 were stepwise diluted and their antigen potencies were determined by the Direct RAST EIA method. Specifically, dilutions of the purified, antigenic protein MF-1, MF-2, and MF-4 were each coupled to a cyanogen bromide-activated paper disc and then the coupled purified, antigenic protein was blocked with ethanolamine. Thereafter, 50 µl of a 5-fold dilution of pooled sera was then added to each disc, and the mixture was reacted with a diluted β-galactosidase-labeled goat anti-human IgE antiserum. Thereafter, an enzyme substrate was added, followed by absorption determination at 415 nm. The results are shown in FIG. 12. It is clear that MF-1 binds to sera from patients IgE at the lowest concentration.

Figure 13:
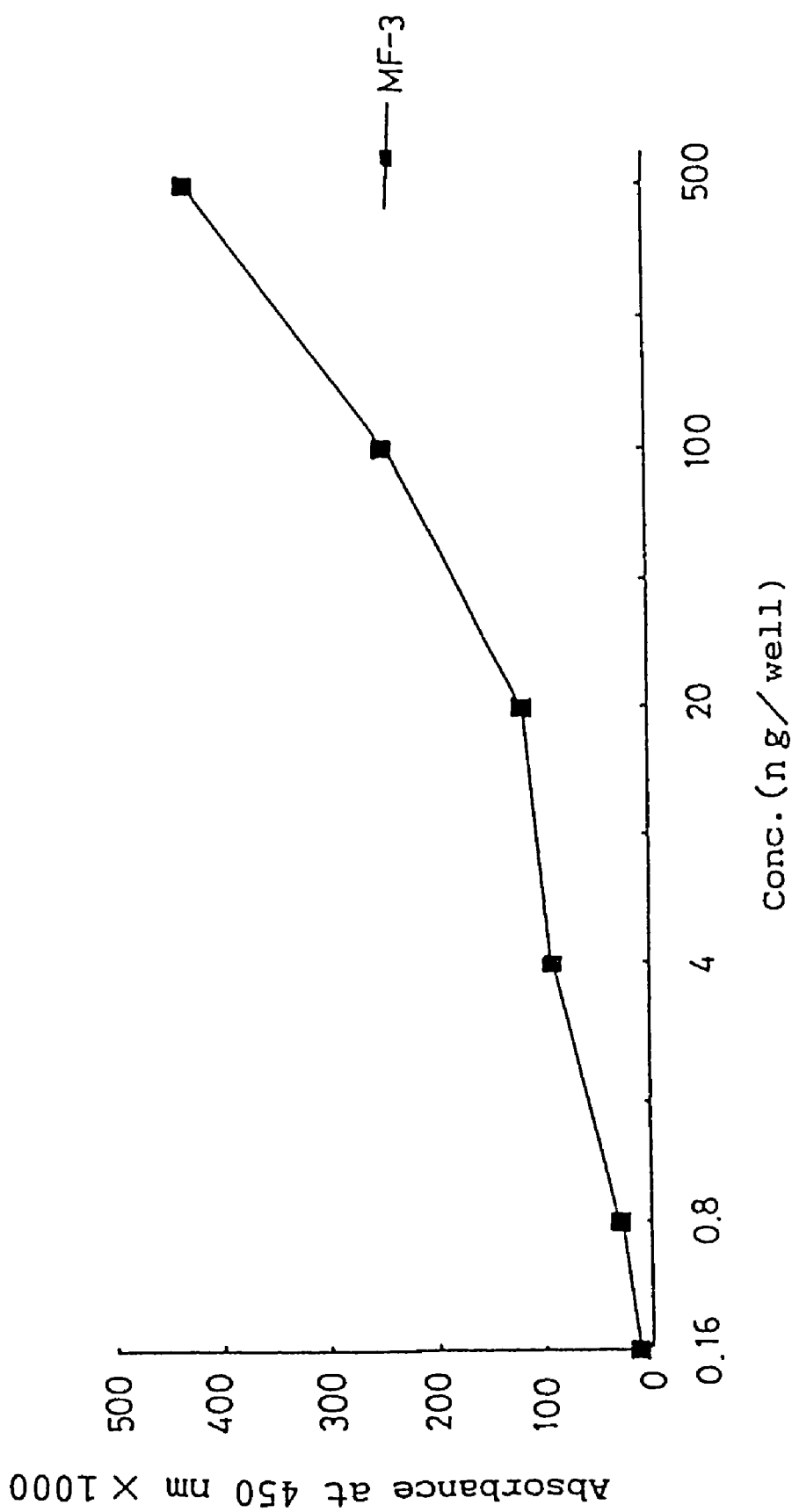
FIG. 13 is a graph showing the concentration dependency of the IgE binding ability of MF-3.

Separately, the purified antigenic protein MF-3 was stepwise diluted, and its antigen potency was determined by ELISA. Specifically, after applying each dilution of the purified antigenic protein MF-3 to a microplate, the microplate was washed with a physiological saline containing 0.01% Tween 20, blocked with PBS containing 3% BSA, washed with a physiological saline containing 0.01% Tween 20, and then pooled sera were added. The microplate was kept standing at 37° C. for 2 hours, and a secondary antibody, a peroxidase-labeled goat anti-human IgE antiserum was added, and subsequently a substrate solution was added; after color development, absorbance at 450 nm was determined. The results are shown in FIG. 13.

EXAMPLE 4

Preparation of Pyridylethylated Derivative of Cysteine Residue of Purified, Antigenic Protein MF-2

Figure 14:
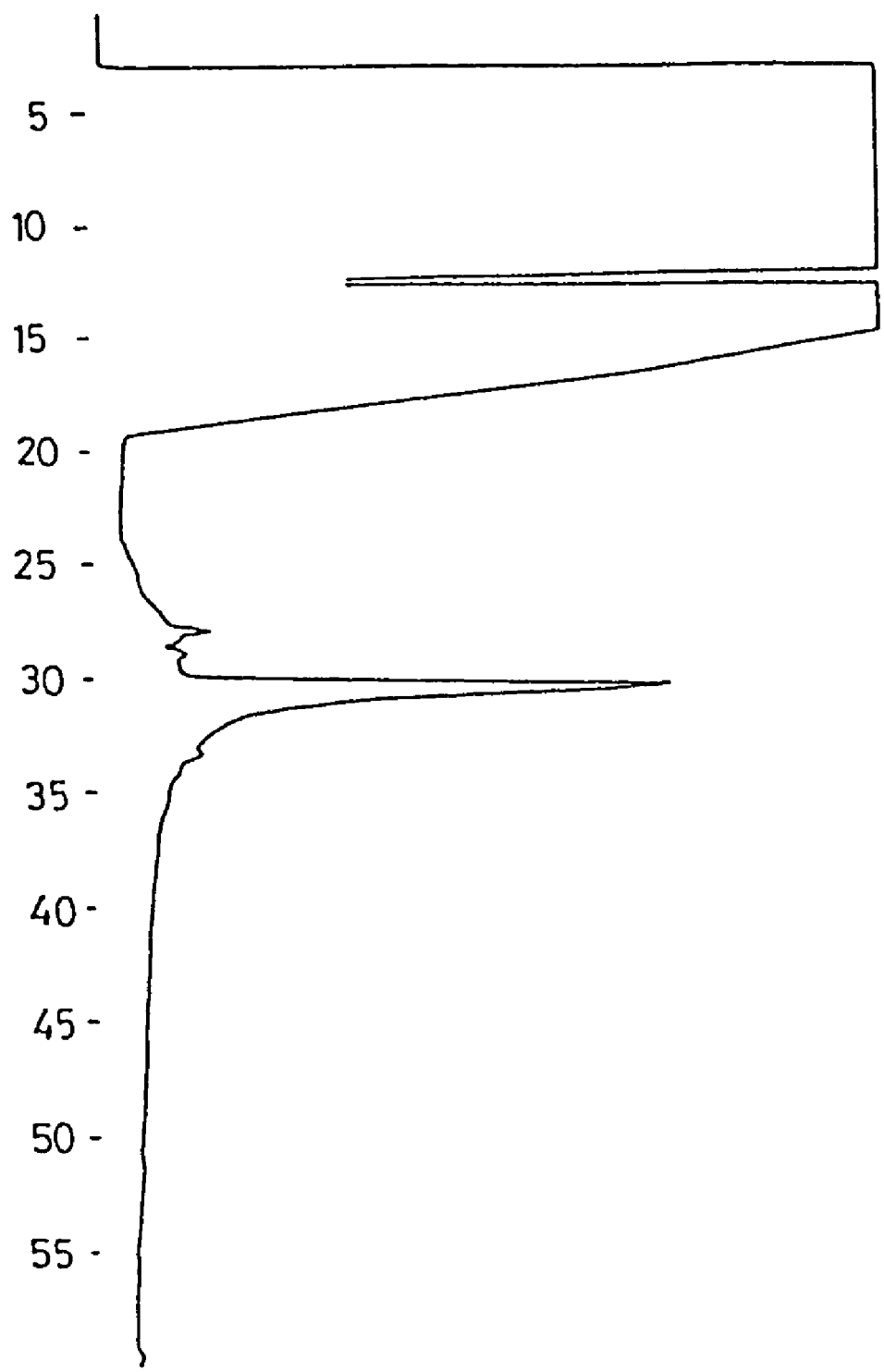
FIG. 14 is a chart showing purification of a pyridylethylated product of MF-3 by HPLC.
Figure 15:
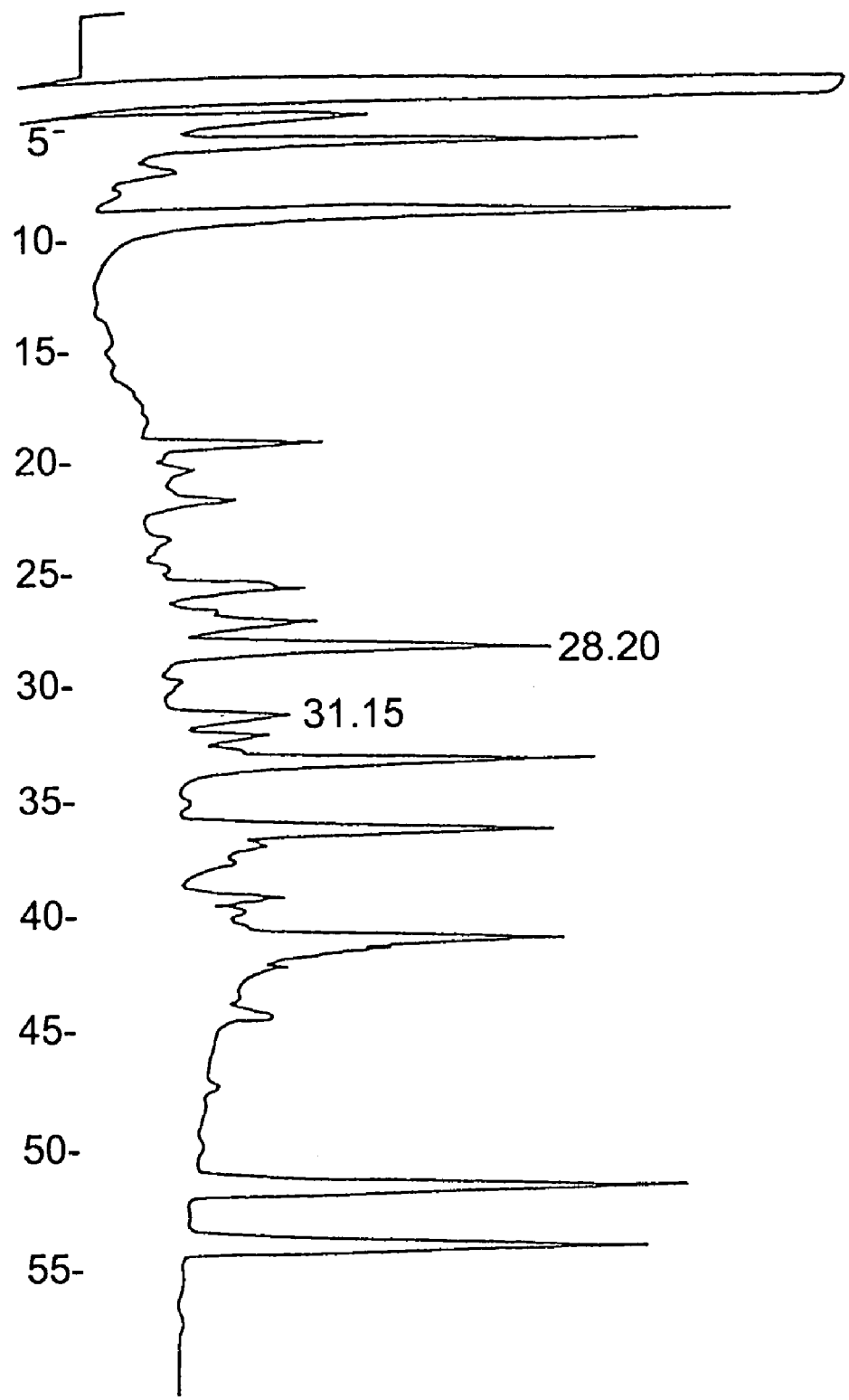
FIG. 15 is an HPLC analytic chart of digested products of lysylendopeptidase of MF-2 (pyridylethylated product).

The purified antigenic protein MF-2 (0.04 mg) was dissolved in 200 µl of a borate-buffered saline (pH 8.0). To this solution were added 800 µl of 5 M guanidine hydrochloride, 1 µl of 4-vinylpyridine, and 2 µl of tributyl phosphine. After replacing the atmosphere with nitrogen gas, reaction was carried out overnight at 37° C., and the resulting mixture was subjected to isolation and purification by HPLC (column: µ-Bondasphere C4-300, 2×150 mm, manufactured by Waters; solvents: washing with 0.05% TFA/water for 15 minutes, followed by linear gradient elution so as to give 80% acetonitrile containing 0.05% TFA after 60 minutes; flow rate: 220 µl/min.; detection: 220 nm; column temp.: 40° C.; FIG. 14). The product obtained was identified as the pyridylethylated product of MF-2, from the fact that its band appeared in the neighborhood of 20 kDa in SDS electrophoresis under non-reduced conditions (in absence of mercaptoethanol), and that the peptide fragments (FIG. 15) which have the N-terminal amino acid sequences as shown by SEQ ID NOs:47 and 48 (eluted at 28.20 and 31.15, respectively), obtained by lysylendopeptidase digestion of the product obtained had a pyridylethylcysteine group. The pyridylethylated MF-2 obtained, which was similar to MF-2, was confirmed to be bound to sera IgE of patients from *Malassezia* allergoses by immunoblotting after SDS electrophoresis.

EXAMPLE 5

Isolation of Antigenic Fragment Peptide Derived from Purified Antigenic Protein MF-3

Figure 16:
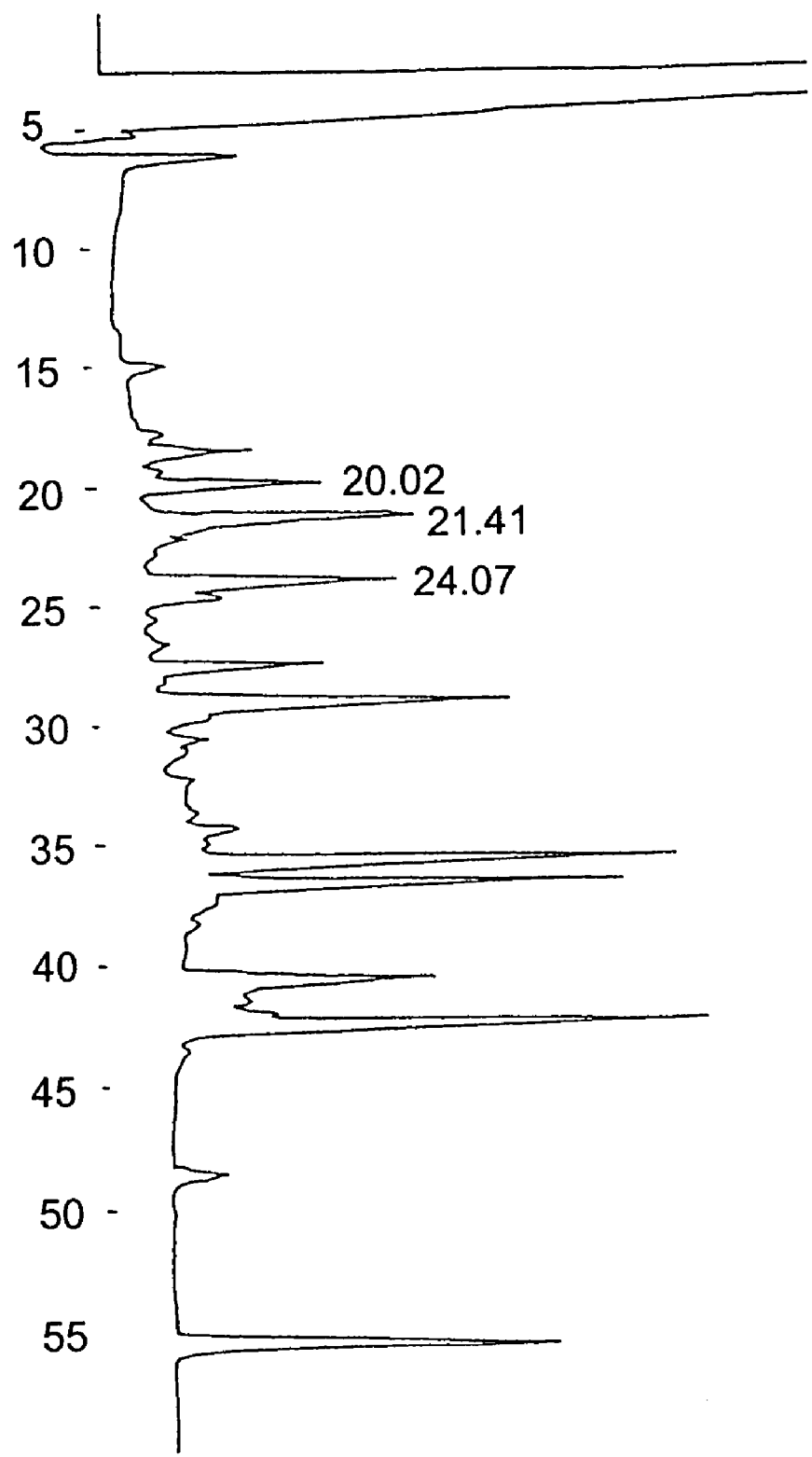
FIG. 16 is an HPLC analytic chart of digested products of lysylendopeptidase of MF-3 (pyridylethylated product).

The purified antigenic protein MF-3 (0.04 mg) was dissolved in 100 µl of a borate-buffered saline (pH 8.0). To this solution were added 900 µl of 5 M guanidine hydrochloride, 1 µl of 4-vinylpyridine, and 2 µl of tributyl phosphine. After replacing the atmosphere with nitrogen gas, reaction was carried out overnight at 37° C., and the resulting mixture was subjected to isolation and purification by HPLC (column: µ-Bondasphere C4-300, 2×150 mm, manufactured by Waters; solvents: washing with 0.05% TFA/water for 15 minutes, followed by linear gradient elution so as to give 80% acetonitrile containing 0.05% TFA after 60 minutes). To the resulting purified, antigenic protein MF-3 treated with guanidine hydrochloride were added, 100 µl of 50 mM N-ethyl-morphine-acetic acid (pH 9.0) and lysylendopeptidase (Achromobacter protease I, manufactured by Wako Pure Chemical Industries), followed by reaction carried out overnight at 37° C. Thereafter, the reaction mixture was subjected to HPLC (column: µ-Bondasphere C18-300, 2×150 mm, manufactured by Waters; solvents: linear gradient elution from 0.05% TFA/water eluted so as to give 60% acetonitrile containing 0.05% TFA; flow rate: 200 µl/min.; detection: 214 nm; column temp.: 40° C.; FIG. 16). Each peptide fragment was separately collected and freeze-dried, and thereafter the freeze-dried fragment was assayed for binding to sera IgE of patients from *Malassezia* allergoses by ELISA as described below.

Specifically, each peptide fragment (about 10 to 100 pmol for each) was spread onto a microplate using a peptide coating kit (manufactured by Takara Shuzo Co., Ltd.) and then washed with a physiological saline containing 0.01% Tween 20. The washed microplate was blocked with 3% BSA, and treated with the sera from patients. Thereafter, each peptide fragment was then reacted with a diluted peroxidase-labeled goat anti-human IgE antibody, and an enzyme substrate was added thereto. After a given period of time, absorbance was determined to detect antigenic fragments. As a result, there appeared to show the antigenic fragments that were bound to patient serum IgE were present in peaks eluted around 20.02, 21.41, and 24.07 minutes. Of these peaks, the 21.41-minute peak was found to contain a peptide having an amino acid sequence consisting of HHQTYVNNLNAAXK (SEQ ID NO:58, wherein X is an undetermined amino acid).

EXAMPLE 6

Lymphocyte Blast Formation Test

Heparinized venous blood samples were collected from subjects [eight patients with allergoses (Nos. 1 through 8 in Table 5), two normal individuals (Nos. 9 and 10 in Table 5)], and lymphocytes were separated by the Ficoll gravitational centrifugation method. After preparation with a 10% FCS-supplemented RPMI1640 medium so as to give a cell number of $5 \times 10^5$ cells/ml, this suspension was poured onto 96-well microplates at 0.2 ml per plate. The above *Malassezia* partially purified crude antigen 2782 was added so as to have concentrations of 10 and 100 µg/ml, and the purified, antigenic proteins (MF-1, MF-2, and MF-4) were each added so as to have concentrations of 1 and 10 µg/ml, followed by five days of cultivation in the presence of 5% $CO_2$ at 37° C. under high-humidity conditions. In the forth day, 0.5 µCi tritiated ($^3$H)-thymidine was added. After completion of the cultivation, lymphocytes were harvested and assayed for the amount of $^3$H-thymidine uptake using a liquid scintillation counter. Using the mean value for three runs, the ratio of the amount of the $^3$H-thymidine uptake of the antigen-added and non-added groups was expressed as the SI (stimulation index). The results are shown in Table 5. It is clear from Table 5 that the lymphocytes derived from Patient No. 4 proliferated in response to the purified, antigenic proteins MF-1 and MF-2, and that those derived from Patient Nos. 1 and 6 proliferated especially in response to MF-2.

TABLE 5

| | SI (in case of adding low allergen concentration/in case of adding high allergen concentration)*) | | | | | | | | | |
|---|---|---|---|---|---|---|---|---|---|---|
| | 1 | 2 | 3 | 4 | 5 | 6 | 7 | 8 | 9 | 10 |
| MF-1 | 7.7/2.5 | 4.3/1.4 | 1.0/0.9 | 4.2/3.7 | 2.6/2.0 | 2.1/1.0 | 1.7/1.2 | 2.1/1.7 | 1.1/0.5 | 2.0/0.7 |
| MF-2 | 4.0/2.9 | 1.3/1.5 | 1.9/1.2 | 7.8/4.2 | 2.3/2.3 | 3.1/2.6 | 2.0/1.8 | 1.4/1.7 | 2.0/0.7 | 1.6/1.0 |
| MF-4 | 1.8/1.3 | 1.2/1.1 | 1.0/0.9 | 2.5/1.4 | 1.2/1.8 | 1.9/1.7 | 1.1/0.9 | 1.3/1.3 | 1.9/0.8 | 0.9/0.6 |

Remarks *):
"In case of adding low allergen concentration" refers to a case of adding 1 μg/ml MF-1, MF-2, or MF-4.
"In case of adding high allergen concentration" refers to a case of adding 10 μg/ml MF-1, MF-2, or MF-4.
1-8: Allergic patients.
9-10: Normal individuals.

EXAMPLE 7

Preparation of Diagnostic Reagent for Intracutaneous Reaction and Preparation of Titration Reagent for Diagnosis Against *Malassezia* Allergy A purified allergen-active component is dried and collected in a powder form to be used as a diagnostic reagent for intracutaneous reaction against *Malassezia* allergoses and as a titration reagent for the diagnosis of the *Malassezia* allergy. The diagnostic reagent for intracutaneous reaction is prepared by 200,000-fold dilution of the allergen-active component using a 0.9% physiological saline containing 0.5% phenol as a solvent. The titration reagent for the diagnosis of the *Malassezia* allergy is prepared by dissolving the allergen-active component in a Hanks' buffer at a concentration of 1 mg/ml, to give a stock solution for a titration reagent for histamine release, using the dilutions of the stock solution.

EXAMPLE 8

Preparation of Antigenic Agent for Hyposensitization Therapy

A purified allergen-active component is dried and collected in a powder form to be used as a hyposensitization therapeutic agent for *Malassezia* allergoses. The allergen-active component is dissolved in a 0.9% saline containing 0.5% phenol at a concentration of 1 mg/ml to give a stock solution of an antigen for hyposensitization therapy.

EXAMPLE 9

Quantitative Assay of Purified, Antigenic Protein MF-1 in House Dust and Cultivation of *Malassezia*

House dust was collected from rooms, bedclothes, and the like, in houses inhabited by bronchial asthma patients, using a vacuum cleaner under given conditions. MF-1 was subjected to quantitative assay by means of sandwich ELISA using a rabbit polyclonal antibody and the mouse monoclonal antibody (M-40) as obtained in Example 2-2), and a supernatant obtained from 1:10 (w/v) extraction of the dust was used as a sample for quantitative assay of MF-1. In order to cultivate *Malassezia*, the dust was suspended in sterile water in a 1:10 (w/v) ratio and sown over a plate medium. Also, a sterile tape was once attached to the bedclothes surface, removed, and placed on the plate medium. The media used were PDA, M40YA, or a Dixon agar medium, and the number of colonies was counted after cultivation at 25° C. for one week.

It is possible to subject MF-1 to quantitative assay of the level of not less than 1 ng/g dust by sandwich ELISA method, by which 87.1 to 1.1 ng/g dust of MF-1 was detected in 16 out of 24 dust samples derived from bedclothes. As for the cultivation results for *Malassezia* on the bedclothes surface, obtained by the tape method, 10 out of the 24 samples were positive. Incidentally, out of the 24 samples, 14 samples (58%, eight being positive, six being negative) gave results in agreement with those of MF-1 detection by sandwich ELISA method and cultivation.

EXAMPLE 10

Determination of Partial Amino Acid Sequences of Purified, Antigenic Proteins MF-1, MF-2, MF-3, MF-4, MF-5, MF-6, MF-7, MF-10, and MF-13

N-terminal amino acid sequence analysis was carried out by a conventional method. As a result, it was made clear that MF-1 has the amino acid sequence:

```
                                          (SEQ ID NO:45)
Pro Gly Asp Pro Thr Ala Thr Ala Lys Gly Asn Glu
Ile Pro Asp Thr Leu Met Gly Tyr Ile Pro Trp Thr
Pro Glu Leu Asp
```

As for MF-2, since its N-terminal is blocked, pyridylethylation was followed by lysylendopeptidase digestion. The resulting peptide fragments were analyzed by C18 reversed-phase HPLC. The various peaks obtained were separately collected, some of which were subjected to amino acid sequencing determination. The three peptide fragments eluted at 27.07 minutes, 28.20 minutes, and 31.15 minutes, respectively, were determined to have the following respective N-terminal amino acid sequences:

```
                                          (SEQ ID NO:46)
Val Glu Tyr Phe Gly Ile Asp Glu Gly Glu Pro Lys;

(SEQ ID NO:47)
Asp Asn Leu Thr Phe Ala Gln Asp Val Asn Cys Glu
Phe;

(SEQ ID NO:48)
Val Val Ile Val Ala Val Pro Gly Xaa Phe Thr Pro
Thr Cys Thr Ala Asn His Val Pro Xaa Tyr Xaa Glu
``` wherein Xaa is an undetermined amino acid.

As for MF-3, since its N-terminal is also blocked, pyridylethylation was followed by lysylendopeptidase digestion. The resulting peptide fragments were analyzed by C18 reversed-phase HPLC. The various peaks obtained were separately collected, some of which were subjected to amino acid sequencing determination. The three peptide fragments eluted at 35.68 minutes, 36.68 minutes, and 29.15 minutes, respectively, were determined to have the following respective N-terminal amino acid sequences:

```
                                              (SEQ ID NO:49)
Asp Gln Asp Pro Leu Thr Thr His His Pro Val Ile
Gly Trp Asp Xaa Xaa Glu His Ala
``` wherein Xaa is an undetermined amino acid;

```
                                              (SEQ ID NO:50);
Ala Trp Trp Asn Val Val Asn Trp Ala Glu Ala Glu Lys
                                              (SEQ ID NO:51)
Phe Xaa Gly Gly Gly His Ile Asn Xaa Ser Leu Phe
``` wherein Xaa is an undetermined amino acid.

In addition, as a result of N-terminal amino acid sequence analysis, it was made clear that MF-4 had the amino acid sequence:

```
                                              (SEQ ID NO:52)
Lys Tyr Thr Leu Pro Pro Leu Pro Tyr Asp Tyr Gly
Ala Leu Glu Pro Ala Ile Ser Gly Glu Ile Met Glu
Thr His Tyr Glu Lys His
```

In addition, as a result of N-terminal amino acid sequence analysis, it was made clear that MF-5 had the amino acid sequence:

```
                                              (SEQ ID NO:53)
Xaa Xaa Xaa Xaa Xaa Glu Pro Tyr Asp Val Ile Val
Ile Gly Gly Gly Pro Gly Gly Tyr Val Ala Xaa Xaa
Lys Xaa Xaa Gln
``` wherein Xaa is an undetermined amino acid.

In addition, as a result of N-terminal amino acid sequence analysis, it was made clear that MF-6 had the amino acid sequence:

```
                                              (SEQ ID NO:54)
Arg Lys Val Ala Val Leu Gly Ala Ser Gly Gly Ile
Gly Gln Pro Leu Ser Leu Leu Met Lys Leu Asn Pro
Lys Val Thr Glu Leu Arg
```

In addition, as a result of N-terminal amino acid sequence analysis, it was made clear that MF-7 had the amino acid sequence:

```
                                              (SEQ ID NO:55)
Gly Asn Asn Gly Leu Ser Glu Val Val Tyr Lys Pro
Asp Xaa Gln Xaa Thr Xaa Glu Phe Xaa Val Ile
``` wherein Xaa is an undetermined amino acid.

In addition, as a result of N-terminal amino acid sequence analysis, it was made clear that MF-10 had the amino acid sequence:

```
Val Asp Gln Xaa Tyr Phe Gly Leu Xaa  (SEQ ID NO:56)
``` wherein Xaa is an undetermined amino acid.

In addition, as a result of N-terminal amino acid sequence analysis, it was made clear that MF-13 had the amino acid sequence:

```
                                              (SEQ ID NO:57)
Ser Asn Val Phe Phe Asp Ile Thr Lys Asn Gly Ser
Pro Leu Gly Thr Ile Lys Phe Lys Leu Phe Asp Asp
Val
```

The other antigenic proteins could not be analyzed due to N-terminal blocking, and the like.

As a result of homology searching with known proteins, it was made clear that MF-2 is a protein having the partial amino acid sequence of SEQ ID NO:48 homologous to a peroxisome membrane protein (PMP-20) derived from *Candida boidinii*, and MF-3 is a protein having the above partial amino acid sequence homologous to iron/manganese-superoxide dismutase. In addition, it was made clear that MF-4 is a protein having the above N-terminal amino acid sequence homologous to iron/manganese-superoxide dismutase in the same manner as in MF-3. In addition, it was made clear that MF-5 is a protein having the above N-terminal amino acid sequence homologous to dehydeolipoamide dehydrogenase. In addition, it was made clear that MF-6 is a protein having the above N-terminal amino acid sequence homologous to malate dehydrogenase. In addition, as for MF-7 and MF-10, no homology to known proteins was found from their N-terminal amino acid sequences. In addition, it was made clear that MF-13 is a protein having the above N-terminal amino acid sequence homologous to cyclophilin.

EXAMPLE 11

Cloning of Antigenic Protein MF-1 Gene from *M. furfur*

11-a) Purification of Total RNA from *M. furfur*

In order to obtain total RNA from cells of the *M. furfur* TIMM2782 strain, the strain was cultured for 72 hours in 300 ml of a YNB medium (0.67% bacto yeast nitrogen DNA, 0.5% Bacto Casiton, 0.1% Tween 60, 2.0% glucose, 5% MEM-vitamin solution), and the cells were then harvested by centrifugation at 3,000 rpm for 15 minutes. The harvested cells were rapidly frozen with liquid nitrogen. The frozen cells were disrupted into a powder form by a mortar, and 1.3 mg of the total RNA was then recovered and purified by an RNA extraction kit (manufactured by Pharmacia).

11-b) Amplification of MF-1 Gene by RT-PCR

The oligonucleotides MF1F1 and MF1F2, deduced from the amino acid sequence for the N-terminal of the MF-1 protein described in Example 10 were synthesized and purified to be used as primers for PCR. The base sequences for MF1F1 and MF1F2 are shown by SEQ ID NOs:15 and 16, respectively, in Sequence Listing. An MF-1 cDNA was amplified by RT-PCR using RNA PCR Kit Ver. 2 (manufactured by Takara Shuzo Co., Ltd.) with 1 μg of the total RNA purified in Example 11-a). Specifically, the cDNA was synthesized from 1 μg of the total RNA by an AMV reverse transcriptase reaction (at 42° C. for 60 minutes) using an oligo(dT)$_{20}$-M4 adaptor primer. PCR reaction was carried out by repeating 40 cycles of the temperature shifts at 94° C. for 1 minute, at 55° C. for 2 minutes, and at 72° C. for 1.5 minutes, using the MF1F1 primer and the M13M4 primer included in the kit together with this cDNA as a template. Second PCR reaction (nested PCR reaction) was carried out using this PCR reaction mixture as a template. The MF1F2 primer and the M13M4 primer were used in this reaction. As a result of the PCR, a cDNA fragment with about 570 bp in length was amplified. This cDNA was cloned into a pUC118 vector (manufactured by Takara Shuzo Co., Ltd.), and its base sequence was then determined. The resulting base sequence is shown by SEQ ID NO:17 in Sequence Listing. The amino acid sequence deduced from SEQ ID NO:17 was identical to the amino acid sequence determined from the MF-1 protein. Therefore, it is clearly demonstrated that this cDNA fragment is an MF-1 gene.

11-c) Preparation of *M. furfur* cDNA Library

20 μg of poly(A)$^+$ RNA was purified from 1 mg of the total RNA obtained in Example 11-a) with Oligotex-dT30<SUPER> (manufactured by Takara Shuzo Co., Ltd.). A cDNA was synthesized by a cDNA synthesis kit (manufactured by Takara Shuzo Co., Ltd.) using 5 μg of the poly(A)$^+$ RNA. A cDNA library was constructed by ligating the synthesized cDNA and the lambda phage vector λSH1ox™ (manufactured by Novagen) together, and carrying out in vitro packaging using Phagemaker System and Phage Pack Extract (manufactured by Novagen).

11-d) Cloning of MF-1 cDNA

The cDNA library obtained in Example 11-c) was infected into a host *Escherichia coli* ER1647 strain and mixed with Top Agarose (an LB medium containing 0.7% bacto agar), and a plaque was then formed by overlaying on an LB plate and culturing at 37° C. overnight. The resulting plaque was transferred onto a nylon membrane ("Hybond-N," manufactured by Amersham) and subjected to plaque hybridization. A cDNA fragment of MF-1 with about 570 bp obtained in Example 11-b) was labeled with [α-$^{32}$P]dCTP using a random primer DNA labeling kit (manufactured by Takara Shuzo Co., Ltd.), and the labeled cDNA fragment was used as a probe for hybridization. 1.6×10$^5$ plaques were screened for, and 10 clones with strong signals out of the positive clones were then subjected to further analysis. Specifically, *E. coli* cells harbouring the plasmid which has a region containing the MF-1 cDNA were obtained from these phages by automatic subcloning in *E. coli*. The plasmids were purified from these *E. Coli* cells, and pMF1-7, which contained the longest fragment with about 600 bp cDNA, was selected. The cDNA was subcloned into a pUC118 vector (manufactured by Takara Shuzo Co., Ltd.), and its base sequence was then determined. The base sequence thereof is shown by SEQ ID NO:1 in Sequence Listing, and the MF-1 gene encodes a polypeptide having an amino acid sequence as shown by SEQ ID NO:8 in Sequence Listing.

11-e) Purification of Genomic DNA from *M. furfur*

In order to obtain a genomic DNA from cells of the *M. furfur* TIMM2782 strain, the strain was cultured for 72 hours in 200 ml of the YNB medium, and the cells were harvested by centrifugation at 3,000 rpm for 15 minutes. The harvested cells were washed with a washing solution (0.9% NaCl, 0.05% Tween 80) five times, and then with a PK buffer (0.15 M NaCl, 0.1 M Tris-HCl (pH 7.5), 10 mM EDTA) three times. The cells were suspended in 8 ml of the PK buffer, and an equivolume of glass beads (425 to 600 μm in diameter, manufactured by Sigma) was then added thereto, and the cells were disrupted using mini-bead beater (manufactured by Biospace). Protease K and SDS were added to the cell disruption, so as to have final concentrations of 0.15 mg/ml and 1% (w/v), respectively, and the resulting mixture was treated at 50° C. for 3 hours while gently stirring the mixture. The nucleic acid was purified by subjecting the disrupted solution to phenol extraction, phenol/chloroform extraction, and chloroform extraction (each carried out once), and subjected to ethanol precipitation. The nucleic acid obtained by centrifugation at 10,000 rpm for 15 minutes was dissolved in a TE buffer (10 mM Tris-HCl, 1 mM EDTA). RNase A was added to the nucleic acid solution so as to have a final concentration of 40 μg/ml, and the mixture was treated at 37° C. for 40 minutes. The DNA was recovered and purified by subjecting the solution to phenol extraction, phenol/chloroform extraction, and chloroform extraction (each carried out once), and by subjecting to ethanol precipitation.

11-f) Cloning of MF-1 Genomic DNA

The genomic DNA obtained in Example 11-e) was completely cleaved with BamHI or PstI, and each of the resulting fragments was then cloned into the pUC118 vector to prepare two kinds of genomic DNA libraries. An MF-1 genomic DNA was screened from the libraries by colony hybridization using the MF-1 cDNA obtained in Example 11-d) as a probe. A clone containing an 8.5 kbp DNA was obtained from the library containing a BamHI fragment, and a clone containing a 4.9 kbp DNA was obtained from the library containing a PstI fragment. Based on the base sequence of the cDNA, the base sequence of the 4.9 kbp PstI fragment was determined. The base sequence of the genomic DNA containing the MF-1 gene is shown by SEQ ID NO:18 in Sequence Listing. According to this base sequence, the MF-1 gene encodes a polypeptide having an amino acid sequence as shown by SEQ ID NO:19 in Sequence Listing.

Further, it is made clear that there are two introns each with 37 bp and 39 bp in the genomic DNA. The relationship between the genomic DNA and the cDNA is shown in FIG. 23.

EXAMPLE 12

Cloning of Antigenic Protein MF-2 Gene from *M. furfur*

12-a) Amplification of MF-2 Gene by RT-PCR

The oligonucleotide MF2F1 deduced from the internal amino acid sequence of the MF-2 protein described in Example 10 was synthesized and purified to be used as a primer for PCR. The base sequence of MF2F1 is shown by SEQ ID NO:20 in Sequence Listing. An MF-2 cDNA fragment was amplified by carrying out RT-PCR according to the method described in Example 11-b) using the MF2F1 and M13M4 primers. As a result of the first PCR reaction, a cDNA fragment with about 280 bp in length was amplified. The base sequence of the cDNA fragment amplified is shown by SEQ ID NO:21 in Sequence Listing. The amino acid sequence deduced from SEQ ID NO:21 was identical to the amino acid sequence determined from the MF-2 protein. Therefore, it is clearly demonstrated that this cDNA fragment is an MF-2 gene.

12-b) Cloning of MF-2 cDNA

Plaque hybridization was carried out using the MF-2 cDNA fragment with about 280 bp as shown by SEQ ID NO:21 obtained in Example 12-a) as a probe according to the method described in Example 11-d). Ten clones with strong signals out of positive clones were subjected to further analysis. Specifically, *E. coli* cells harbouring the plasmid which has a region containing an MF-2 cDNA were obtained from these phages by automatic subcloning in *E. coli*. The plasmids were purified from these *E. coli* cells, and pMF2-2, which contained the longest fragment with about 550 bp cDNA, was selected. The cDNA was subcloned into a pUC118 vector, and its base sequence was then determined. The base sequence is shown by SEQ ID NO:2 in Sequence Listing, and the MF-2 gene encodes a polypeptide having an amino acid sequence as shown by SEQ ID NO:9 in Sequence Listing.

EXAMPLE 13

Cloning of Antigenic Protein MF-3 Gene from *M. furfur*

13-a) Amplification of MF-3 Gene by RT-PCR

The oligonucleotides MF3F1, MF3F2, and MF3F3 deduced from the internal amino acid sequence of the MF-3 protein described in Example 10 were synthesized and purified to be used as primers for PCR. The base sequences of MF3F1, MF3F2, and MF3F3 are shown by SEQ ID NOs:22 to 24 in Sequence Listing, respectively. An MF-3 cDNA fragment was amplified by carrying out RT-PCR according to the method described in Example 11-b) using MF3F1 and M13M4 primers in the first PCR reaction, and using a combination of MF3F1 and MF3R3 primers and a combination of MF3F2 and M13M4 primers in the second PCR reaction. As a result of the PCR reaction, a cDNA fragment with about 380 bp in length was amplified for the combination of MF3F1 and MF3R3 primers, and a cDNA fragment with about 280 bp in length was amplified for the combination of MF3F2 and M13M4 primers. The base sequences of the cDNA fragment amplified are shown by SEQ ID NOs:25 and 26 in Sequence Listing, respectively. The amino acid sequences deduced from SEQ ID NOs:25 and 26 were identical to the amino acid sequence determined from the MF-3 protein. Therefore, it is clearly demonstrated that this cDNA fragment is an MF-3 gene.

13-b) Cloning of MF-3 cDNA

Plaque hybridization was carried out using the MF-3 cDNA fragment with about 380 bp as shown by SEQ ID NO:25 obtained in Example 13-a) as a probe according to the method described in Example 11-d). Six clones with strong signals out of positive clones were subjected to further analysis. Specifically, *E. Coli* cells harbouring the plasmid which has a region containing an MF-3 cDNA were obtained from these phages by automatic subcloning in *E. Coli*. The plasmids were purified from these *E. Coli* cells, and pMF3-1, which contained the longest fragment with about 750 bp cDNA, was selected, and the base sequence of the cDNA was then determined. The base sequence is shown by SEQ ID NO:3 in Sequence Listing, and the MF-3 gene encodes a polypeptide having an amino acid sequence as shown by SEQ ID NO:10 in Sequence Listing.

EXAMPLE 14

Cloning of Antigenic Protein MF-4 Gene from *M. furfur*

14-a) Amplification of MF-4 Gene by RT-PCR

The oligonucleotides MF4F1 and MF4F2 deduced from the N-terminal amino acid sequence of the MF-4 protein described in Example 10 were synthesized and purified to be used as primers for PCR. The base sequences of MF4F1 and MF4F2 are shown by SEQ ID NOs:27 and 28 in Sequence Listing, respectively. An MF-4 cDNA fragment was amplified by carrying out RT-PCR according to the method described in Example 11-b). MF4F1 and M13M4 primers were used in the first PCR reaction, and MF4F1 and M13M4 primers were used in the second PCR reaction. As a result of the PCR reaction, a cDNA fragment with about 700 bp in length was amplified. The base sequence of the cDNA fragment amplified is shown by SEQ ID NO:29 in Sequence Listing. The amino acid sequence deduced from SEQ ID NO:29 was identical to the amino acid sequence determined from the MF-4 protein. Therefore, it is clearly demonstrated that this cDNA fragment is an MF-4 gene.

14-b) Cloning of MF-4 cDNA

Plaque hybridization was carried out using the MF-4 cDNA fragment with about 700 bp as shown by SEQ ID NO:29 obtained in Example 14-a) as a probe according to the method described in Example 11-d). Four clones with strong signals out of positive clones were subjected to further analysis. Specifically, *E. coli* cells harbouring the plasmid which has a region containing an MF-4 cDNA were obtained from these phages by automatic subcloning in *E. coli*. The plasmids were purified from these *E. coli* cells, and pMF4-4, which contained the longest fragment with about 820 bp cDNA, was selected, and the base sequence of the cDNA was then determined. The base sequence is shown by SEQ ID NO:4 in Sequence Listing, and the MF-4 gene encodes a polypeptide having an amino acid sequence as shown by SEQ ID NO:11 in Sequence Listing.

EXAMPLE 15

Cloning of Antigenic Protein MF-5 Gene from *M. furfur*

15-a) Amplification of MF-5 Gene by RT-PCR

DNAd on the N-terminal amino acid sequence of the MF-5 protein described in Example 10, since the protein was thought to share homologies with DLDH, the oligonucleotide mixture MF5F1 encoding the amino acid sequence GYVAAIKA DNAd on the above amino acid sequence and the DLDH amino acid sequence of other living organisms, and the oligonucleotide MF5R2 corresponding to a highly homologous region (amino acid sequence MLAHKAEE) when compared with DLDH amino acid sequences between other living organisms were synthesized and purified to be used as primers for PCR. The base sequences of MF5F1 and MF5F2 are shown by SEQ ID NOs:30 and 31 in Sequence Listing, respectively. An MF-5 cDNA fragment was amplified by carrying out RT-PCR according to the method described in Example 11-b). MF5F1 and M13M4 primers were used in the first PCR reaction, and MF5F1 and MF5R2 primers were used in the second PCR reaction. As a result of the PCR reaction, a cDNA fragment with about 900 bp in length was amplified. The base sequence of the cDNA fragment amplified is shown by SEQ ID NO:32 in Sequence Listing. The amino acid sequence deduced from SEQ ID NO:32 was identical to the amino acid sequence determined from the MF-5 protein. Therefore, it is clearly demonstrated that this cDNA fragment is an MF-5 gene.

15-b) Cloning of MF-5 cDNA

Plaque hybridization was carried out using the MF-5 cDNA fragment with about 900 bp as shown by SEQ ID NO:32 obtained in Example 15-a) as a probe according to the method described in Example 11-d). Twelve clones with strong signals out of positive clones were subjected to further analysis. Specifically, *E. coli* cells harbouring the plasmid which has a region containing an MF-5 cDNA were obtained from these phages by automatic subcloning in *E. coli*. The plasmids were purified from these *E. coli* cells, and pMF5-6 and pMF5-7, which contained the longest fragment with about 1.6 kbp cDNA, was selected, and the base sequence of the cDNA was then determined. The base sequences are shown by SEQ ID NOs:5 and 33 in Sequence Listing, and the MF-5 gene encodes a polypeptide having an amino acid sequence as shown by SEQ ID NOs:12 and 34 in Sequence Listing. These two kinds of genes have homology of 92% in the base sequence, and 96% in the amino acid sequence encoding thereof, and were substantially identical to the amino acid sequence determined from the MF-5 protein. Therefore, it is clearly demonstrated that both of the genes are an MF-5 gene.

EXAMPLE 16

Cloning of Antigenic Protein MF-6 Gene from *M. furfur*

16-a) Amplification of MF-6 Gene by RT-PCR

The oligonucleotide mixtures MF6F1 and MF6F2 deduced from the N-terminal amino acid sequence of the MF-6 protein described in Example 10 were synthesized and purified to be used as primers for PCR. The base sequences of MF6F1 and MF6F2 are shown by SEQ ID NOs:35 and 36 in Sequence Listing, respectively. An MF-6 cDNA fragment was amplified by carrying out RT-PCR according to the method described in Example 11-b). MF6F1 and M13M4 primers were used in the first PCR reaction, and MF6F2 and M13M4 primers were used in the second PCR reaction. As a result of the PCR reaction, a cDNA fragment with about 1.0 kbp in length was amplified. The amplified cDNA fragment was cloned into a pUC118 vector, and as a result, two kinds of cDNA having different cleavage patterns of restriction enzymes were detected. The base sequences of these cDNA fragments are shown by SEQ ID NOs:37 and 38 in Sequence Listing. Although these two genes have homology of 90% in the base sequence, and 94% in the amino acid sequence deduced from the base sequence, they are different genes. The amino acid sequences deduced from SEQ ID NOs:37 and 38 were nearly identical to the amino acid sequence determined from the MF-6 protein described in Example 10. Therefore, it is clearly demonstrated that this cDNA fragment is an MF-6 gene.

16-b) Cloning of MF-6 cDNA

Plaque hybridization was carried out using the MF-6 cDNA fragments with about 1.0 kbp as shown by SEQ ID NOs:37 and 38 obtained in Example 16-a) as probes according to the method described in Example 11-d). Ten clones with strong signals out of positive clones were subjected to further analysis. Specifically, *E. coli* cells harbouring the plasmid which has a region containing an MF-6 cDNA were obtained from these phages by automatic subcloning in *E. coli*. The plasmids were purified from these *E. coli* cells, and pMF6-13, which contained the longest fragment with about 1.2 kbp cDNA, was selected, and the base sequence of the cDNA was then determined. The base sequence is shown by SEQ ID NO:6 in Sequence Listing, and the MF-6 gene encodes a polypeptide having an amino acid sequence as shown by SEQ ID NO:13 in Sequence Listing. Although this gene lacks a encoding region of N-terminal amino acid sequence, it was nearly identical to the cDNA fragment of MF-6 obtained in Example 16-a). Therefore, it is clearly demonstrated that this cDNA fragment is an MF-6 gene.

EXAMPLE 17

Cloning of Antigenic Protein MF-7 Gene from *M. furfur*

17-a) Amplification of MF-7 Gene by RT-PCR

The oligonucleotide mixtures MF7F1 and MF7F2 deduced from the N-terminal amino acid sequence of the MF-7 protein described in Example 10 were synthesized and purified to be used as primers for PCR. The base sequences of MF7F1 and MF7F2 are shown by SEQ ID NOs:39 and 40 in Sequence Listing, respectively. An MF-7 cDNA fragment was amplified by carrying out RT-PCR according to the method described in Example 11-b). MF7F1 and M13M4 primers were used in the first PCR reaction, and MF7F2 and M13M4 primers were used in the second PCR reaction. As a result of the PCR reaction, a cDNA fragment with about 0.4 kbp in length was amplified. The amplified cDNA fragment was cloned into a pUC118 vector. The base sequence of the cDNA fragment amplified is shown by SEQ ID NO:41 in Sequence Listing. The amino acid sequence deduced from SEQ ID NO:41 was nearly identical to the amino acid sequence determined from the MF-7 protein described in Example 10. Therefore, it is clearly demonstrated that this cDNA fragment is an MF-7 gene.

17-b) Cloning of MF-7 cDNA

Plaque hybridization was carried out using the MF-7 cDNA fragment with about 0.4 kbp as shown by SEQ ID NO:41 obtained in Example 17-a) as a probe according to the method described in Example 11-d). Five clones with strong signals out of positive clones were subjected to further analysis. Specifically, *E. coli* cells harbouring the plasmid which has a region containing an MF-7 cDNA were obtained from these phages by automatic subcloning in *E. coli*. The plasmids were purified from these *E. coli* cells, and pMF7-1, which contained the longest with about 0.4 kbp cDNA, was selected, and the base sequence of the cDNA was then determined. The base sequence is shown by SEQ ID NO:7 in Sequence Listing, and the MF-7 gene encodes a polypeptide having an amino acid sequence as shown by SEQ ID NO:14 in Sequence Listing.

EXAMPLE 18

Synthesis of MF-1 Overlap Peptides and Deduction of Antigen-Binding Sites 18-a) Synthesis of MF-1 Overlap Peptides MF-1 overlap peptides were synthesized using a peptide synthesizer (PSSM-8, manufactured by Shimadzu Corporation). The entire amino acid sequence was covered by 33 kinds of peptides on the basis of the sequence of MF-1, as shown by SEQ ID NO:8 (FIG. 21), each peptide consisting of 15 (16 or 17 in some cases) amino acid residues, and being overlapped with 10 amino acid residues.

First, a resin (50 mg) previously coupled with the Fmoc form of the C-terminal amino acid of each peptide (0.2 to 0.5 mmol/g resin) was treated with 30% piperidine/DMF (0.5 ml) to remove the Fmoc group. After the resin was washed with DMF (0.6 ml×5 times), the Fmoc form of the desired amino acid activated with PyBOP and HOBt (used in DMF solution containing the Fmoc in excess by 10 times relative to the amount of the C-terminal amino acid content) and an N-methylmorpholine/DMF solution were added, followed by a reaction at room temperature for 30 minutes. The resin was then washed with DMF (0.6 ml×5 times). This series of procedures were repeated in cycles until a peptide having the desired sequence was obtained.

Next, this resin was admixed with a TFA-DNAd mixed solution (94% TFA, 5% anisole, 1% ethanedithiol (EDT)) (0.7 ml) and kept standing at room temperature for 2 hours (for tryptophan-containing peptides, a mixed solution of TFA (94%), anisole (3%), EDT (3%), and 2-methylindole (5 mg) being used; for arginine-containing peptides, a mixed solution of TFA (82%), $H_2O$ (5%), thioanisole (5%), EDT (3%), ethylmethyl sulfide (2%), and phenol (3%) being used; in the case for the arginine-containing peptides, the resin was kept standing at room temperature for 8 hours). The resin was filtered off, and ethyl ether (14 ml) was added to the filtrate to allow crystallization. The precipitated crystals were recovered by centrifugation (3,000 rpm, 10 minutes) and washed with ethyl ether, and they were then centrifuged again to remove the supernatant, and the crystals were dried under reduced pressure. The obtained crystals were assayed for its purity by reversed-phase HPLC. In addition, as occasion demands, the molecular weight was confirmed by LC-MS, and the crystals were purified by reversed-phase HPLC.

18-b) Identification of Binding Peptides to IgE Antibodies in Human Sera

Figure 22:
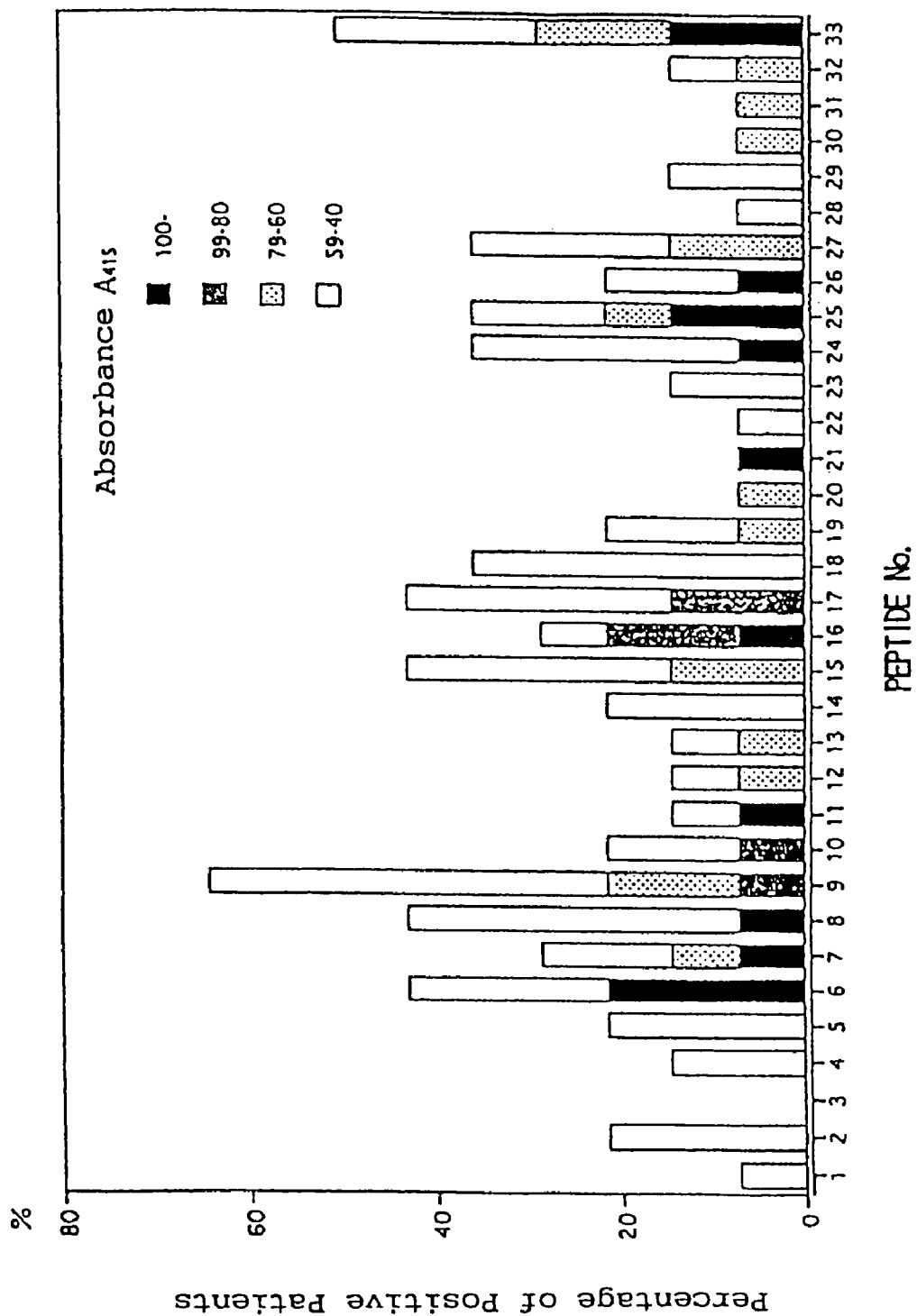
FIG. 22 is a graph showing the reaction between the MF-1 overlapping peptides and RAST positive patient sera of *M. furfur*.

Each of the peptides shown in FIG. 21 coated on a 96-well microplate at 1 µg/well using a peptide coating kit (manufactured by Takara Shuzo Co., Ltd.). A 2-fold dilution of each of 14 sera in total out of 13 sera from patients with *M. furfur* RAST positive, and 1 pooled serum was added to each well. After the reaction was carried out according to the manual, a β-galactosidase-labeled anti-IgE antibody and then an enzyme substrate were added, followed by absorbance measurement at 415 nm. The absorbance as used sera from normal individuals for 33 peptides was 20 on the average. A positive group was defined as those showing absorbance of not less than 40, which is 2-folds that of the sera from the normal individuals. The positive group having absorbance of not less than 40 was further classified into four ranks, and the results are shown in FIG. 22. The sera of patients with *M. furfur* RAST positive reacted strongly to four to five kinds of peptide fragments.

18-c) Estimation of Epitopes of Mouse Monoclonal Antibodies Against MF-1

After three monoclonal antibodies against MF-1, i.e., M-40, MmAb37, and MAb51, were added to, and reacted with, microplates coated with each of the peptides of FIG. 21 described in Example 18-b), a peroxidase-labeled anti-IgG antibody and then an enzyme substrate were added, followed by absorbance measurement at 450 nm. M-40 and MmAb37 reacted to Peptide 5, while MAb51 reacted to Peptides 25 and 26. In consideration of the above findings in combination with the results of FIG. 22, it was made clear that these peptides contained B cell epitope.

EXAMPLE 19

Application of Recombinant *Malassezia* Antigenic Proteins for Diagnosis 19-a) Method for Measuring Specific IgE Antibodies by RAST Method Activation of a paper disc with cyanogen bromide and coupling of the recombinant *Malassezia* antigenic protein to the paper disc were carried out according to the method of Miyamoto et al. (*Allergy*, 22, 584-594, 1973). One paper disc, previously coupled with the above antigenic protein, and 50 µl of sera from patients were added to a polystyrene tube, followed by incubation at room temperature for 3 hours. The paper disc was washed three times with a physiological saline containing 0.2% Tween 20, and 50 µl of the $^{125}$I-labeled anti-human IgE antibody of the RAST-RIA kit, manufactured by Pharmacia, was added, followed by incubation at room temperature overnight. After the disc was washed three times again, radioactivity was assayed using a gamma counter. The IgE antibody titer was calculated from a standard curve drawn using a reference reagent of the kit at the same time. Specimens yielding values exceeding the upper limit of the standard curve (>17.5 PRU/ml) were diluted 10 folds or 100 folds with equine serum and assayed again, followed by calculation of their antibody titer.

19-b) Diagnosis Using Recombinant *Malassezia* Antigenic Proteins rMF-1, rMF-2, and rMF-4

A skin test using the above antigenic proteins was performed on patients with atopic dermatitis (hereinafter abbreviated AD) or bronchial asthma (hereinafter abbreviated BA) or both complications (AD+BA). Forty-three out of 57 for the AD patients (75%), 108 out of 919 for the BA patients (12%), and 47 out of 102 for the AD+BA patients (46%) were positive patients, showing a very high ratio for positive in the AD patients. Also, 100%, 59%, and 85% of these AD, BA, and AD+BA patients with positive for skin tests, respectively, were positive in IgE antibody measurement by RAST method.

The IgE antibody titers for three kinds of the recombinant antigenic proteins rMF-1, rMF-2, and rMF-4 were assayed by RAST method (RIA method) on the 76 cases of patients with positive in the skin test using the above antigenic proteins and positive in RAST (1 or higher score) (AD: 30 patients, BA: 20 patients, AD+BA: 26 patients) as an object for measurement. The IgE antibody titers for the above antigenic proteins were assayed in the same manner on 12 negative individuals in the skin tests (normal individuals). As a result, it was made obvious that the IgE antibodies against antigenic proteins were present in the sera from patients at very high ratios. Especially, it was found that ratios of positive for rMF-1 and rMF-2 were high. In addition, surprisingly, the IgE antibody titers were very high. And especially in the case of the AD patients, the IgE antibody titers were 100 PRU on average, with values exceeding 1,000 PRU in some patients. Also, the IgE antibody against any one of the recombinant antigenic proteins rMF-1, rMF-2, and rMF-4 was present in the sera from all patients with RAST-positive for the *Malassezia* antigens.

INDUSTRIAL APPLICABILITY

According to the present invention, there can be provided an isolated and purified antigenic protein having high purity from *Malassezia*, antigenic fragments thereof, and a specific antibody against those antigenic protein or fragments thereof. In addition, there can be provided a diagnostic agent, a therapeutic agent, or a prophylactic drug for *Malassezia* allergoses, wherein the agent includes, as an active ingredient, the antigenic protein or fragments thereof.

Further, according to the present invention, there can be provided a novel recombinant *Malassezia* antigenic protein, genes encoding the antigenic protein, and an epitope of the antigenic protein.

The invention claimed is:

1. An isolated and purified antigenic protein from fungi of the genus *Malassezia*, wherein said antigenic protein has a partial amino acid sequence as shown by SEQ ID NO: 45, and has a molecular weight of about 21 kDa as determined by SDS-PAGE under reduced conditions and about 40 kDa as determined by SDS-PAGE under non-reduced conditions, an isoelectric point of about 4.7 in a native state, and an isoelectric point of about 5.3 in a denatured state with 8 M urea.

2. The antigenic protein according to claim 1, wherein said antigenic protein has the amino acid sequence as shown by SEQ ID NO: 8.

3. A diagnostic agent for *Malassezia* allergies or *Malassezia* infectious disease, wherein said diagnostic agent includes, as a biologically active ingredient, the antigenic protein according to claims 1 or 2.

4. A therapeutic agent for *Malassezia* allergies or *Malassezia* infectious disease, wherein said therapeutic agent includes, as a biologically active ingredient, the antigenic protein according to claims 1 or 2.

* * * * *